(12) United States Patent
Scheib et al.

(10) Patent No.: US 10,925,598 B2
(45) Date of Patent: Feb. 23, 2021

(54) ROBOTICALLY-ASSISTED SURGICAL SUTURING SYSTEMS

(71) Applicant: Ethicon LLC, Guaynabo, PR (US)

(72) Inventors: Charles J. Scheib, Loveland, OH (US); Jeffrey S. Swayze, West Chester, OH (US)

(73) Assignee: Ethicon LLC, Guaynabo, PR (US)

( * ) Notice: Subject to any disclaimer, the term of this patent is extended or adjusted under 35 U.S.C. 154(b) by 0 days.

(21) Appl. No.: 16/128,170

(22) Filed: Sep. 11, 2018

(65) Prior Publication Data

US 2020/0015806 A1 Jan. 16, 2020

Related U.S. Application Data

(60) Provisional application No. 62/698,625, filed on Jul. 16, 2018.

(51) Int. Cl.
*A61B 17/04* (2006.01)
*A61B 17/06* (2006.01)
(Continued)

(52) U.S. Cl.
CPC ...... *A61B 17/0482* (2013.01); *A61B 1/00006* (2013.01); *A61B 1/00043* (2013.01); *A61B 1/00045* (2013.01); *A61B 1/00096* (2013.01); *A61B 1/00149* (2013.01); *A61B 1/04* (2013.01); *A61B 1/045* (2013.01); *A61B 1/05* (2013.01); *A61B 1/051* (2013.01); *A61B 1/06* (2013.01); *A61B 1/063* (2013.01); *A61B 1/0607* (2013.01); *A61B 1/0638* (2013.01); *A61B 1/0661* (2013.01); *A61B 1/07* (2013.01); *A61B 1/3132* (2013.01); *A61B 5/0036* (2018.08); *A61B 5/0086* (2013.01); *A61B 5/0095* (2013.01); *A61B 17/00234* (2013.01); (Continued)

(58) Field of Classification Search
None
See application file for complete search history.

(56) References Cited

U.S. PATENT DOCUMENTS 5,460,182 A 10/1995 Goodman et al.
5,609,562 A 3/1997 Kaali
(Continued)

FOREIGN PATENT DOCUMENTS

JP 2006280591 A 10/2006

OTHER PUBLICATIONS

Kurata et al. "Time-of-flight Near-infrared Spectroscopy for Non-destructive Measurement of Internal Quality in Grapefruit," J. Amer. Soc. Hort. Sci. 138(3): 225-228, 2013.
(Continued)

*Primary Examiner* — Bhavesh V Amin

(57) ABSTRACT

A surgical suturing tracking system configured for use with a suturing needle is disclosed. The surgical suturing tracking system comprises a spectral light emitter, a waveform sensor, and a control circuit coupled to the waveform sensor. The control circuit is configured to cause the spectral light emitter to emit spectral light waves toward a suturing needle and a tissue structure, receive an input corresponding to the spectral light waves reflected by the needle and the tissue structure and determine a distance between the needle and the tissue structure based on the received input.

20 Claims, 23 Drawing Sheets

(51) Int. Cl.

| | | |
|---|---|---|
| A61B 17/062 | (2006.01) | |
| A61B 34/32 | (2016.01) | |
| A61B 34/20 | (2016.01) | |
| A61B 34/30 | (2016.01) | |
| A61B 1/045 | (2006.01) | |
| A61B 1/06 | (2006.01) | |
| A61B 1/07 | (2006.01) | |
| A61B 1/313 | (2006.01) | |
| A61B 17/00 | (2006.01) | |
| A61B 17/34 | (2006.01) | |
| A61B 17/11 | (2006.01) | |
| A61B 17/115 | (2006.01) | |
| A61B 17/064 | (2006.01) | |
| A61B 90/30 | (2016.01) | |
| A61B 90/00 | (2016.01) | |
| A61B 1/05 | (2006.01) | |
| A61B 1/00 | (2006.01) | |
| A61B 5/00 | (2006.01) | |
| A61B 90/13 | (2016.01) | |
| A61B 34/00 | (2016.01) | |
| A61B 90/35 | (2016.01) | |
| A61B 17/02 | (2006.01) | |
| A61B 1/04 | (2006.01) | |
| A61B 34/10 | (2016.01) | |

(52) U.S. Cl.
CPC ...... *A61B 17/0218* (2013.01); *A61B 17/0469* (2013.01); *A61B 17/0483* (2013.01); *A61B 17/062* (2013.01); *A61B 17/064* (2013.01); *A61B 17/06066* (2013.01); *A61B 17/1114* (2013.01); *A61B 17/1155* (2013.01); *A61B 17/3423* (2013.01); *A61B 34/20* (2016.02); *A61B 34/30* (2016.02); *A61B 34/32* (2016.02); *A61B 34/73* (2016.02); *A61B 90/03* (2016.02); *A61B 90/13* (2016.02); *A61B 90/30* (2016.02); *A61B 90/35* (2016.02); *A61B 90/36* (2016.02); *A61B 90/361* (2016.02); *A61B 90/37* (2016.02); *A61B 1/00009* (2013.01); *A61B 1/0676* (2013.01); *A61B 2017/00061* (2013.01); *A61B 2017/00119* (2013.01); *A61B 2017/00367* (2013.01); *A61B 2017/00477* (2013.01); *A61B 2017/00876* (2013.01); *A61B 2034/105* (2016.02); *A61B 2034/107* (2016.02); *A61B 2034/2051* (2016.02); *A61B 2034/2055* (2016.02); *A61B 2034/2057* (2016.02); *A61B 2034/2063* (2016.02); *A61B 2034/2065* (2016.02); *A61B 2034/301* (2016.02); *A61B 2034/302* (2016.02); *A61B 2090/061* (2016.02); *A61B 2090/064* (2016.02); *A61B 2090/306* (2016.02); *A61B 2090/367* (2016.02); *A61B 2090/373* (2016.02); *A61B 2090/374* (2016.02); *A61B 2090/378* (2016.02); *A61B 2090/3762* (2016.02); *A61B 2505/05* (2013.01); *A61B 2560/0462* (2013.01); *A61B 2576/00* (2013.01)

(56) References Cited

U.S. PATENT DOCUMENTS

| | | |
|---|---|---|
| 6,350,233 B1 | 2/2002 | Lubowski |
| 7,477,931 B2 | 1/2009 | Hoyt |
| 7,901,353 B2 | 3/2011 | Vayser et al. |
| 8,932,208 B2 | 1/2015 | Kendale et al. |
| 8,992,558 B2 | 3/2015 | Stone et al. |
| 9,072,501 B2 | 7/2015 | Menchaca et al. |
| 9,072,535 B2 | 7/2015 | Shelton, IV et al. |
| 9,161,820 B2 | 10/2015 | Mark et al. |
| 9,179,822 B2 | 11/2015 | Kitamura et al. |
| 9,241,693 B2 | 1/2016 | Taylor et al. |
| 9,274,047 B2* | 3/2016 | Velten ................ G01B 11/2513 |
| 9,282,878 B2 | 3/2016 | Grey et al. |
| 9,857,167 B2 | 1/2018 | Jovanovski et al. |
| 10,068,173 B2 | 9/2018 | Vayser et al. |
| 10,123,706 B2 | 11/2018 | Elbaz et al. |
| 10,170,205 B2 | 1/2019 | Curd et al. |
| 10,194,981 B2 | 2/2019 | Margallo Balbas et al. |
| 10,512,518 B2 | 12/2019 | Vayser et al. |
| 10,687,797 B2 | 6/2020 | Stone et al. |
| 2004/0176751 A1 | 9/2004 | Weitzner et al. |
| 2005/0279354 A1 | 12/2005 | Deutsch et al. |
| 2006/0206007 A1 | 9/2006 | Bala |
| 2007/0100210 A1 | 5/2007 | Selover et al. |
| 2008/0151233 A1 | 6/2008 | Blanke et al. |
| 2010/0152539 A1 | 6/2010 | Ghabrial et al. |
| 2012/0265022 A1 | 10/2012 | Menn |
| 2012/0300051 A1 | 11/2012 | Daigo et al. |
| 2015/0238276 A1 | 8/2015 | Atarot et al. |
| 2016/0038004 A1 | 2/2016 | Tanaka |
| 2016/0183841 A1 | 6/2016 | Duindam et al. |
| 2017/0055819 A1 | 3/2017 | Hansen et al. |
| 2017/0209050 A1 | 7/2017 | Fengler et al. |
| 2017/0251900 A1 | 9/2017 | Hansen et al. |
| 2018/0014851 A1 | 1/2018 | Hansen et al. |
| 2018/0271603 A1 | 9/2018 | Nir et al. |
| 2019/0099070 A1 | 4/2019 | Mark et al. |
| 2019/0200905 A1 | 7/2019 | Shelton, IV et al. |
| 2019/0201047 A1* | 7/2019 | Yates ................ A61B 1/00009 |
| 2019/0201111 A1 | 7/2019 | Shelton, IV et al. |
| 2019/0201120 A1 | 7/2019 | Shelton, IV et al. |
| 2019/0201142 A1 | 7/2019 | Shelton, IV et al. |
| 2019/0320117 A1 | 10/2019 | Wu et al. |
| 2020/0015668 A1 | 1/2020 | Scheib |
| 2020/0015897 A1 | 1/2020 | Scheib et al. |
| 2020/0015898 A1 | 1/2020 | Scheib et al. |
| 2020/0015899 A1 | 1/2020 | Scheib et al. |
| 2020/0015900 A1 | 1/2020 | Scheib et al. |
| 2020/0015901 A1 | 1/2020 | Scheib et al. |
| 2020/0015902 A1 | 1/2020 | Scheib et al. |
| 2020/0015903 A1 | 1/2020 | Scheib et al. |
| 2020/0015904 A1 | 1/2020 | Scheib et al. |
| 2020/0015905 A1 | 1/2020 | Scheib et al. |
| 2020/0015906 A1 | 1/2020 | Scheib et al. |
| 2020/0015907 A1 | 1/2020 | Scheib |
| 2020/0015914 A1 | 1/2020 | Scheib et al. |
| 2020/0015923 A1 | 1/2020 | Scheib et al. |
| 2020/0015924 A1 | 1/2020 | Scheib et al. |
| 2020/0015925 A1 | 1/2020 | Scheib |
| 2020/0037858 A1 | 2/2020 | Pedreira De Cerqueira Filho |

OTHER PUBLICATIONS

Thyroid Fine Needle Aspiration (FNA) Biopsy, retrieved from www.fairview.org/patient-education/90246 on Feb. 4, 2020. 3 pages.

Open Technique for Low Anterior Resection, retrieved from https://abdominalkey.com/open-technique-for-low-anterior-resection/ on Feb. 4, 2020. 6 pages.

Sukumar et al., "Robotic Partial Nephrectomy Using Robotic Bulldog Clamps," JSLS: Journal of the Society of Laparoendoscopic Surgeons, 15(4), pp. 520-526, 2011.

X12C4 Robotic Drop-In, retrieved from https://bkultrasound.com/transducers/x12c4-robotic-drop-in on Feb. 13, 2020. 2 pages.

"ATM-MPLS Networking Version 2.0, af-aic-0178.001" ATM Standard, The ATM Forum Technical Committee, published Aug. 2003.

IEEE Std 802.3-2012 (Revision of IEEE Std 802.3-2008, published Dec. 28, 2012.

Lacy, Antonio, "Main Steps to Perform a Sleeve Gastrectomy," retrieved from https://aischannel.com/society/main-steps-to-perform-a-sleeve-gastrectomy/ on Feb. 14, 2020. pp. 1-7, Jun. 11, 2015.

(56) References Cited

OTHER PUBLICATIONS

Elhajj, et al., "Sleeve Gastrectomy Surgical Assistive Instrument for Accurate Remnant Stomach Volume," ASME, J. Med. Devices, vol. 4, pp. 1-10, Jun. 2010.

* cited by examiner

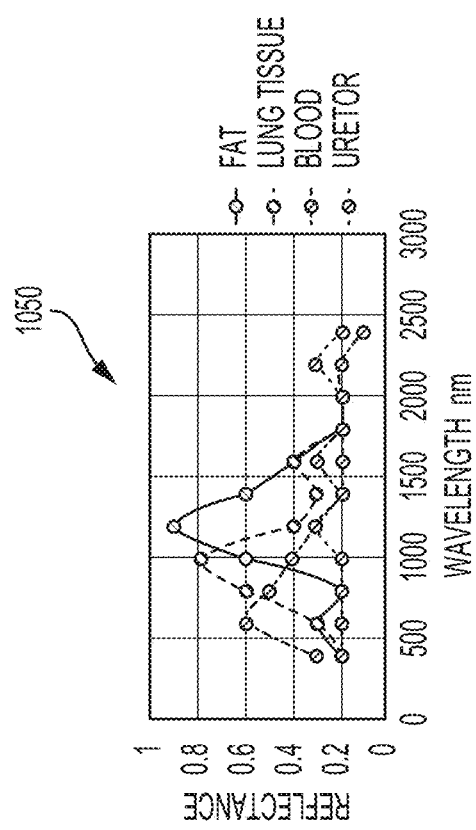
FIG. 16
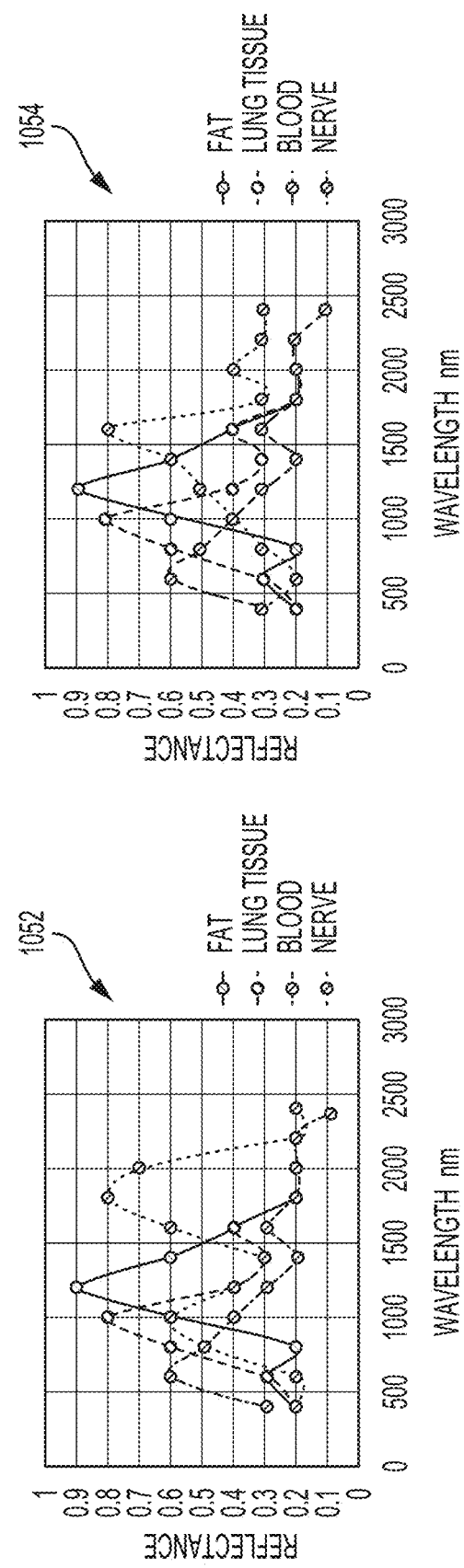
FIG. 17
FIG. 18

ROBOTICALLY-ASSISTED SURGICAL SUTURING SYSTEMS

CROSS-REFERENCE TO RELATED APPLICATION

This application claims the benefit of priority under 35 U.S.C. § 119(e) to U.S. Provisional Patent Application Ser. No. 62/698,625, titled DIGITAL SURGERY IMAGING/VISUALIZATION SYSTEM, filed Jul. 16, 2018, the disclosure of which is herein incorporated by reference in its entirety.

BACKGROUND

Surgical systems often incorporate an imaging system, which can allow the clinician(s) to view the surgical site and/or one or more portions thereof on one or more displays such as a monitor, for example. The display(s) can be local and/or remote to a surgical theater. An imaging system can include a scope with a camera that views the surgical site and transmits the view to a display that is viewable by a clinician. Scopes include, but are not limited to, arthroscopes, angioscopes, bronchoscopes, choledochoscopes, colonoscopes, cytoscopes, duodenoscopes, enteroscopes, esophagogastro-duodenoscopes (gastroscopes), endoscopes, laryngoscopes, nasopharyngo-neproscopes, sigmoidoscopes, thoracoscopes, ureteroscopes, and exoscopes. Imaging systems can be limited by the information that they are able to recognize and/or convey to the clinician(s). For example, certain concealed structures, physical contours, and/or dimensions within a three-dimensional space may be unrecognizable intraoperatively by certain imaging systems. Additionally, certain imaging systems may be incapable of communicating and/or conveying certain information to the clinician(s) intraoperatively.

SUMMARY

In various embodiments, a surgical suturing tracking system configured for use with a suturing needle is disclosed. The surgical suturing tracking system comprises a spectral light emitter, a waveform sensor, and a control circuit coupled to the waveform sensor. The control circuit is configured to cause the spectral light emitter to emit spectral light waves toward a suturing needle and a tissue structure, receive an input corresponding to the spectral light waves reflected by the needle and the tissue structure and determine a distance between the needle and the tissue structure based on the received input.

FIGURES

The novel features of the various aspects are set forth with particularity in the appended claims. The described aspects, however, both as to organization and methods of operation, may be best understood by reference to the following description, taken in conjunction with the accompanying drawings in which:

FIGS. 7A and 7B are views of the critical structure taken by the three-dimensional camera of FIG. 6, in which FIG. 7A is a view from a left-side lens of the three-dimensional camera and FIG. 7B is a view from a right-side lens of the three-dimensional camera, according to at least one aspect of the present disclosure.

Figure 15C:
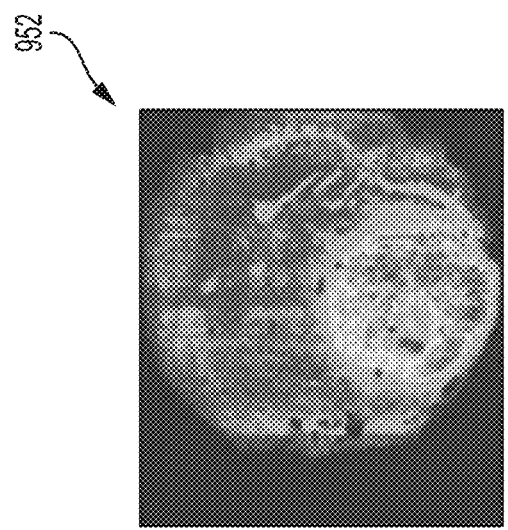
Figure 15B:
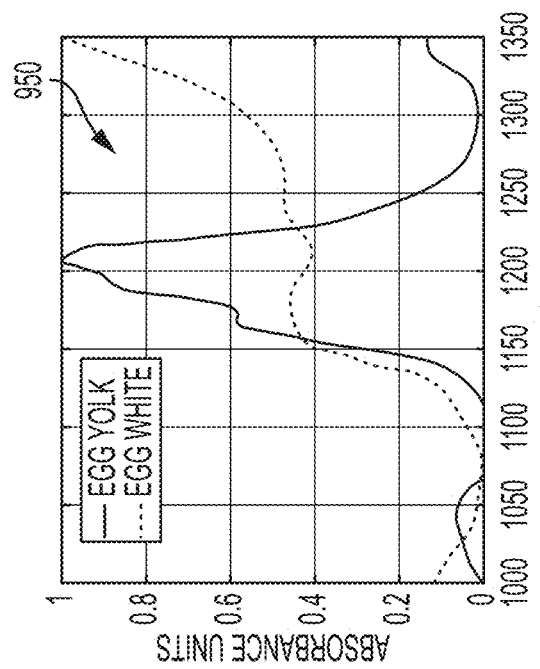
Figure 15A:
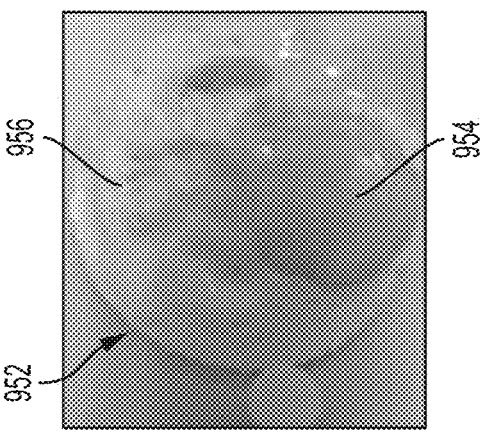

FIGS. 15A-15C show an example of a hyperspectral visualization system for imaging a fried egg, wherein FIG. 15A is a photograph of the fried egg, FIG. 15B is a graphical representation of hyperspectral signatures for an egg yolk portion and an egg white portion of the fried egg, and FIG. 15C is a hyperspectral image (shown in black-and-white) of the fried egg, in which an augmented image differentiates between the egg yolk portion and the egg white portion based on hyperspectral signature data, according to at least one aspect of the present disclosure.

FIGS. 16-18 depict illustrative hyperspectral identifying signatures to differentiate anatomy from obscurants, wherein FIG. 16 is a graphical representation of a ureter signature versus obscurants, FIG. 17 is a graphical representation of an artery signature versus obscurants, and FIG. 18 is a graphical representation of a nerve signature versus obscurants, according to at least one aspect of the present disclosure.

Figure 19:
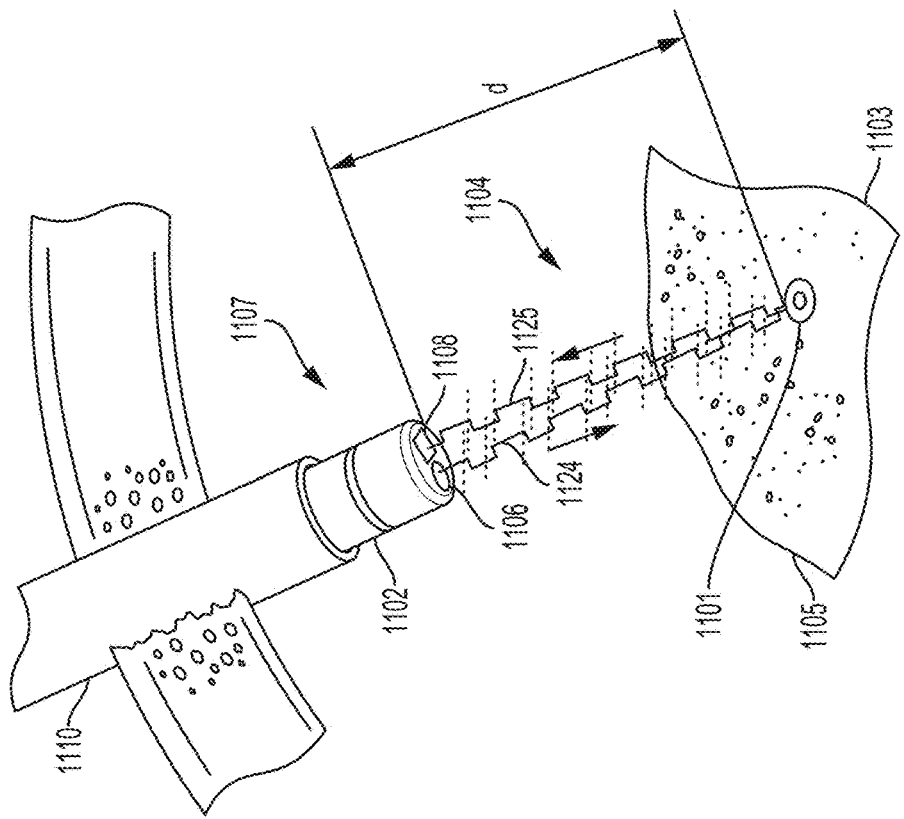

FIG. 19 is a schematic of a near infrared (NIR) time-of-flight measurement system configured to sense distance to a critical anatomical structure, the time-of-flight measurement system including a transmitter (emitter) and a receiver (sensor) positioned on a common device, according to at least one aspect of the present disclosure.

Figure 20:
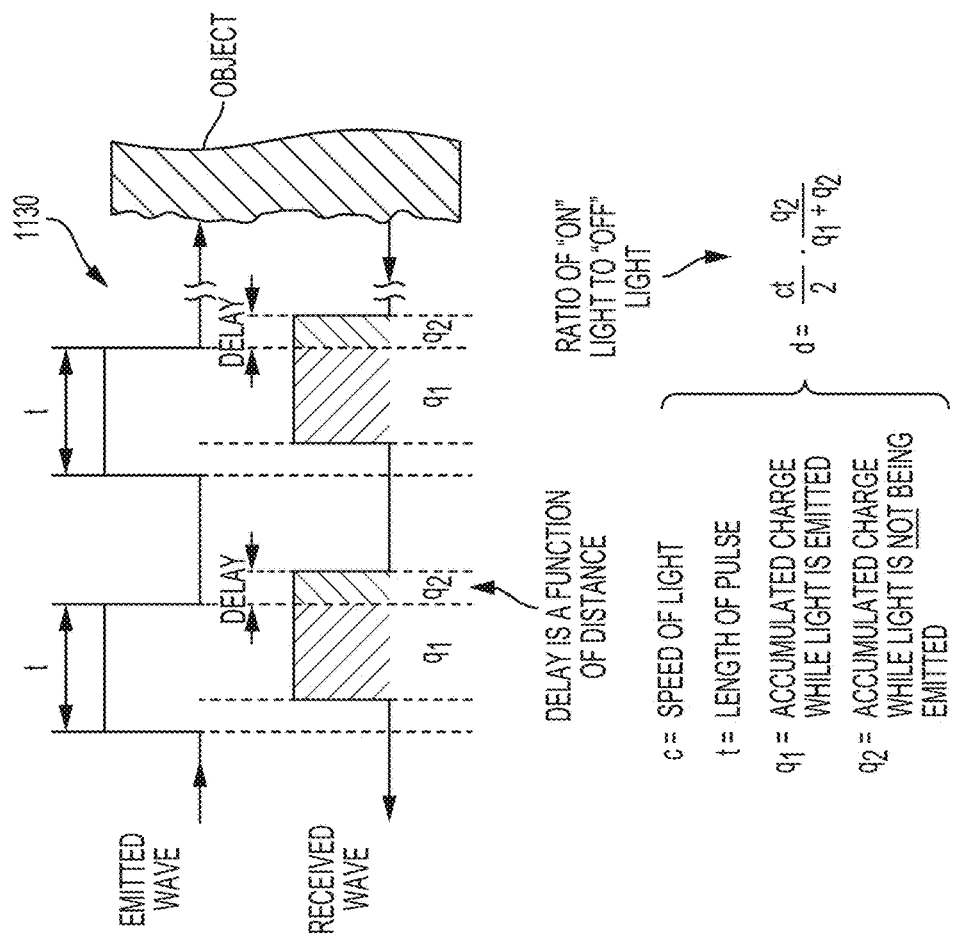

FIG. 20 is a schematic of an emitted wave, a received wave, and a delay between the emitted wave and the received wave of the NIR time-of-flight measurement system of FIG. 19, according to at least one aspect of the present disclosure.

Figure 21:
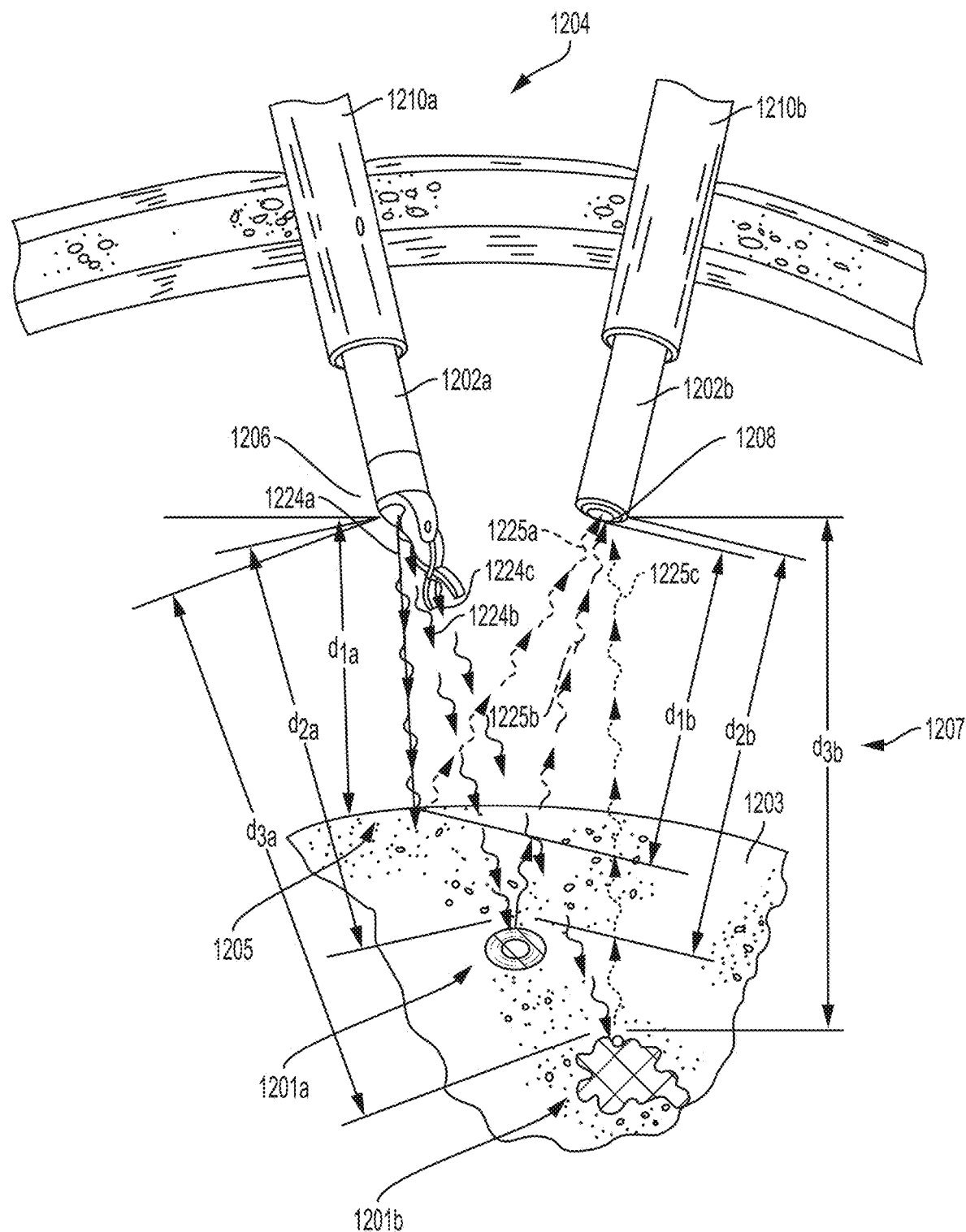

FIG. 21 illustrates a NIR time-of-flight measurement system configured to sense a distance to different structures, the time-of-flight measurement system including a transmitter (emitter) and a receiver (sensor) on separate devices, according to one aspect of the present disclosure.

Figure 22:
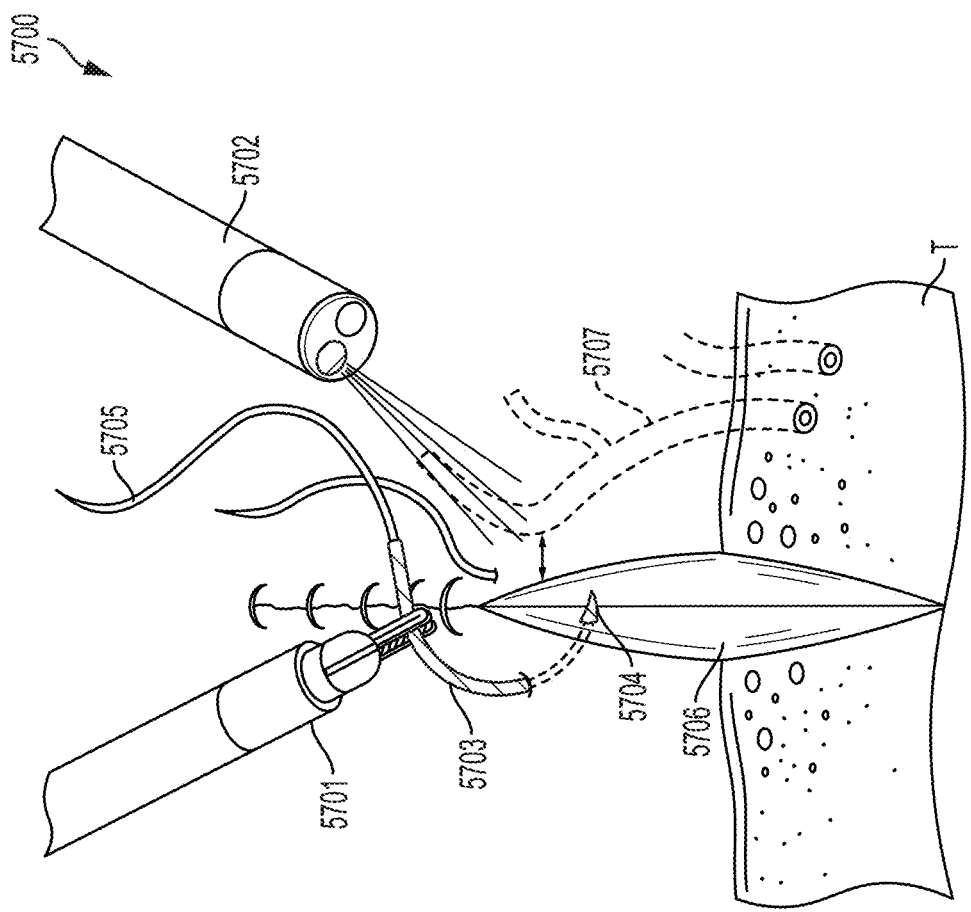

FIG. 22 is a partial perspective view of a robotically-assisted suturing system comprising a grasper, a suturing needle, and a surgical visualization assembly, according to at least one aspect of the present disclosure.

Figure 23:
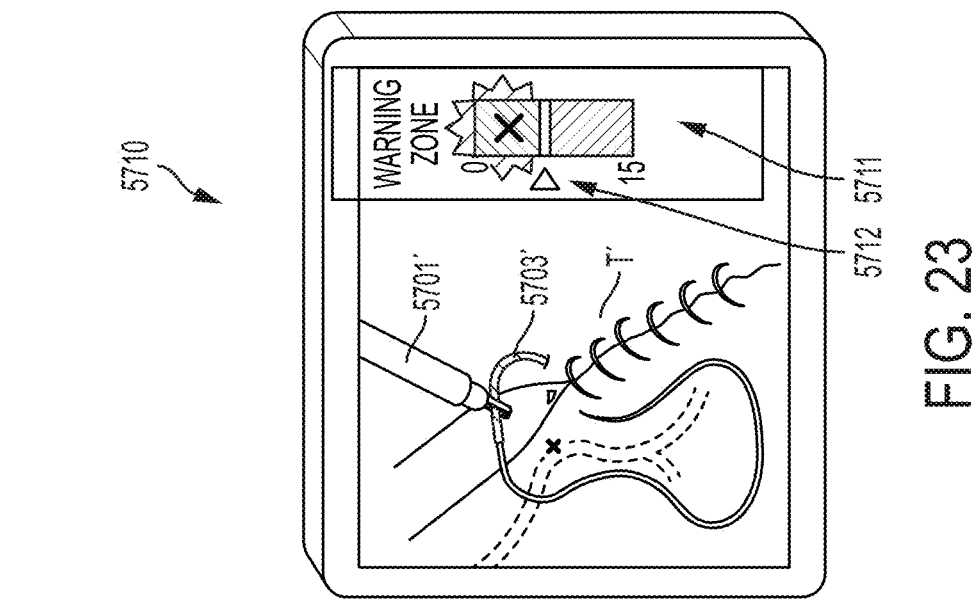

FIG. 23 is a perspective view a video monitor displaying information gathered by a waveform sensor in a surgical site, according to at least one aspect of the present disclosure.

Figure 24:
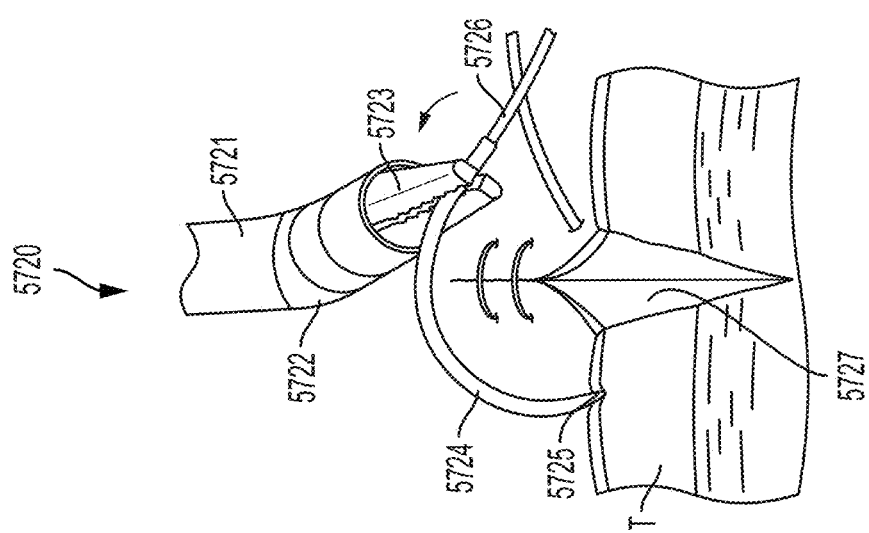

FIG. 24 illustrates a first phase of a robotically assisted suture motion using a grasper and a suture needle where a surgeon manually touches the suture needle to the surface of tissue with the grasper.

Figure 25:
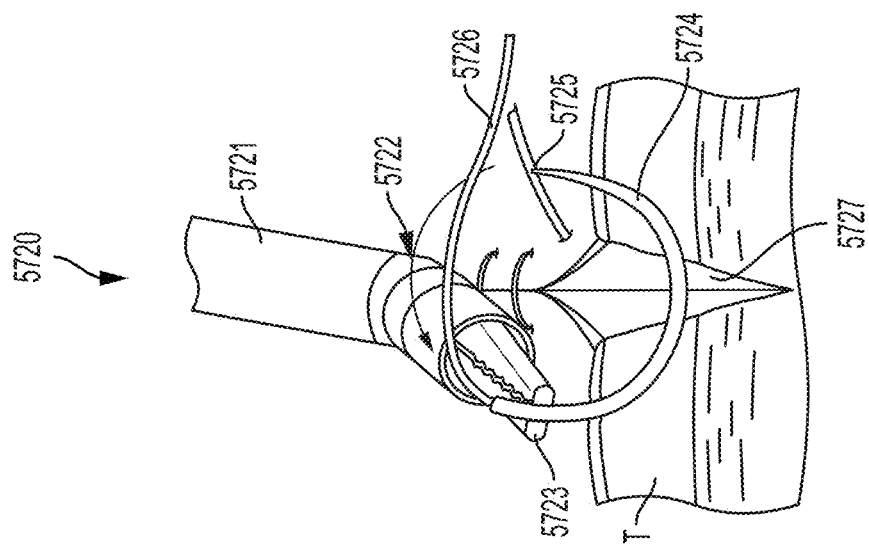

FIG. 25 illustrates a second phase of the robotically assisted suture motion of FIG. 24 where a surgeon initiates an automatic, robotically-assisted portion of the suture motion where the grasper is actuated through a suturing stroke by the robotic system automatically.

Figure 26:
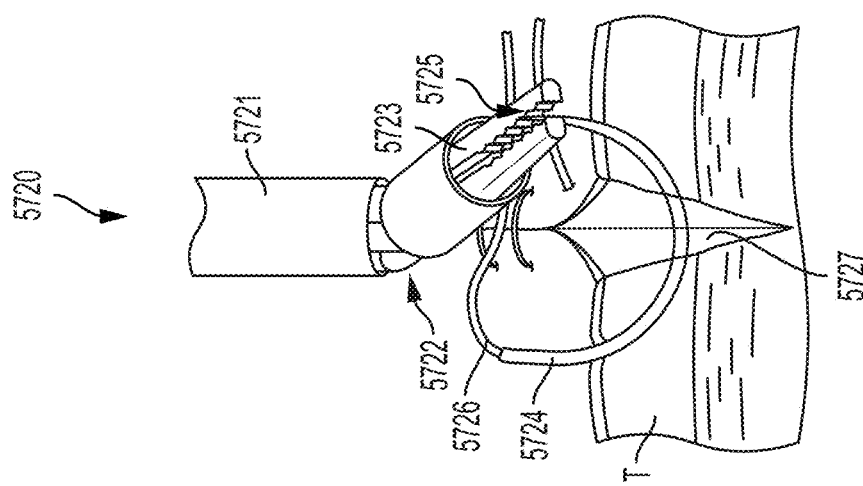

FIG. 26 illustrates a third phase of the robotically assisted suture motion of FIG. 24 where the grasper grabs a tip of the suture needle.

Figure 27:
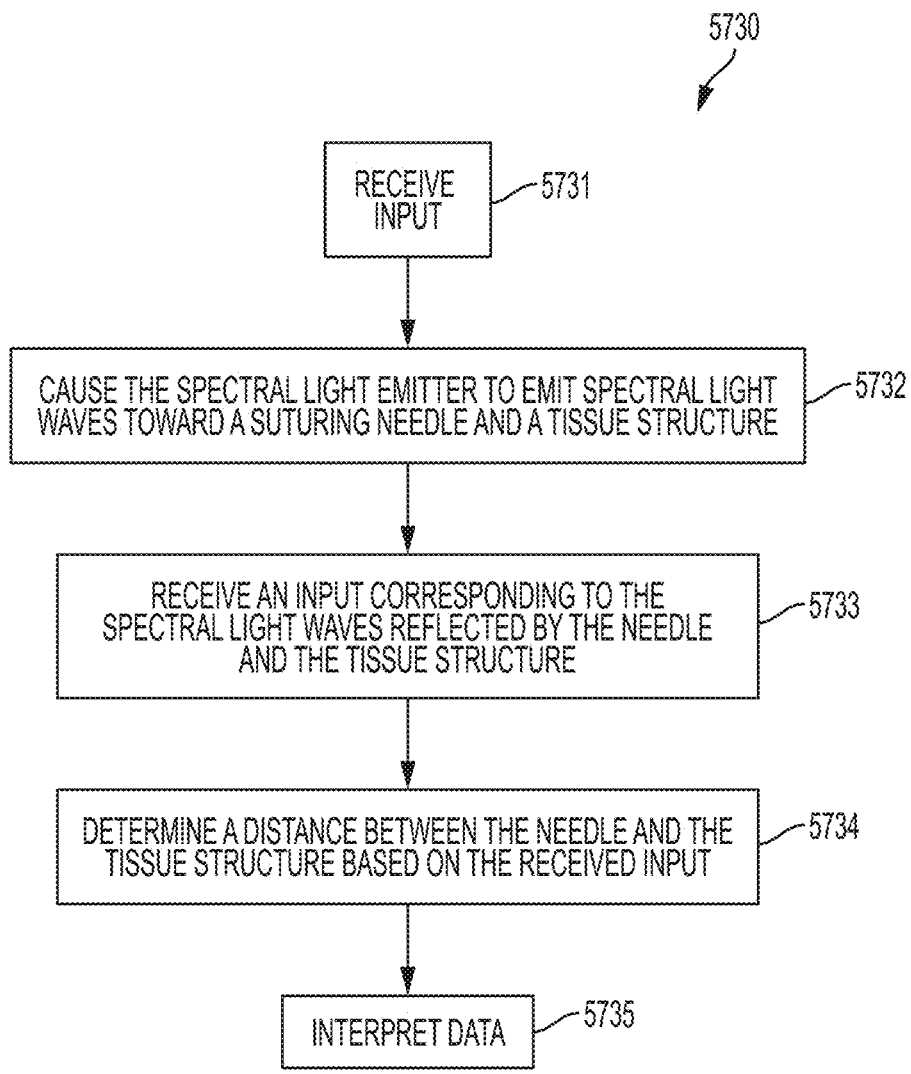

FIG. 27 is a flowchart depicting an algorithm for a surgical visualization feedback system used to determine the relative position of a suturing needle and an embedded tissue structure.

Figure 28:
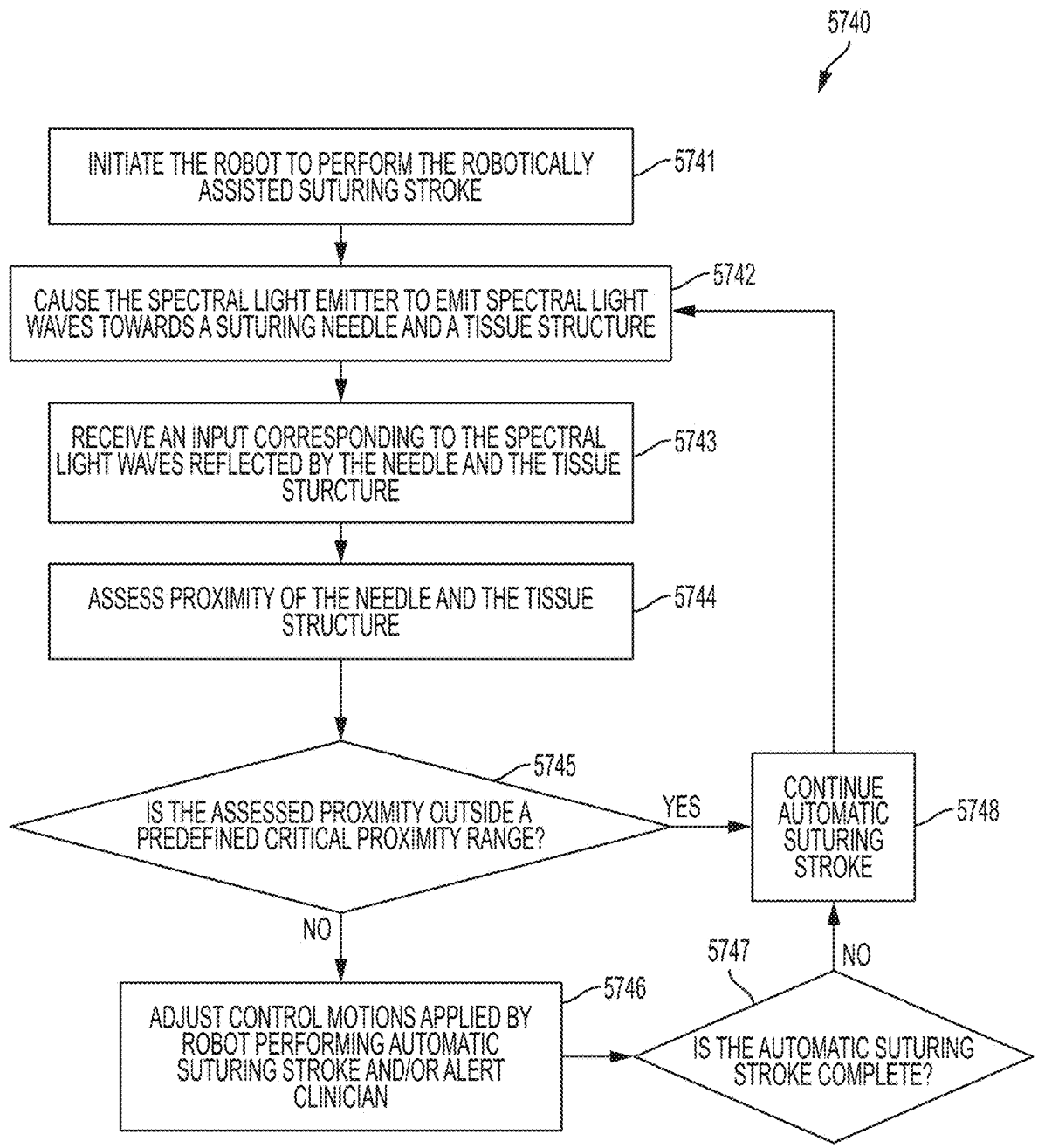

FIG. 28 is a flowchart depicting an algorithm for a surgical visualization feedback system for use with a surgical suturing system.

Figure 29:
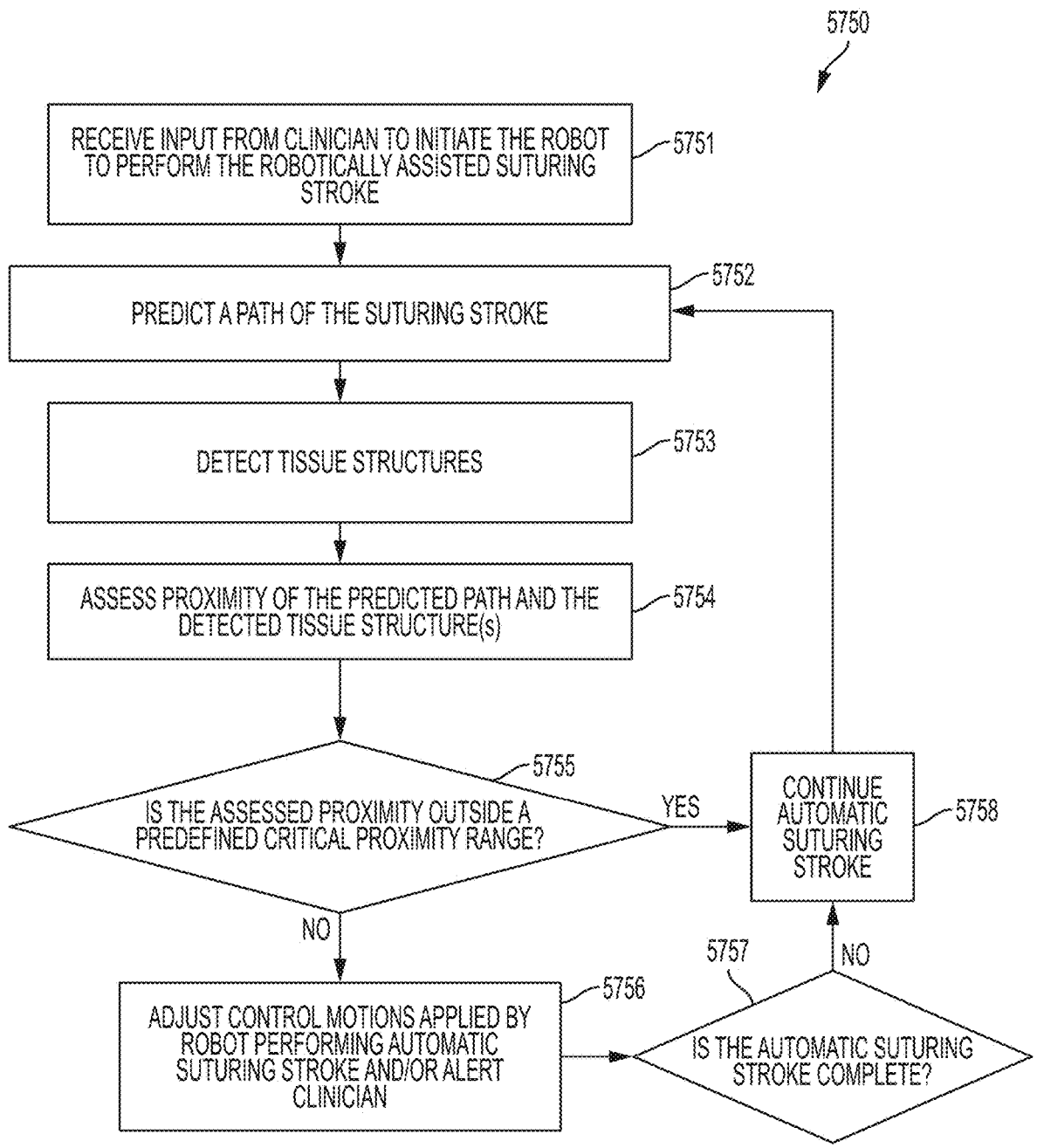

FIG. 29 is a flowchart depicting an algorithm for a surgical visualization feedback system for use with a robotically-assisted surgical suturing system.

Figure 30:
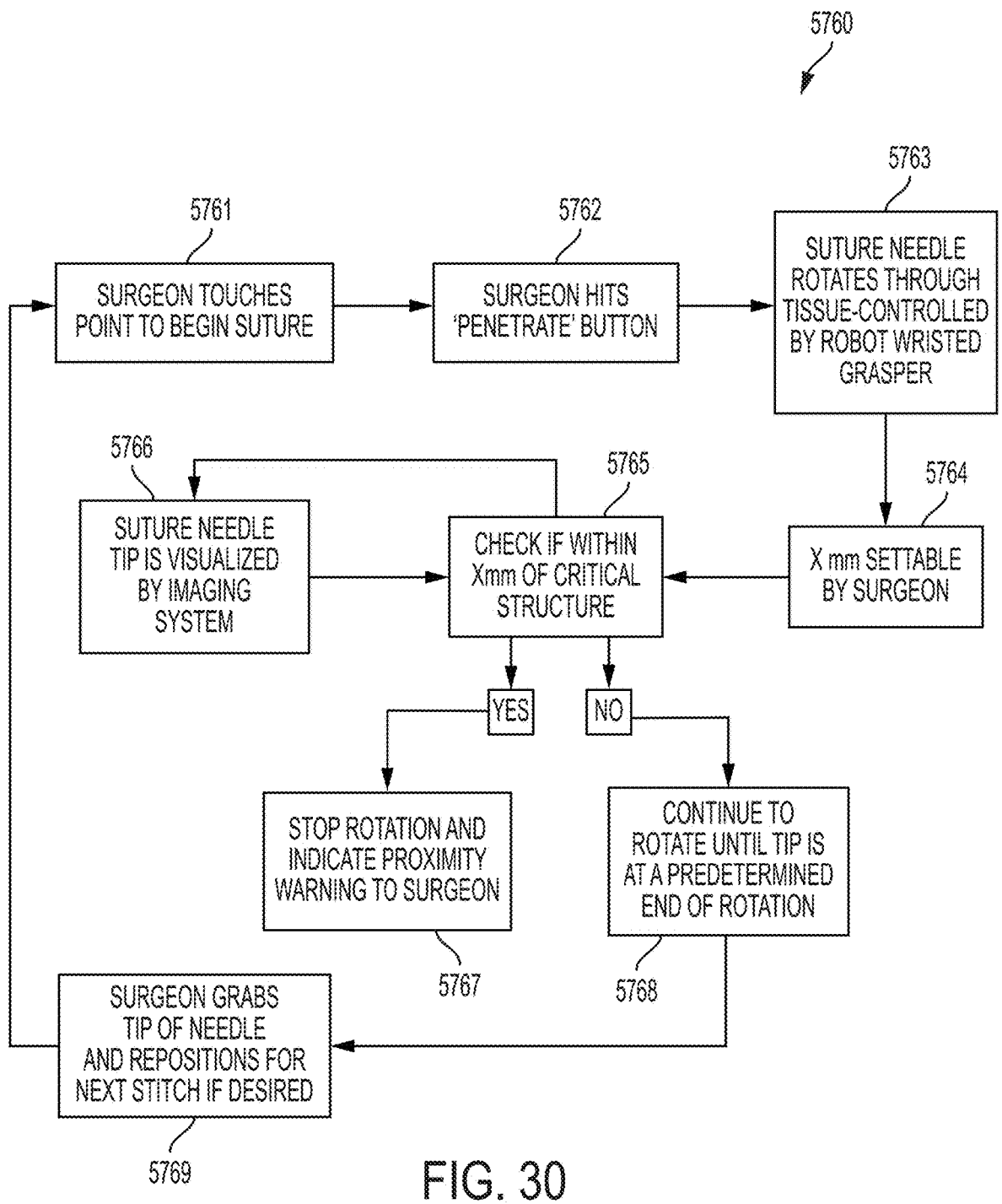

FIG. 30 is a flowchart of a process utilizing a robotically assisted suturing system, according to at least one aspect of the present disclosure.

Figure 31:
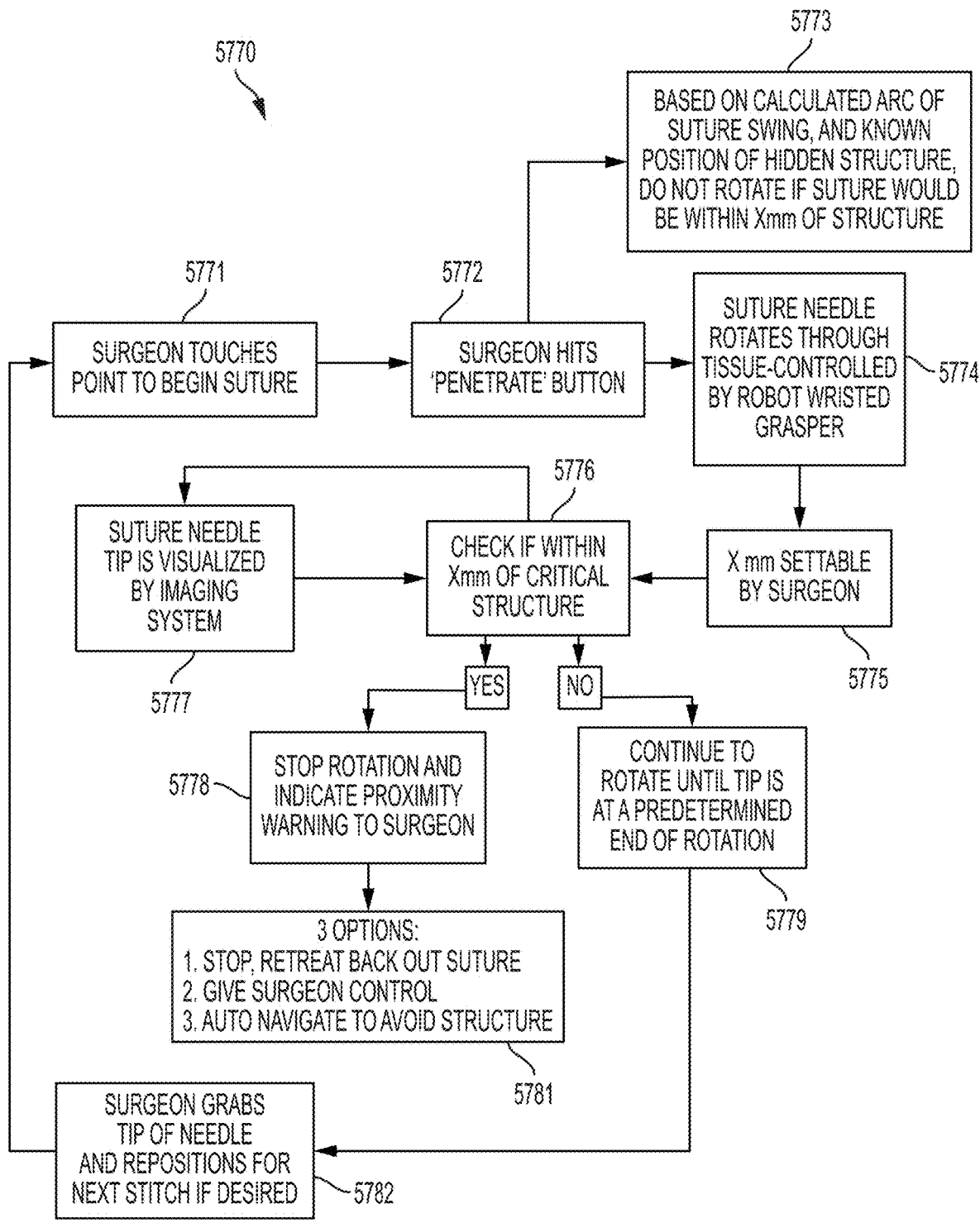

FIG. 31 is a flowchart of a process utilizing a robotically assisted suturing system, according to at least one aspect of the present disclosure.

DESCRIPTION

Applicant of the present application also owns the following U.S. Patent Applications, filed Sep. 11, 2018, each of which is herein incorporated by reference in its entirety:

U.S. patent application Ser. No. 16/128,179, titled SURGICAL VISUALIZATION PLATFORM, now U.S. Patent Application Publication No. 2020/0015923;

U.S. patent application Ser. No. 16/128,191, titled SURGICAL VISUALIZATION CONTROLS, now U.S. Patent Application Publication No. 2020/0015904;

U.S. patent application Ser. No. 16/128,180, titled CONTROLLING AN EMITTER ASSEMBLY PULSE SEQUENCE, now U.S. Patent Application Publication No. 2020/0015900;

U.S. patent application Ser. No. 16/128,198, titled COMBINATION EMITTER AND CAMERA ASSEMBLY, now U.S. Patent Application Publication No. 2020/0015668;

U.S. patent application Ser. No. 16/128,207, titled SINGULAR EMR SOURCE WITH DUAL OUTPUT EMITTER ASSEMBLY, now U.S. Patent Application Publication No. 2020/0015925;

U.S. patent application Ser. No. 16/128,176, titled SURGICAL VISUALIZATION WITH PROXIMITY TRACKING FEATURES, now U.S. Patent Application Publication No. 2020/0015899;

U.S. patent application Ser. No. 16/128,187, titled SURGICAL VISUALIZATION OF MULTIPLE TARGETS, now U.S. Patent Application Publication No. 2020/0015903;

U.S. patent application Ser. No. 16/128,192, titled VISUALIZATION OF SURGICAL DEVICES, now U.S. Patent Application Publication No. 2020/0015905;

U.S. patent application Ser. No. 16/128,163, titled OPERATIVE COMMUNICATION OF LIGHT, now U.S. Patent Application Publication No. 2020/0015897;

U.S. patent application Ser. No. 16/128,197, titled ROBOTIC LIGHT PROJECTION TOOLS, now U.S. Patent Application Publication No. 2020/0015924;

U.S. patent application Ser. No. 16/128,164, titled SURGICAL VISUALIZATION FEEDBACK SYSTEM, now U.S. Patent Application Publication No. 2020/0015898;

U.S. patent application Ser. No. 16/128,193, titled SURGICAL VISUALIZATION AND MONITORING, now U.S. Patent Application Publication No. 2020/0015907;

U.S. patent application Ser. No. 16/128,195, titled INTEGRATION OF IMAGING DATA, now U.S. Patent Application Publication No. 2020/0015907;

U.S. patent application Ser. No. 16/128,183, titled SAFETY LOGIC FOR SURGICAL SUTURING SYSTEMS, now U.S. Patent Application Publication No. 2020/0015901;

U.S. patent application Ser. No. 16/128,172, titled ROBOTIC SYSTEM WITH SEPARATE PHOTOACOUSTIC RECEIVER, now U.S. Patent Application Publication No. 2020/0015914; and U.S. patent application Ser. No. 16/128,185, titled FORCE SENSOR THROUGH STRUCTURED LIGHT DEFLECTION, now U.S. Patent Application Publication No. 2020/0015902.

Applicant of the present application also owns U.S. Pat. No. 9,072,535, titled SURGICAL STAPLING INSTRUMENTS WITH ROTATABLE STAPLE DEPLOYMENT ARRANGEMENTS, issued Jul. 7, 2015, which is incorporated by reference herein in its entirety.

Applicant of the present application also owns U.S. Provisional Patent Application No. 62/611,339, titled ROBOT ASSISTED SURGICAL PLATFORM, filed Dec. 28, 2017, which is incorporated by reference herein in its entirety.

Applicant of the present application also owns the following U.S. Patent Applications, filed on Mar. 29, 2018, each of which is herein incorporated by reference in its entirety:

U.S. patent application Ser. No. 15/940,627, titled DRIVE ARRANGEMENTS FOR ROBOT-ASSISTED SURGICAL PLATFORMS;

U.S. patent application Ser. No. 15/940,676, titled AUTOMATIC TOOL ADJUSTMENTS FOR ROBOT-ASSISTED SURGICAL PLATFORMS;

U.S. patent application Ser. No. 15/940,711, titled SENSING ARRANGEMENTS FOR ROBOT-ASSISTED SURGICAL PLATFORMS; and U.S. patent application Ser. No. 15/940,722, titled CHARACTERIZATION OF TISSUE IRREGULARITIES THROUGH THE USE OF MONO-CHROMATIC LIGHT REFRACTIVITY, filed Mar. 29, 2018, which is incorporated by reference herein in its entirety.

Before explaining various aspects of a surgical visualization platform in detail, it should be noted that the illustrative examples are not limited in application or use to the details of construction and arrangement of parts illustrated in the accompanying drawings and description. The illustrative examples may be implemented or incorporated in other aspects, variations, and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects, and/or examples.

The present disclosure is directed to a surgical visualization platform that leverages "digital surgery" to obtain additional information about a patient's anatomy and/or a surgical procedure. The surgical visualization platform is further configured to convey data and/or information to one or more clinicians in a helpful manner. For example, various aspects of the present disclosure provide improved visualization of the patient's anatomy and/or the surgical procedure.

"Digital surgery" can embrace robotic systems, advanced imaging, advanced instrumentation, artificial intelligence, machine learning, data analytics for performance tracking and benchmarking, connectivity both inside and outside of the operating room (OR), and more. Although various surgical visualization platforms described herein can be used in combination with a robotic surgical system, surgical visualization platforms are not limited to use with a robotic surgical system. In certain instances, advanced surgical visualization can occur without robotics and/or with limited and/or optional robotic assistance. Similarly, digital surgery can occur without robotics and/or with limited and/or optional robotic assistance.

In certain instances, a surgical system that incorporates a surgical visualization platform may enable smart dissection in order to identify and avoid critical structures. Critical structures include anatomical structures such as a ureter, an artery such as a superior mesenteric artery, a vein such as a portal vein, a nerve such as a phrenic nerve, and/or a tumor, among other anatomical structures. In other instances, a critical structure can be a foreign structure in the anatomical field, such as a surgical device, surgical fastener, clip, tack, bougie, band, and/or plate, for example. Critical structures can be determined on a patient-by-patient and/or a procedure-by-procedure basis. Example critical structures are further described herein. Smart dissection technology may provide improved intraoperative guidance for dissection and/or can enable smarter decisions with critical anatomy detection and avoidance technology, for example.

A surgical system incorporating a surgical visualization platform may also enable smart anastomosis technologies that provide more consistent anastomoses at optimal location(s) with improved workflow. Cancer localization technologies may also be improved with the various surgical visualization platforms and procedures described herein. For example, cancer localization technologies can identify and track a cancer location, orientation, and its margins. In certain instances, the cancer localizations technologies may compensate for movement of a tool, a patient, and/or the patient's anatomy during a surgical procedure in order to provide guidance back to the point of interest for the clinician.

In certain aspects of the present disclosure, a surgical visualization platform may provide improved tissue characterization and/or lymph node diagnostics and mapping. For example, tissue characterization technologies may characterize tissue type and health without the need for physical haptics, especially when dissecting and/or placing stapling devices within the tissue. Certain tissue characterization technologies described herein may be utilized without ionizing radiation and/or contrast agents. With respect to lymph node diagnostics and mapping, a surgical visualization platform may preoperatively locate, map, and ideally diagnose the lymph system and/or lymph nodes involved in cancerous diagnosis and staging, for example.

These and other related topics are described herein and/or in the aforementioned contemporaneously-filed U.S. Patent Applications, which are incorporated by reference herein in their respective entireties.

During a surgical procedure, the information available to the clinician via the "naked eye" and/or an imaging system may provide an incomplete view of the surgical site. For example, certain structures, such as structures embedded or buried within an organ, can be at least partially concealed or hidden from view. Additionally, certain dimensions and/or relative distances can be difficult to ascertain with existing sensor systems and/or difficult for the "naked eye" to perceive. Moreover, certain structures can move preoperatively (e.g. before a surgical procedure but after a preoperative scan) and/or intraoperatively. In such instances, the clinician can be unable to accurately determine the location of a critical structure intraoperatively.

When the position of a critical structure is uncertain and/or when the proximity between the critical structure and a surgical tool is unknown, a clinician's decision-making process can be inhibited. For example, a clinician may avoid certain areas in order to avoid inadvertent dissection of a critical structure; however, the avoided area may be unnecessarily large and/or at least partially misplaced. Due to uncertainty and/or overly/excessive exercises in caution, the clinician may not access certain desired regions. For example, excess caution may cause a clinician to leave a portion of a tumor and/or other undesirable tissue in an effort to avoid a critical structure even if the critical structure is not in the particular area and/or would not be negatively impacted by the clinician working in that particular area. In certain instances, surgical results can be improved with increased knowledge and/or certainty, which can allow a surgeon to be more accurate and, in certain instances, less conservative/more aggressive with respect to particular anatomical areas.

In various aspects, the present disclosure provides a surgical visualization system for intraoperative identification and avoidance of critical structures. In one aspect, the present disclosure provides a surgical visualization system that enables enhanced intraoperative decision making and improved surgical outcomes. In various aspects, the disclosed surgical visualization system provides advanced visualization capabilities beyond what a clinician sees with the "naked eye" and/or beyond what an imaging system can recognize and/or convey to the clinician. The various surgical visualization systems can augment and enhance what a clinician is able to know prior to tissue treatment (e.g. dissection) and, thus, may improve outcomes in various instances.

For example, a visualization system can include a first light emitter configured to emit a plurality of spectral waves, a second light emitter configured to emit a light pattern, and one or more receivers, or sensors, configured to detect visible light, molecular responses to the spectral waves (spectral imaging), and/or the light pattern. The surgical visualization system can also include an imaging system and a control circuit in signal communication with the receiver(s) and the imaging system. Based on output from the receiver(s), the control circuit can determine a geometric surface map, i.e. three-dimensional surface topography, of the visible surfaces at the surgical site and one or more distances with respect to the surgical site. In certain instances, the control circuit can determine one more distances to an at least partially concealed structure. Moreover, the imaging system can convey the geometric surface map and the one or more distances to a clinician. In such instances, an augmented view of the surgical site provided to the clinician can provide a representation of the concealed structure within the relevant context of the surgical site. For example, the imaging system can virtually augment the concealed structure on the geometric surface map of the concealing and/or obstructing tissue similar to a line drawn on the ground to indicate a utility line below the surface. Additionally or alternatively, the imaging system can convey the proximity of one or more surgical tools to the visible and obstructing tissue and/or to the at least partially concealed structure and/or the depth of the concealed structure below the visible surface of the obstructing tissue. For example, the visualization system can determine a distance with respect to the augmented line on the surface of the visible tissue and convey the distance to the imaging system.

In various aspects of the present disclosure, a surgical visualization system is disclosed for intraoperative identification and avoidance of critical structures. Such a surgical visualization system can provide valuable information to a clinician during a surgical procedure. As a result, the clinician can confidently maintain momentum throughout the surgical procedure knowing that the surgical visualization system is tracking a critical structure such as a ureter, specific nerves, and/or critical blood vessels, for example, which may be approached during dissection, for example. In one aspect, the surgical visualization system can provide an indication to the clinician in sufficient time for the clinician to pause and/or slow down the surgical procedure and evaluate the proximity to the critical structure to prevent inadvertent damage thereto. The surgical visualization system can provide an ideal, optimized, and/or customizable amount of information to the clinician to allow the clinician to move confidently and/or quickly through tissue while avoiding inadvertent damage to healthy tissue and/or critical structure(s) and, thus, to minimize the risk of harm resulting from the surgical procedure.

Figure 1:
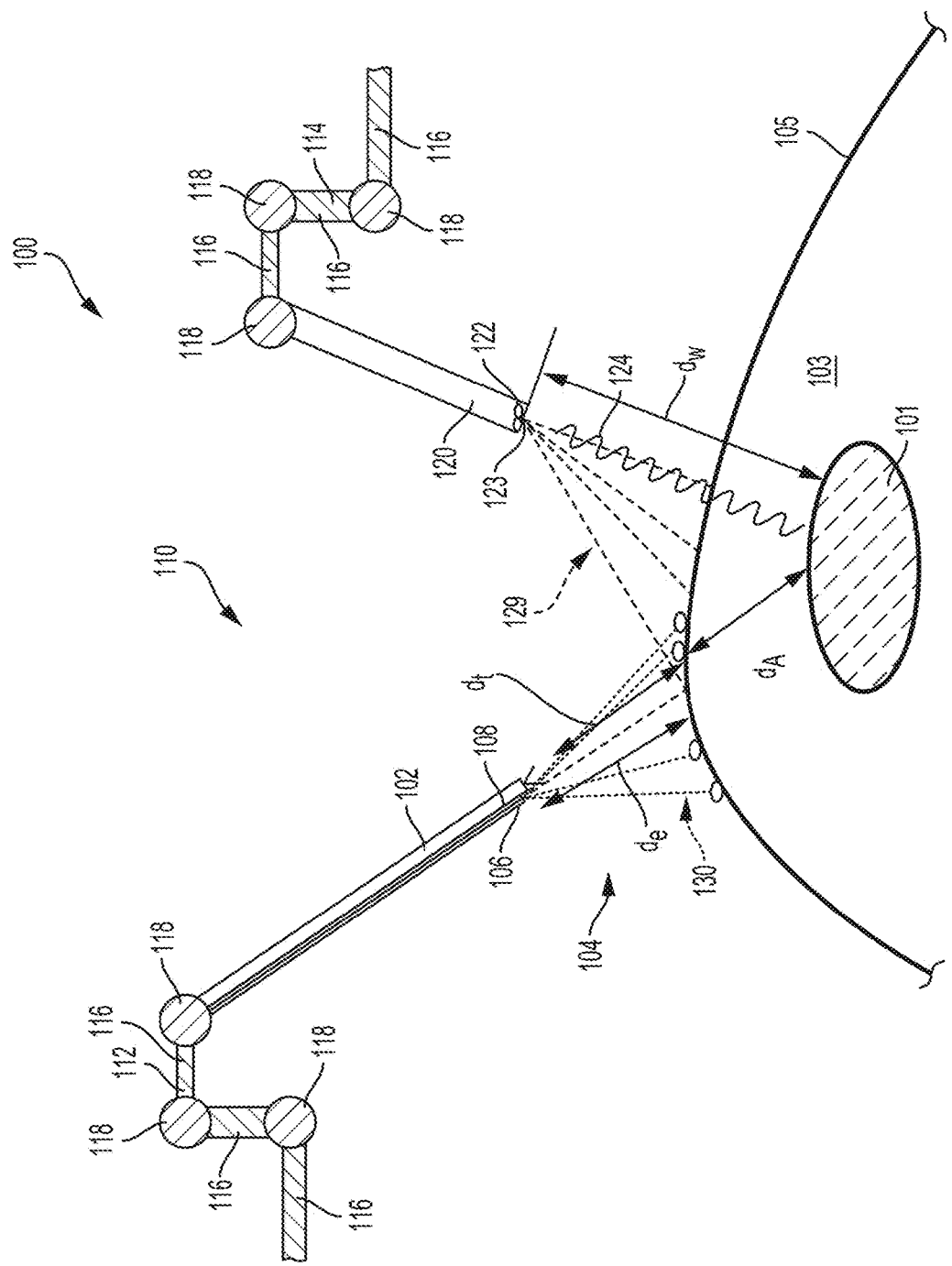
FIG. 1 is a schematic of a surgical visualization system including an imaging device and a surgical device, the surgical visualization system configured to identify a critical structure below a tissue surface, according to at least one aspect of the present disclosure.

FIG. 1 is a schematic of a surgical visualization system 100 according to at least one aspect of the present disclosure. The surgical visualization system 100 can create a visual representation of a critical structure 101 within an anatomical field. The surgical visualization system 100 can be used for clinical analysis and/or medical intervention, for example. In certain instances, the surgical visualization system 100 can be used intraoperatively to provide real-time, or near real-time, information to the clinician regarding proximity data, dimensions, and/or distances during a surgical procedure. The surgical visualization system 100 is configured for intraoperative identification of critical structure(s) and/or to facilitate the avoidance of the critical structure(s) 101 by a surgical device. For example, by identifying the critical structure 101, a clinician can avoid maneuvering a surgical device around the critical structure 101 and/or a region in a predefined proximity of the critical structure 101 during a surgical procedure. The clinician can avoid dissection of and/or near a vein, artery, nerve, and/or vessel, for example, identified as the critical structure 101, for example. In various instances, the critical structure 101 can be determined on a patient-by-patient and/or a procedure-by-procedure basis.

The surgical visualization system 100 incorporates tissue identification and geometric surface mapping in combination with a distance sensor system 104. In combination, these features of the surgical visualization system 100 can determine a position of a critical structure 101 within the anatomical field and/or the proximity of a surgical device 102 to the surface 105 of the visible tissue and/or to the critical structure 101. Moreover, the surgical visualization system 100 includes an imaging system that includes an imaging device 120, such as a camera, for example, configured to provide real-time views of the surgical site. In various instances, the imaging device 120 is a spectral camera (e.g. a hyperspectral camera, multispectral camera, or selective spectral camera), which is configured to detect reflected spectral waveforms and generate a spectral cube of images based on the molecular response to the different wavelengths. Views from the imaging device 120 can be provided to a clinician and, in various aspects of the present disclosure, can be augmented with additional information based on the tissue identification, landscape mapping, and the distance sensor system 104. In such instances, the surgical visualization system 100 includes a plurality of subsystems—an imaging subsystem, a surface mapping subsystem, a tissue identification subsystem, and/or a distance determining subsystem. These subsystems can cooperate to intraoperatively provide advanced data synthesis and integrated information to the clinician(s).

The imaging device can include a camera or imaging sensor that is configured to detect visible light, spectral light waves (visible or invisible), and a structured light pattern (visible or invisible), for example. In various aspects of the present disclosure, the imaging system can include an imaging device such as an endoscope, for example. Additionally or alternatively, the imaging system can include an imaging device such as an arthroscope, angioscope, bronchoscope, choledochoscope, colonoscope, cytoscope, duodenoscope, enteroscope, esophagogastro-duodenoscope (gastroscope), laryngoscope, nasopharyngo-neproscope, sigmoidoscope, thoracoscope, ureteroscope, or exoscope, for example. In other instances, such as in open surgery applications, the imaging system may not include a scope.

In various aspects of the present disclosure, the tissue identification subsystem can be achieved with a spectral imaging system. The spectral imaging system can rely on hyperspectral imaging, multispectral imaging, or selective spectral imaging, for example. Hyperspectral imaging of tissue is further described in U.S. Pat. No. 9,274,047, titled SYSTEM AND METHOD FOR GROSS ANATOMIC PATHOLOGY USING HYPERSPECTRAL IMAGING, issued Mar. 1, 2016, which is incorporated by reference herein in its entirety.

In various aspect of the present disclosure, the surface mapping subsystem can be achieved with a light pattern system, as further described herein. The use of a light pattern (or structured light) for surface mapping is known. Known surface mapping techniques can be utilized in the surgical visualization systems described herein.

Structured light is the process of projecting a known pattern (often a grid or horizontal bars) on to a surface. U.S. Patent Application Publication No. 2017/0055819, titled SET COMPRISING A SURGICAL INSTRUMENT, published Mar. 2, 2017, and U.S. Patent Application Publication No. 2017/0251900, titled DEPICTION SYSTEM, published Sep. 7, 2017, disclose a surgical system comprising a light source and a projector for projecting a light pattern. U.S. Patent Application Publication No. 2017/0055819, titled SET COMPRISING A SURGICAL INSTRUMENT, published Mar. 2, 2017, and U.S. Patent Application Publication No. 2017/0251900, titled DEPICTION SYSTEM, published Sep. 7, 2017, are incorporated by reference herein in their respective entireties.

In various aspects of the present disclosure, the distance determining system can be incorporated into the surface mapping system. For example, structured light can be utilized to generate a three-dimensional virtual model of the visible surface and determine various distances with respect to the visible surface. Additionally or alternatively, the distance determining system can rely on time-of-flight measurements to determine one or more distances to the identified tissue (or other structures) at the surgical site.

Figure 2:
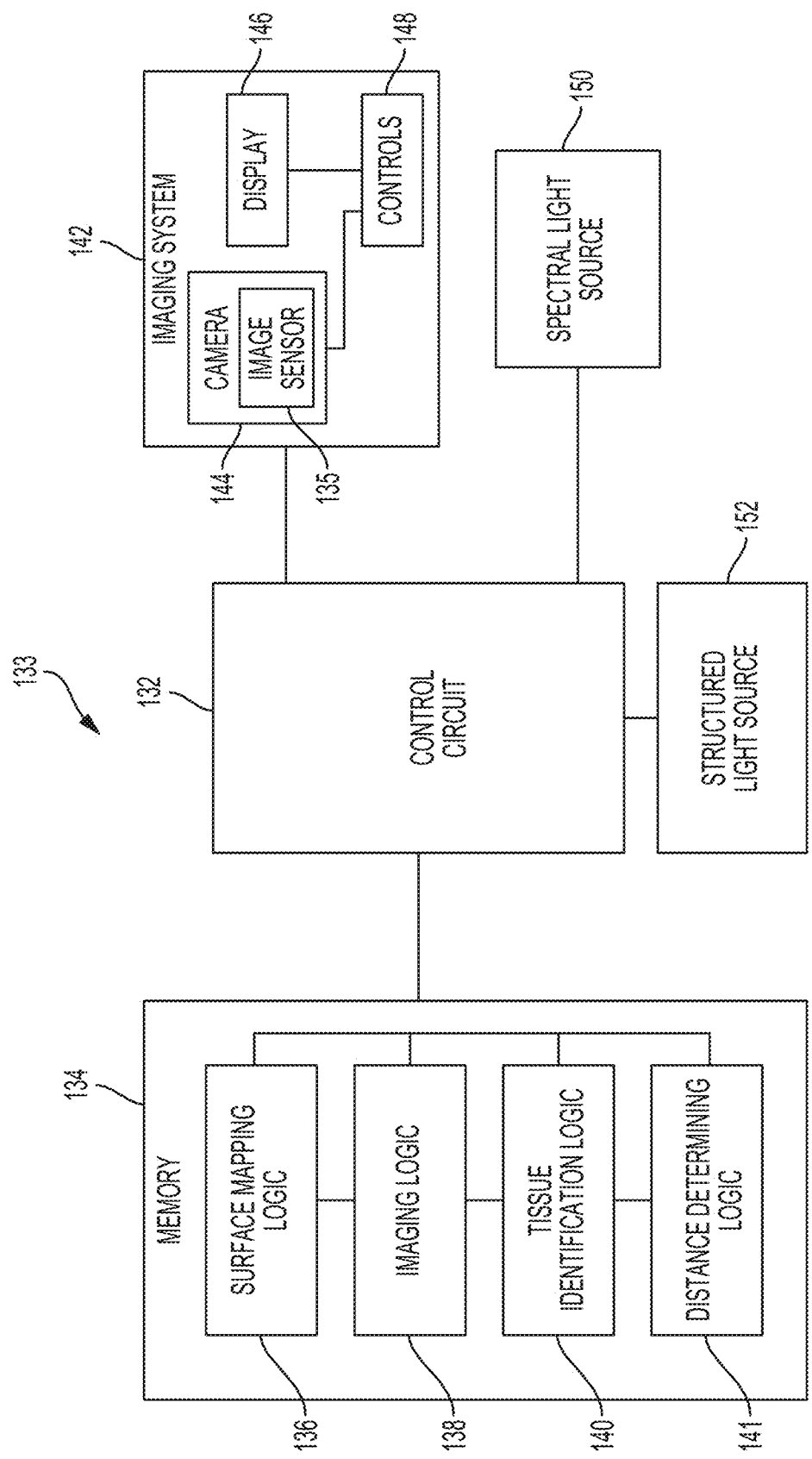
FIG. 2 is a schematic of a control system for a surgical visualization system, according to at least one aspect of the present disclosure.

FIG. 2 is a schematic diagram of a control system 133, which can be utilized with the surgical visualization system 100. The control system 133 includes a control circuit 132 in signal communication with a memory 134. The memory 134 stores instructions executable by the control circuit 132 to determine and/or recognize critical structures (e.g. the critical structure 101 in FIG. 1), determine and/or compute one or more distances and/or three-dimensional digital representations, and to communicate certain information to one or more clinicians. For example, the memory 134 stores surface mapping logic 136, imaging logic 138, tissue identification logic 140, or distance determining logic 141 or any combinations of the logic 136, 138, 140, and 141. The control system 133 also includes an imaging system 142 having one or more cameras 144 (like the imaging device 120 in FIG. 1), one or more displays 146, or one or more controls 148 or any combinations of these elements. The camera 144 can include one or more image sensors 135 to receive signals from various light sources emitting light at various visible and invisible spectra (e.g. visible light, spectral imagers, three-dimensional lens, among others). The display 146 can include one or more screens or monitors for depicting real, virtual, and/or virtually-augmented images and/or information to one or more clinicians.

In various aspects, the heart of the camera 144 is the image sensor 135. Generally, modern image sensors 135 are solid-state electronic devices containing up to millions of discrete photodetector sites called pixels. The image sensor 135 technology falls into one of two categories: Charge-Coupled Device (CCD) and Complementary Metal Oxide Semiconductor (CMOS) imagers and more recently, short-wave infrared (SWIR) is an emerging technology in imaging. Another type of image sensor 135 employs a hybrid CCD/CMOS architecture (sold under the name "sCMOS") and consists of CMOS readout integrated circuits (ROICs) that are bump bonded to a CCD imaging substrate. CCD and CMOS image sensors 135 are sensitive to wavelengths from approximately 350-1050 nm, although the range is usually given from 400-1000 nm. CMOS sensors are, in general, more sensitive to IR wavelengths than CCD sensors. Solid state image sensors 135 are based on the photoelectric effect and, as a result, cannot distinguish between colors. Accordingly, there are two types of color CCD cameras: single chip and three-chip. Single chip color CCD cameras offer a common, low-cost imaging solution and use a mosaic (e.g. Bayer) optical filter to separate incoming light into a series of colors and employ an interpolation algorithm to resolve full color images. Each color is, then, directed to a different set of pixels. Three-chip color CCD cameras provide higher resolution by employing a prism to direct each section of the incident spectrum to a different chip. More accurate color reproduction is possible, as each point in space of the object has separate RGB intensity values, rather than using an algorithm to determine the color. Three-chip cameras offer extremely high resolutions.

The control system 133 also includes a spectral light source 150 and a structured light source 152. In certain instances, a single source can be pulsed to emit wavelengths of light in the spectral light source 150 range and wavelengths of light in the structured light source 152 range. Alternatively, a single light source can be pulsed to provide light in the invisible spectrum (e.g. infrared spectral light) and wavelengths of light on the visible spectrum. The spectral light source 150 can be a hyperspectral light source, a multispectral light source, and/or a selective spectral light source, for example. In various instances, the tissue identification logic 140 can identify critical structure(s) via data from the spectral light source 150 received by the image sensor 135 portion of the camera 144. The surface mapping logic 136 can determine the surface contours of the visible tissue based on reflected structured light. With time-of-flight measurements, the distance determining logic 141 can determine one or more distance(s) to the visible tissue and/or the critical structure 101. One or more outputs from the surface mapping logic 136, the tissue identification logic 140, and the distance determining logic 141, can be provided to the imaging logic 138, and combined, blended, and/or overlaid to be conveyed to a clinician via the display 146 of the imaging system 142.

Figure 2A:
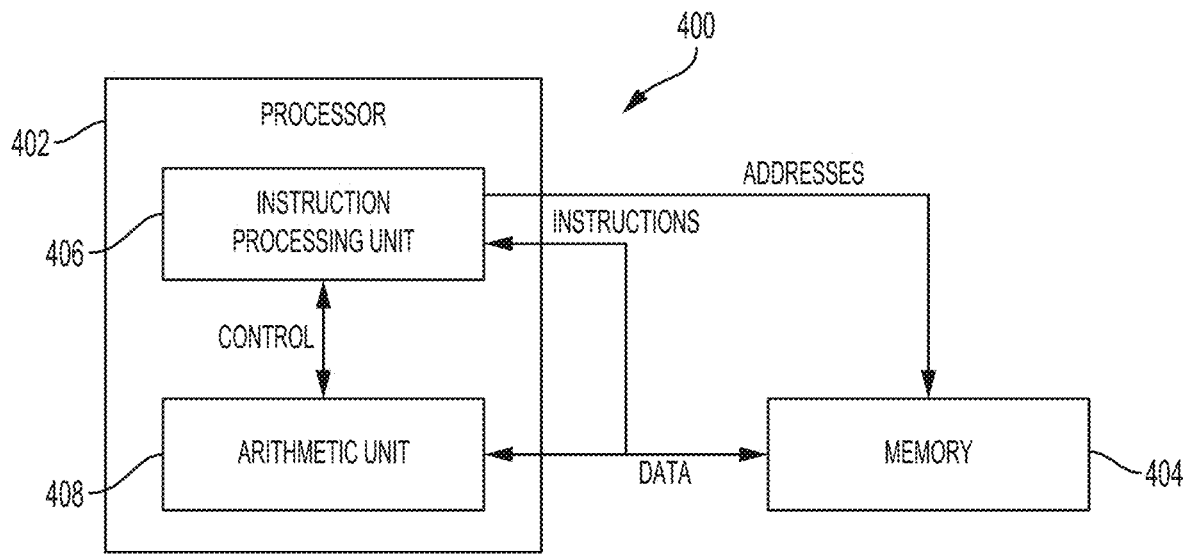
FIG. 2A illustrates a control circuit configured to control aspects of a surgical visualization system, according to at least one aspect of the present disclosure.
Figure 2B:
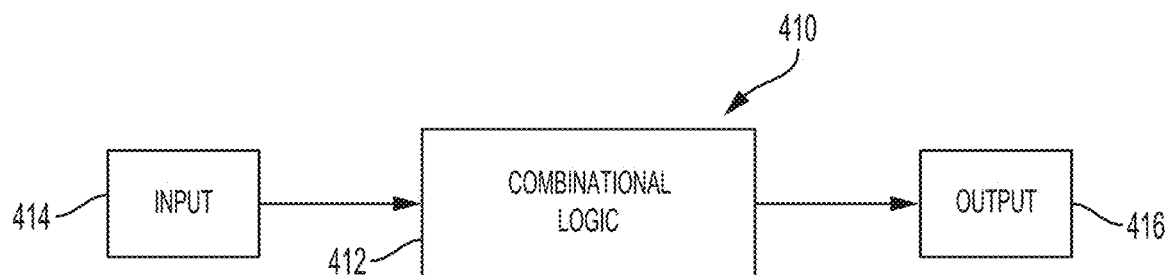
FIG. 2B illustrates a combinational logic circuit configured to control aspects of a surgical visualization system, according to at least one aspect of the present disclosure.
Figure 2C:
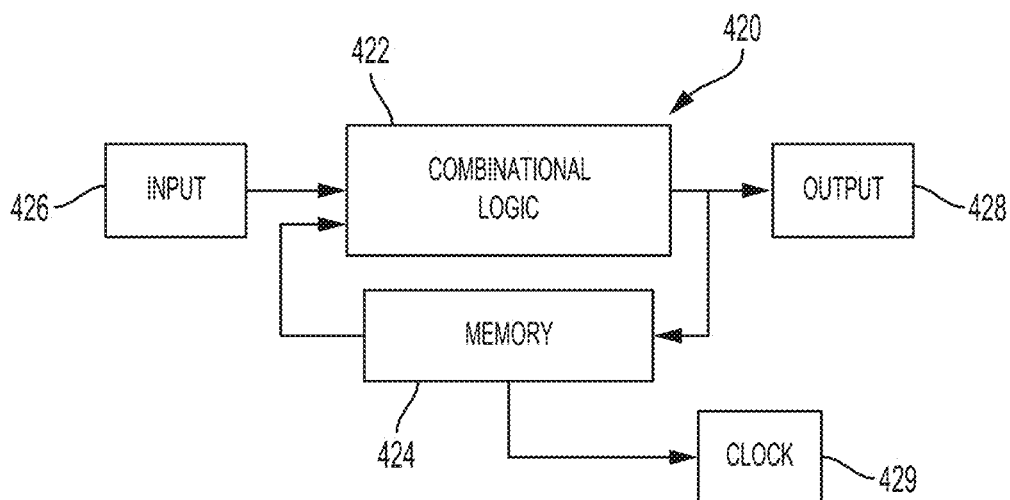
FIG. 2C illustrates a sequential logic circuit configured to control aspects of a surgical visualization system, according to at least one aspect of the present disclosure.

The description now turns briefly to FIGS. 2A-2C to describe various aspects of the control circuit 132 for controlling various aspects of the surgical visualization system 100. Turning to FIG. 2A, there is illustrated a control circuit 400 configured to control aspects of the surgical visualization system 100, according to at least one aspect of this disclosure. The control circuit 400 can be configured to implement various processes described herein. The control circuit 400 may comprise a microcontroller comprising one or more processors 402 (e.g., microprocessor, microcontroller) coupled to at least one memory circuit 404. The memory circuit 404 stores machine-executable instructions that, when executed by the processor 402, cause the processor 402 to execute machine instructions to implement various processes described herein. The processor 402 may be any one of a number of single-core or multicore processors known in the art. The memory circuit 404 may comprise volatile and non-volatile storage media. The processor 402 may include an instruction processing unit 406 and an arithmetic unit 408. The instruction processing unit may be configured to receive instructions from the memory circuit 404 of this disclosure.

FIG. 2B illustrates a combinational logic circuit 410 configured to control aspects of the surgical visualization system 100, according to at least one aspect of this disclosure. The combinational logic circuit 410 can be configured to implement various processes described herein. The combinational logic circuit 410 may comprise a finite state machine comprising a combinational logic 412 configured to receive data associated with the surgical instrument or tool at an input 414, process the data by the combinational logic 412, and provide an output 416.

FIG. 2C illustrates a sequential logic circuit 420 configured to control aspects of the surgical visualization system 100, according to at least one aspect of this disclosure. The sequential logic circuit 420 or the combinational logic 422 can be configured to implement various processes described herein. The sequential logic circuit 420 may comprise a finite state machine. The sequential logic circuit 420 may comprise a combinational logic 422, at least one memory circuit 424, and a circuit 424, for example. The at least one memory circuit 424 can store a current state of the finite state machine. In certain instances, the sequential logic circuit 420 may be synchronous or asynchronous. The combinational logic 422 is configured to receive data associated with a surgical device or system from an input 426, process the data by the combinational logic 422, and provide an output 428. In other aspects, the circuit may comprise a combination of a processor (e.g., processor 402 in FIG. 2A) and a finite state machine to implement various processes herein. In other aspects, the finite state machine may comprise a combination of a combinational logic circuit (e.g., combinational logic circuit 410, FIG. 2B) and the sequential logic circuit 420.

Referring again to the surgical visualization system 100 in FIG. 1, the critical structure 101 can be an anatomical structure of interest. For example, the critical structure 101 can be a ureter, an artery such as a superior mesenteric artery, a vein such as a portal vein, a nerve such as a phrenic nerve, and/or a tumor, among other anatomical structures. In other instances, the critical structure 101 can be a foreign structure in the anatomical field, such as a surgical device, surgical fastener, clip, tack, bougie, band, and/or plate, for example. Example critical structures are further described herein and in the aforementioned contemporaneously-filed U.S. Patent Applications, including U.S. patent application Ser. No. 16/128,192, titled VISUALIZATION OF SURGICAL DEVICES, now U.S. Patent Application Publication No. 2020/0015905, for example, which are incorporated by reference herein in their respective entireties.

In one aspect, the critical structure 101 may be embedded in tissue 103. Stated differently, the critical structure 101 may be positioned below the surface 105 of the tissue 103. In such instances, the tissue 103 conceals the critical structure 101 from the clinician's view. The critical structure 101 is also obscured from the view of the imaging device 120 by the tissue 103. The tissue 103 can be fat, connective tissue, adhesions, and/or organs, for example. In other instances, the critical structure 101 can be partially obscured from view.

FIG. 1 also depicts the surgical device 102. The surgical device 102 includes an end effector having opposing jaws extending from the distal end of the shaft of the surgical device 102. The surgical device 102 can be any suitable surgical device such as, for example, a dissector, a stapler, a grasper, a clip applier, and/or an energy device including mono-polar probes, bi-polar probes, ablation probes, and/or an ultrasonic end effector. Additionally or alternatively, the surgical device 102 can include another imaging or diagnostic modality, such as an ultrasound device, for example. In one aspect of the present disclosure, the surgical visualization system 100 can be configured to achieve identification of one or more critical structures 101 and the proximity of the surgical device 102 to the critical structure(s) 101.

The imaging device 120 of the surgical visualization system 100 is configured to detect light at various wavelengths, such as, for example, visible light, spectral light waves (visible or invisible), and a structured light pattern (visible or invisible). The imaging device 120 may include a plurality of lenses, sensors, and/or receivers for detecting the different signals. For example, the imaging device 120 can be a hyperspectral, multispectral, or selective spectral camera, as further described herein. The imaging device 120 can also include a waveform sensor 122 (such as a spectral image sensor, detector, and/or three-dimensional camera lens). For example, the imaging device 120 can include a right-side lens and a left-side lens used together to record two two-dimensional images at the same time and, thus, generate a three-dimensional image of the surgical site, render a three-dimensional image of the surgical site, and/or determine one or more distances at the surgical site. Additionally or alternatively, the imaging device 120 can be configured to receive images indicative of the topography of the visible tissue and the identification and position of hidden critical structures, as further described herein. For example, the field of view of the imaging device 120 can overlap with a pattern of light (structured light) on the surface 105 of the tissue, as shown in FIG. 1.

In one aspect, the surgical visualization system 100 may be incorporated into a robotic system 110. For example, the robotic system 110 may include a first robotic arm 112 and a second robotic arm 114. The robotic arms 112, 114 include rigid structural members 116 and joints 118, which can include servomotor controls. The first robotic arm 112 is configured to maneuver the surgical device 102, and the second robotic arm 114 is configured to maneuver the imaging device 120. A robotic control unit can be configured to issue control motions to the robotic arms 112, 114, which can affect the surgical device 102 and the imaging device 120, for example.

The surgical visualization system 100 also includes an emitter 106, which is configured to emit a pattern of light, such as stripes, grid lines, and/or dots, to enable the determination of the topography or landscape of the surface 105. For example, projected light arrays 130 can be used for three-dimensional scanning and registration on the surface 105. The projected light arrays 130 can be emitted from the emitter 106 located on the surgical device 102 and/or one of the robotic arms 112, 114 and/or the imaging device 120, for example. In one aspect, the projected light array 130 is employed to determine the shape defined by the surface 105 of the tissue 103 and/or the motion of the surface 105 intraoperatively. The imaging device 120 is configured to detect the projected light arrays 130 reflected from the surface 105 to determine the topography of the surface 105 and various distances with respect to the surface 105.

In one aspect, the imaging device 120 also may include an optical waveform emitter 123 that is configured to emit electromagnetic radiation 124 (NIR photons) that can penetrate the surface 105 of the tissue 103 and reach the critical structure 101. The imaging device 120 and the optical waveform emitter 123 thereon can be positionable by the robotic arm 114. A corresponding waveform sensor 122 (an image sensor, spectrometer, or vibrational sensor, for example) on the imaging device 120 is configured to detect the effect of the electromagnetic radiation received by the waveform sensor 122. The wavelengths of the electromagnetic radiation 124 emitted by the optical waveform emitter 123 can be configured to enable the identification of the type of anatomical and/or physical structure, such as the critical structure 101. The identification of the critical structure 101 can be accomplished through spectral analysis, photo-acoustics, and/or ultrasound, for example. In one aspect, the wavelengths of the electromagnetic radiation 124 may be variable. The waveform sensor 122 and optical waveform emitter 123 may be inclusive of a multispectral imaging system and/or a selective spectral imaging system, for example. In other instances, the waveform sensor 122 and optical waveform emitter 123 may be inclusive of a photoacoustic imaging system, for example. In other instances, the optical waveform emitter 123 can be positioned on a separate surgical device from the imaging device 120.

The surgical visualization system 100 also may include the distance sensor system 104 configured to determine one or more distances at the surgical site. In one aspect, the time-of-flight distance sensor system 104 may be a time-of-flight distance sensor system that includes an emitter, such as the emitter 106, and a receiver 108, which can be positioned on the surgical device 102. In other instances, the time-of-flight emitter can be separate from the structured light emitter. In one general aspect, the emitter 106 portion of the time-of-flight distance sensor system 104 may include a very tiny laser source and the receiver 108 portion of the time-of-flight distance sensor system 104 may include a matching sensor. The time-of-flight distance sensor system 104 can detect the "time of flight," or how long the laser light emitted by the emitter 106 has taken to bounce back to the sensor portion of the receiver 108. Use of a very narrow light source in the emitter 106 enables the distance sensor system 104 to determining the distance to the surface 105 of the tissue 103 directly in front of the distance sensor system 104. Referring still to FIG. 1, $d_e$ is the emitter-to-tissue distance from the emitter 106 to the surface 105 of the tissue 103 and $d_t$ is the device-to-tissue distance from the distal end of the surgical device 102 to the surface 105 of the tissue. The distance sensor system 104 can be employed to determine the emitter-to-tissue distance $d_e$. The device-to-tissue distance $d_t$ is obtainable from the known position of the emitter 106 on the shaft of the surgical device 102 relative to the distal end of the surgical device 102. In other words, when the distance between the emitter 106 and the distal end of the surgical device 102 is known, the device-to-tissue distance $d_t$ can be determined from the emitter-to-tissue distance $d_e$. In certain instances, the shaft of the surgical device 102 can include one or more articulation joints, and can be articulatable with respect to the emitter 106 and the jaws. The articulation configuration can include a multi-joint vertebrae-like structure, for example. In certain instances, a three-dimensional camera can be utilized to triangulate one or more distances to the surface 105.

In various instances, the receiver 108 for the time-of-flight distance sensor system 104 can be mounted on a separate surgical device instead of the surgical device 102. For example, the receiver 108 can be mounted on a cannula or trocar through which the surgical device 102 extends to reach the surgical site. In still other instances, the receiver 108 for the time-of-flight distance sensor system 104 can be mounted on a separate robotically-controlled arm (e.g. the robotic arm 114), on a movable arm that is operated by another robot, and/or to an operating room (OR) table or fixture. In certain instances, the imaging device 120 includes the time-of-flight receiver 108 to determine the distance from the emitter 106 to the surface 105 of the tissue 103 using a line between the emitter 106 on the surgical device 102 and the imaging device 120. For example, the distance $d_e$ can be triangulated based on known positions of the emitter 106 (on the surgical device 102) and the receiver 108 (on the imaging device 120) of the time-of-flight distance sensor system 104. The three-dimensional position of the receiver 108 can be known and/or registered to the robot coordinate plane intraoperatively.

In certain instances, the position of the emitter 106 of the time-of-flight distance sensor system 104 can be controlled by the first robotic arm 112 and the position of the receiver 108 of the time-of-flight distance sensor system 104 can be controlled by the second robotic arm 114. In other instances, the surgical visualization system 100 can be utilized apart from a robotic system. In such instances, the distance sensor system 104 can be independent of the robotic system.

In certain instances, one or more of the robotic arms 112, 114 may be separate from a main robotic system used in the surgical procedure. At least one of the robotic arms 112, 114 can be positioned and registered to a particular coordinate system without a servomotor control. For example, a closed-loop control system and/or a plurality of sensors for the robotic arms 110 can control and/or register the position of the robotic arm(s) 112, 114 relative to the particular coordinate system. Similarly, the position of the surgical device 102 and the imaging device 120 can be registered relative to a particular coordinate system.

Figure 3:
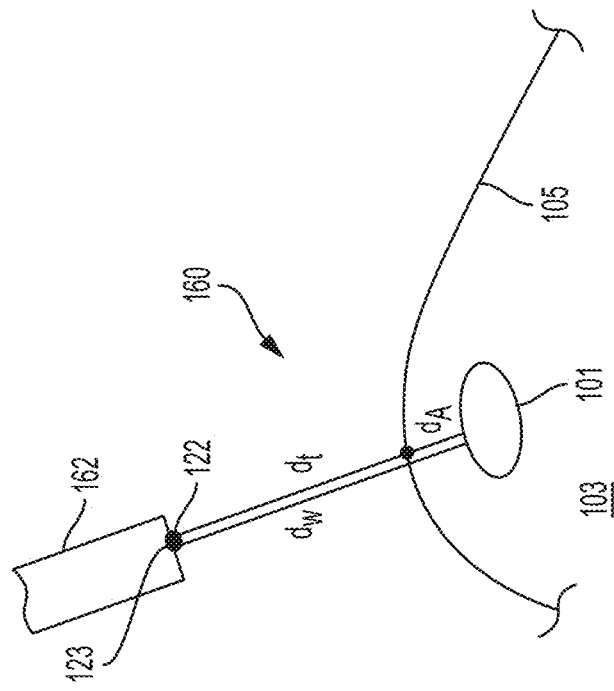
FIG. 3 is a schematic depicting triangularization between the surgical device, the imaging device, and the critical structure of FIG. 1 to determine a depth $d_A$ of the critical structure below the tissue surface, according to at least one aspect of the present disclosure.

Referring still to FIG. 1, $d_w$ is the camera-to-critical structure distance from the optical waveform emitter 123 located on the imaging device 120 to the surface of the critical structure 101, and $d_A$ is the depth of the critical structure 101 below the surface 105 of the tissue 103 (i.e., the distance between the portion of the surface 105 closest to the surgical device 102 and the critical structure 101). In various aspects, the time-of-flight of the optical waveforms emitted from the optical waveform emitter 123 located on the imaging device 120 can be configured to determine the camera-to-critical structure distance $d_w$. The use of spectral imaging in combination with time-of-flight sensors is further described herein. Moreover, referring now to FIG. 3, in various aspects of the present disclosure, the depth $d_A$ of the critical structure 101 relative to the surface 105 of the tissue 103 can be determined by triangulating from the distance $d_w$ and known positions of the emitter 106 on the surgical device 102 and the optical waveform emitter 123 on the imaging device 120 (and, thus, the known distance $d_x$ therebetween) to determine the distance $d_y$, which is the sum of the distances $d_e$ and $d_A$.

Additionally or alternatively, time-of-flight from the optical waveform emitter 123 can be configured to determine the distance from the optical waveform emitter 123 to the surface 105 of the tissue 103. For example, a first waveform (or range of waveforms) can be utilized to determine the camera-to-critical structure distance $d_w$ and a second waveform (or range of waveforms) can be utilized to determine the distance to the surface 105 of the tissue 103. In such instances, the different waveforms can be utilized to determine the depth of the critical structure 101 below the surface 105 of the tissue 103.

Additionally or alternatively, in certain instances, the distance $d_A$ can be determined from an ultrasound, a registered magnetic resonance imaging (MRI) or computerized tomography (CT) scan. In still other instances, the distance $d_A$ can be determined with spectral imaging because the detection signal received by the imaging device can vary based on the type of material. For example, fat can decrease the detection signal in a first way, or a first amount, and collagen can decrease the detection signal in a different, second way, or a second amount.

Figure 4:
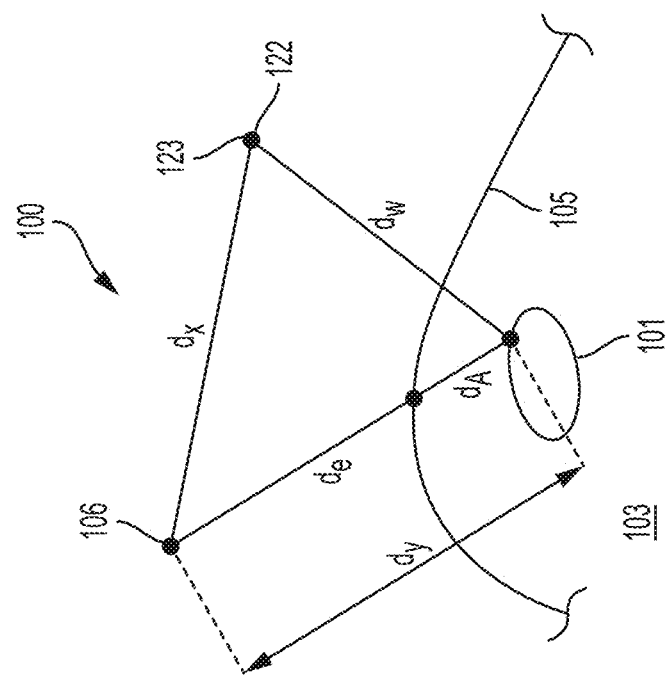
FIG. 4 is a schematic of a surgical visualization system configured to identify a critical structure below a tissue surface, wherein the surgical visualization system includes a pulsed light source for determining a depth $d_A$ of the critical structure below the tissue surface, according to at least one aspect of the present disclosure.

Referring now to a surgical visualization system 160 in FIG. 4, in which a surgical device 162 includes the optical waveform emitter 123 and the waveform sensor 122 that is configured to detect the reflected waveforms. The optical waveform emitter 123 can be configured to emit waveforms for determining the distances $d_t$ and $d_w$ from a common device, such as the surgical device 162, as further described herein. In such instances, the distance $d_A$ from the surface 105 of the tissue 103 to the surface of the critical structure 101 can be determined as follows:

$$d_A = d_w - d_t.$$

As disclosed herein, various information regarding visible tissue, embedded critical structures, and surgical devices can be determined by utilizing a combination approach that incorporates one or more time-of-flight distance sensors, spectral imaging, and/or structured light arrays in combination with an image sensor configured to detect the spectral wavelengths and the structured light arrays. Moreover, the image sensor can be configured to receive visible light and, thus, provide images of the surgical site to an imaging system. Logic or algorithms are employed to discern the information received from the time-of-flight sensors, spectral wavelengths, structured light, and visible light and render three-dimensional images of the surface tissue and underlying anatomical structures. In various instances, the imaging device 120 can include multiple image sensors.

Figure 6:
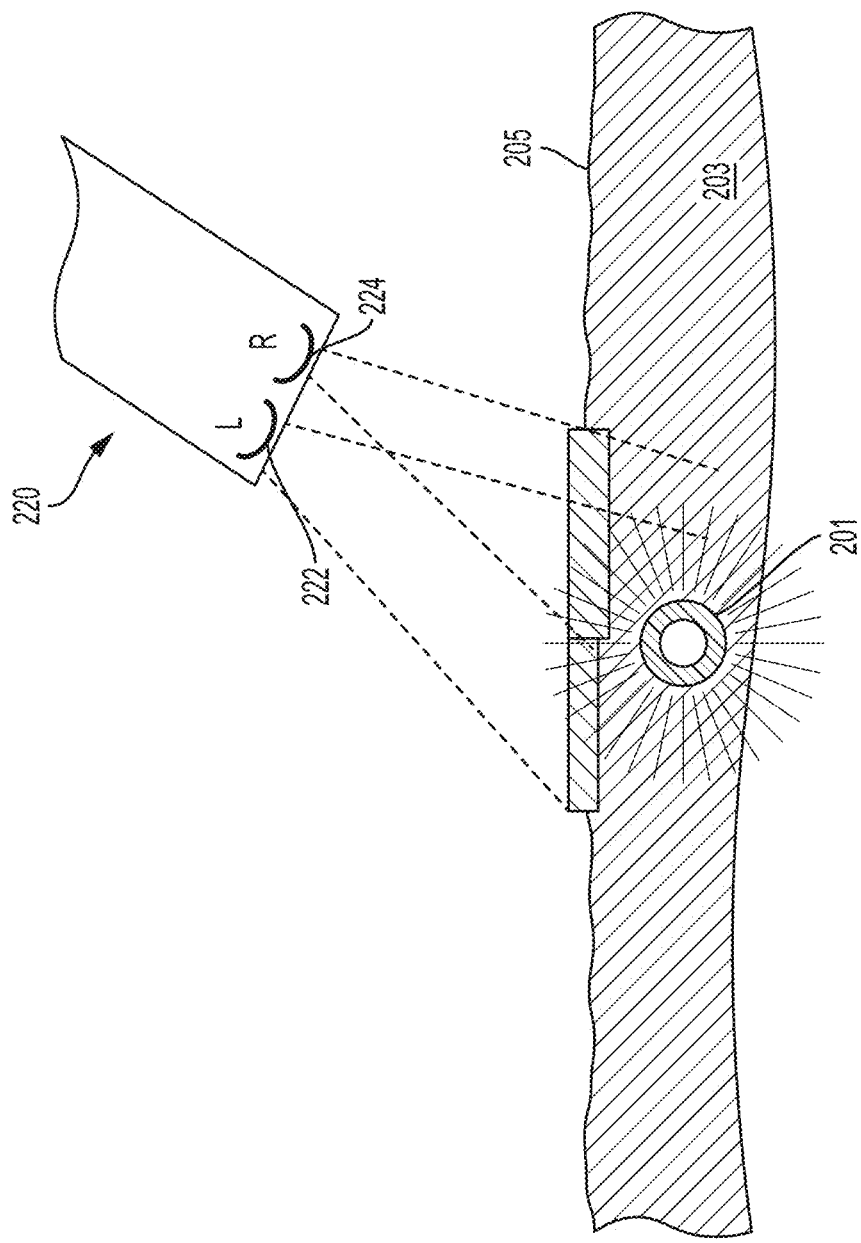
FIG. 6 is a schematic of a surgical visualization system including a three-dimensional camera, wherein the surgical visualization system is configured to identify a critical structure that is embedded within tissue, according to at least one aspect of the present disclosure.
Figures 7A, 7B:
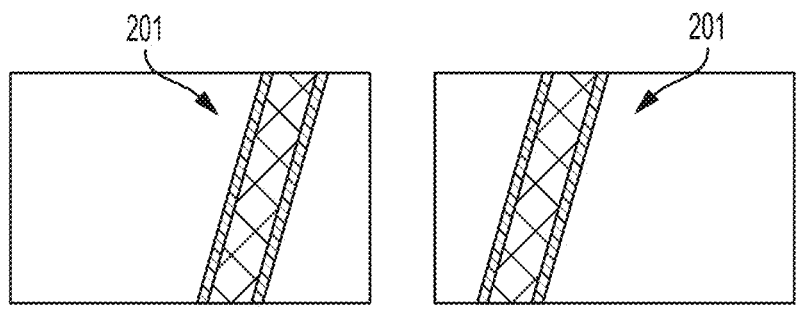
Figure 8:
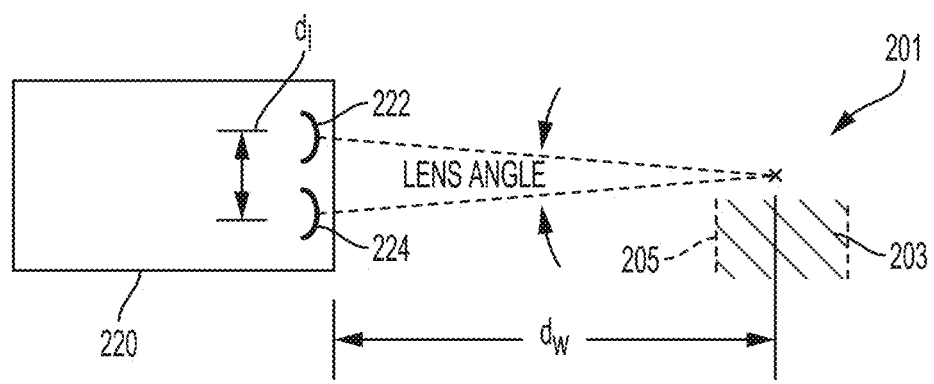
FIG. 8 is a schematic of the surgical visualization system of FIG. 6, in which a camera-to-critical structure distance $d_w$ from the three-dimensional camera to the critical structure can be determined, according to at least one aspect of the present disclosure.

The camera-to-critical structure distance $d_w$ can also be detected in one or more alternative ways. In one aspect, a fluoroscopy visualization technology, such as fluorescent indosciedine green (ICG), for example, can be utilized to illuminate a critical structure 201, as shown in FIGS. 6-8. A camera 220 can include two optical waveforms sensors 222, 224, which take simultaneous left-side and right-side images of the critical structure 201 (FIGS. 7A and 7B). In such instances, the camera 220 can depict a glow of the critical structure 201 below the surface 205 of the tissue 203, and the distance $d_w$ can be determined by the known distance between the sensors 222 and 224. In certain instances, distances can be determined more accurately by utilizing more than one camera or by moving a camera between multiple locations. In certain aspects, one camera can be controlled by a first robotic arm and a second camera by another robotic arm. In such a robotic system, one camera can be a follower camera on a follower arm, for example. The follower arm, and camera thereon, can be programmed to track the other camera and to maintain a particular distance and/or lens angle, for example.

Figure 9:
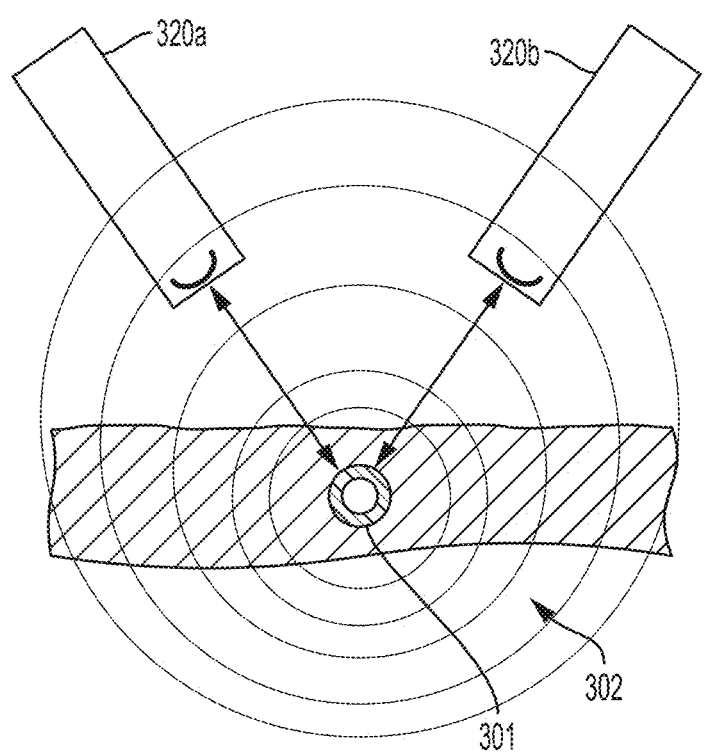
FIG. 9 is a schematic of a surgical visualization system utilizing two cameras to determine the position of an embedded critical structure, according to at least one aspect of the present disclosure.

In still other aspects, the surgical visualization system 100 may employ two separate waveform receivers (i.e. cameras/image sensors) to determine $d_w$. Referring now to FIG. 9, if a critical structure 301 or the contents thereof (e.g. a vessel or the contents of the vessel) can emit a signal 302, such as with fluoroscopy, then the actual location can be triangulated from two separate cameras 320a, 320b at known locations.

Figure 10B:
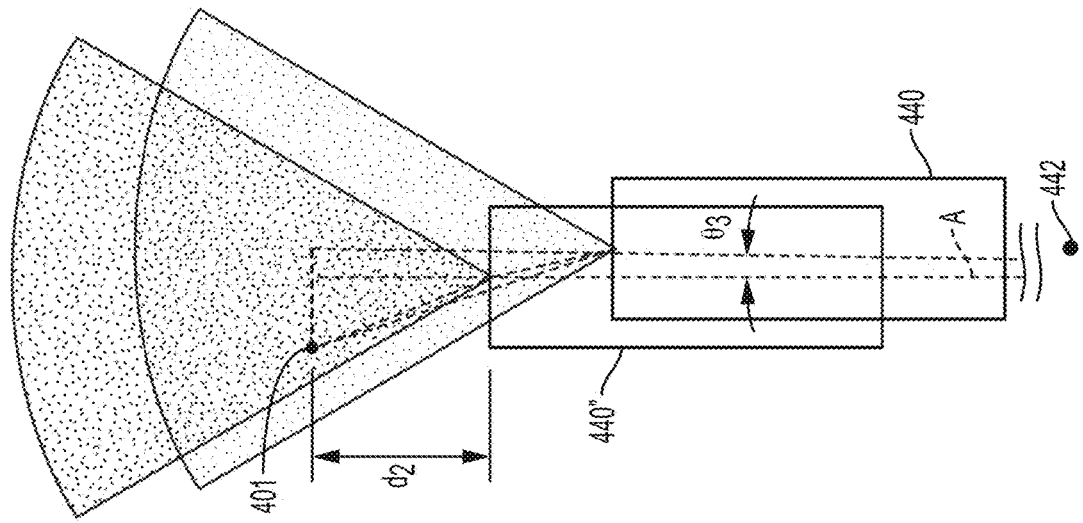
FIG. 10B is a schematic of the surgical visualization system of FIG. 10A, in which the camera is moved axially and rotationally between a plurality of known positions to determine a position of the embedded critical structure, according to at least one aspect of the present disclosure.
Figure 10A:
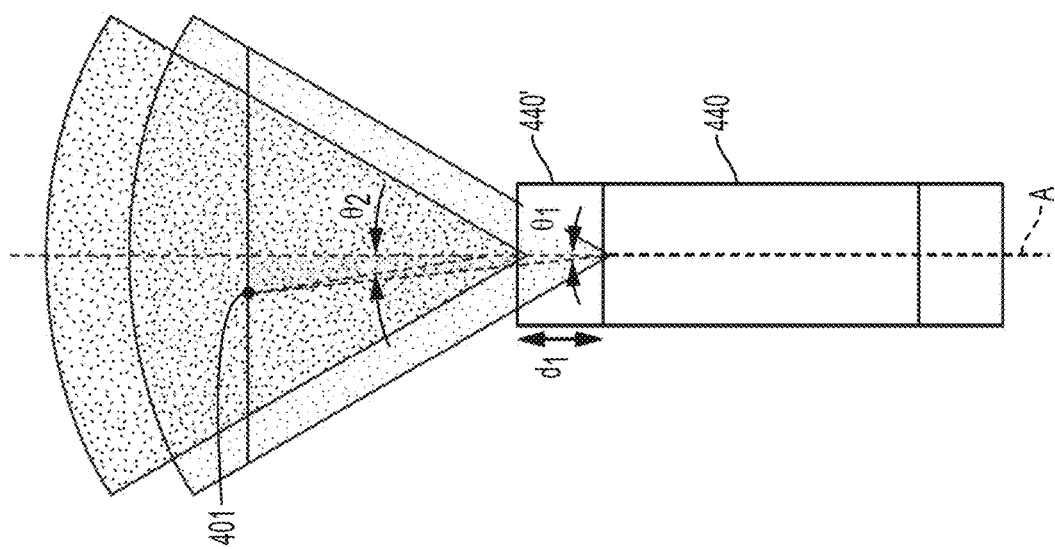
FIG. 10A is a schematic of a surgical visualization system utilizing a camera that is moved axially between a plurality of known positions to determine a position of an embedded critical structure, according to at least one aspect of the present disclosure.

In another aspect, referring now to FIGS. 10A and 10B, a surgical visualization system may employ a dithering or moving camera 440 to determine the distance $d_w$. The camera 440 is robotically-controlled such that the three-dimensional coordinates of the camera 440 at the different positions are known. In various instances, the camera 440 can pivot at a cannula or patient interface. For example, if a critical structure 401 or the contents thereof (e.g. a vessel or the contents of the vessel) can emit a signal, such as with fluoroscopy, for example, then the actual location can be triangulated from the camera 440 moved rapidly between two or more known locations. In FIG. 10A, the camera 440 is moved axially along an axis A. More specifically, the camera 440 translates a distance $d_1$ closer to the critical structure 401 along the axis A to the location indicated as a location 440', such as by moving in and out on a robotic arm. As the camera 440 moves the distance $d_1$ and the size of view change with respect to the critical structure 401, the distance to the critical structure 401 can be calculated. For example, a 4.28 mm axial translation (the distance $d_1$) can correspond to an angle $\theta_1$ of 6.28 degrees and an angle $\theta_2$ of 8.19 degrees. Additionally or alternatively, the camera 440 can rotate or sweep along an arc between different positions. Referring now to FIG. 10B, the camera 440 is moved axially along the axis A and is rotated an angle $\theta_3$ about the axis A. A pivot point 442 for rotation of the camera 440 is positioned at the cannula/patient interface. In FIG. 10B, the camera 440 is translated and rotated to a location 440". As the camera 440 moves and the edge of view changes with respect to the critical structure 401, the distance to the critical structure 401 can be calculated. In FIG. 10B, a distance $d_2$ can be 9.01 mm, for example, and the angle $\theta_3$ can be 0.9 degrees, for example.

Figure 5:
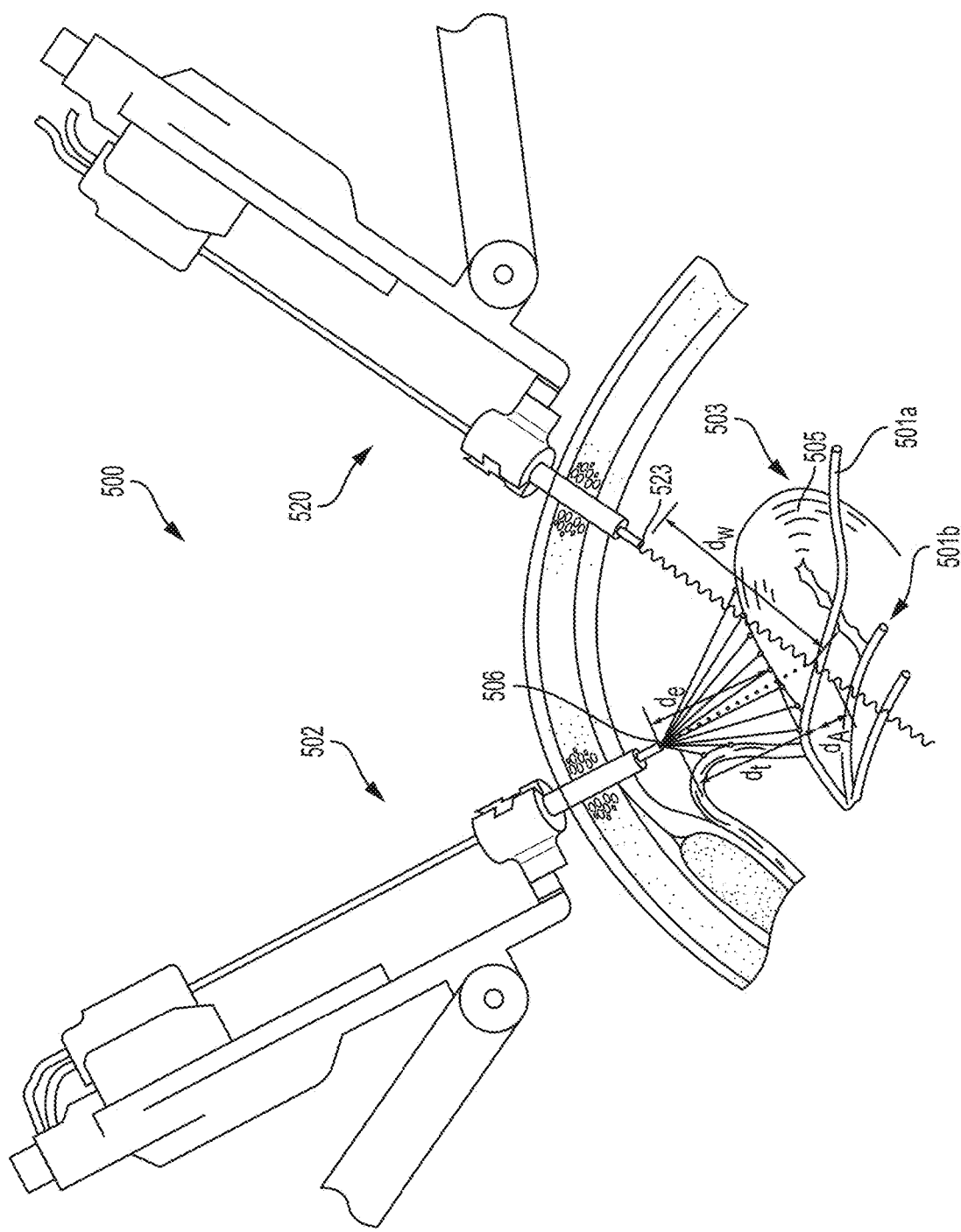
FIG. 5 is a schematic of a surgical visualization system including an imaging device and a surgical device, the surgical visualization system configured to identify a critical structure below a tissue surface, according to at least one aspect of the present disclosure.

FIG. 5 depicts a surgical visualization system 500, which is similar to the surgical visualization system 100 in many respects. In various instances, the surgical visualization system 500 can be a further exemplification of the surgical visualization system 100. Similar to the surgical visualization system 100, the surgical visualization system 500 includes a surgical device 502 and an imaging device 520. The imaging device 520 includes a spectral light emitter 523, which is configured to emit spectral light in a plurality of wavelengths to obtain a spectral image of hidden structures, for example. The imaging device 520 can also include a three-dimensional camera and associated electronic processing circuits in various instances. The surgical visualization system 500 is shown being utilized intraoperatively to identify and facilitate avoidance of certain critical structures, such as a ureter 501a and vessels 501b in an organ 503 (the uterus in this example), that are not visible on the surface.

The surgical visualization system 500 is configured to determine an emitter-to-tissue distance $d_e$ from an emitter 506 on the surgical device 502 to a surface 505 of the uterus 503 via structured light. The surgical visualization system 500 is configured to extrapolate a device-to-tissue distance $d_t$ from the surgical device 502 to the surface 505 of the uterus 503 based on the emitter-to-tissue distance $d_e$. The surgical visualization system 500 is also configured to determine a tissue-to-ureter distance $d_A$ from the ureter 501a to the surface 505 and a camera-to ureter distance $d_w$ from the imaging device 520 to the ureter 501a. As described herein with respect to FIG. 1, for example, the surgical visualization system 500 can determine the distance $d_w$ with spectral imaging and time-of-flight sensors, for example. In various instances, the surgical visualization system 500 can determine (e.g. triangulate) the tissue-to-ureter distance $d_A$ (or depth) based on other distances and/or the surface mapping logic described herein.

Figure 11:
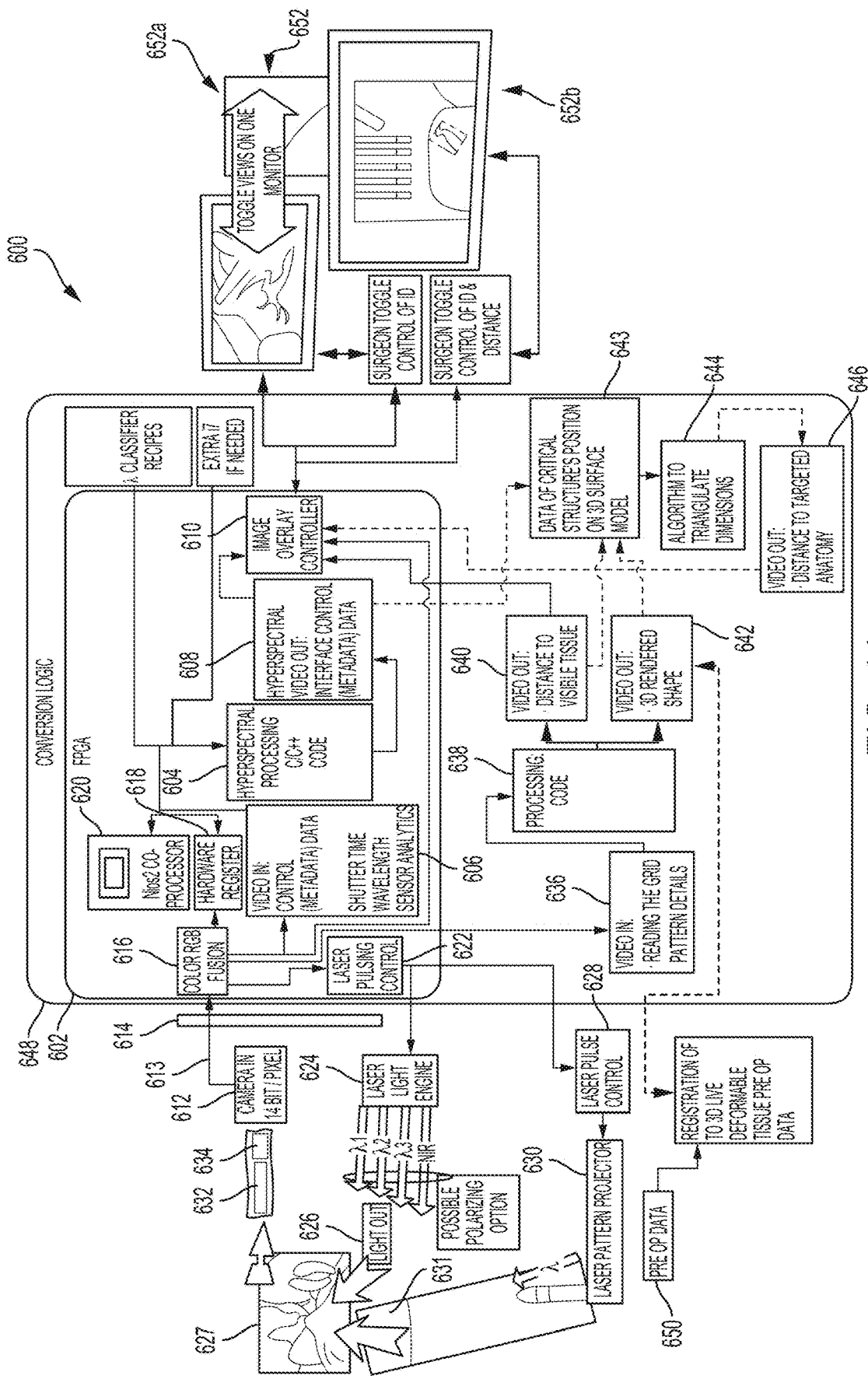
FIG. 11 is a schematic of a control system for a surgical visualization system, according to at least one aspect of the present disclosure.

Referring now to FIG. 11, where a schematic of a control system 600 for a surgical visualization system, such as the surgical visualization system 100, for example, is depicted. The control system 600 is a conversion system that integrates spectral signature tissue identification and structured light tissue positioning to identify critical structures, especially when those structures are obscured by other tissue, such as fat, connective tissue, blood, and/or other organs, for example. Such technology could also be useful for detecting tissue variability, such as differentiating tumors and/or non-healthy tissue from healthy tissue within an organ.

The control system 600 is configured for implementing a hyperspectral imaging and visualization system in which a molecular response is utilized to detect and identify anatomy in a surgical field of view. The control system 600 includes a conversion logic circuit 648 to convert tissue data to surgeon usable information. For example, the variable reflectance based on wavelengths with respect to obscuring material can be utilized to identify the critical structure in the anatomy. Moreover, the control system 600 combines the identified spectral signature and the structural light data in an image. For example, the control system 600 can be employed to create of three-dimensional data set for surgical use in a system with augmentation image overlays. Techniques can be employed both intraoperatively and preoperatively using additional visual information. In various instances, the control system 600 is configured to provide warnings to a clinician when in the proximity of one or more critical structures. Various algorithms can be employed to guide robotic automation and semi-automated approaches based on the surgical procedure and proximity to the critical structure(s).

A projected array of lights is employed to determine tissue shape and motion intraoperatively. Alternatively, flash Lidar may be utilized for surface mapping of the tissue.

The control system 600 is configured to detect the critical structure(s) and provide an image overlay of the critical structure and measure the distance to the surface of the visible tissue and the distance to the embedded/buried critical structure(s). In other instances, the control system 600 can measure the distance to the surface of the visible tissue or detect the critical structure(s) and provide an image overlay of the critical structure.

The control system 600 includes a spectral control circuit 602. The spectral control circuit 602 can be a field programmable gate array (FPGA) or another suitable circuit configuration as described herein in connection with FIGS. 2A-2C, for example. The spectral control circuit 602 includes a processor 604 to receive video input signals from a video input processor 606. The processor 604 can be configured for hyperspectral processing and can utilize C/C++ code, for example. The video input processor 606 receives video-in of control (metadata) data such as shutter time, wave length, and sensor analytics, for example. The processor 604 is configured to process the video input signal from the video input processor 606 and provide a video output signal to a video output processor 608, which includes a hyperspectral video-out of interface control (metadata) data, for example. The video output processor 608 provides the video output signal to an image overlay controller 610.

The video input processor 606 is coupled to a camera 612 at the patient side via a patient isolation circuit 614. As previously discussed, the camera 612 includes a solid state image sensor 634. The patient isolation circuit can include a plurality of transformers so that the patient is isolated from other circuits in the system. The camera 612 receives intraoperative images through optics 632 and the image sensor 634. The image sensor 634 can include a CMOS image sensor, for example, or may include any of the image sensor technologies discussed herein in connection with FIG. 2, for example. In one aspect, the camera 612 outputs images in 14 bit/pixel signals. It will be appreciated that higher or lower pixel resolutions may be employed without departing from the scope of the present disclosure. The isolated camera output signal 613 is provided to a color RGB fusion circuit 616, which employs a hardware register 618 and a Nios2 co-processor 620 to process the camera output signal 613. A color RGB fusion output signal is provided to the video input processor 606 and a laser pulsing control circuit 622.

The laser pulsing control circuit 622 controls a laser light engine 624. The laser light engine 624 outputs light in a plurality of wavelengths ($\lambda_1, \lambda_2, \lambda_3 \ldots \lambda_n$) including near infrared (NIR). The laser light engine 624 can operate in a plurality of modes. In one aspect, the laser light engine 624 can operate in two modes, for example. In a first mode, e.g. a normal operating mode, the laser light engine 624 outputs an illuminating signal. In a second mode, e.g. an identification mode, the laser light engine 624 outputs RGBG and NIR light. In various instances, the laser light engine 624 can operate in a polarizing mode.

Light output 626 from the laser light engine 624 illuminates targeted anatomy in an intraoperative surgical site 627. The laser pulsing control circuit 622 also controls a laser pulse controller 628 for a laser pattern projector 630 that projects a laser light pattern 631, such as a grid or pattern of lines and/or dots, at a predetermined wavelength ($\lambda_2$) on the operative tissue or organ at the surgical site 627. The camera 612 receives the patterned light as well as the reflected light output through the camera optics 632. The image sensor 634 converts the received light into a digital signal.

The color RGB fusion circuit 616 also outputs signals to the image overlay controller 610 and a video input module 636 for reading the laser light pattern 631 projected onto the targeted anatomy at the surgical site 627 by the laser pattern projector 630. A processing module 638 processes the laser light pattern 631 and outputs a first video output signal 640 representative of the distance to the visible tissue at the surgical site 627. The data is provided to the image overlay controller 610. The processing module 638 also outputs a second video signal 642 representative of a three-dimensional rendered shape of the tissue or organ of the targeted anatomy at the surgical site.

The first and second video output signals 640, 642 include data representative of the position of the critical structure on a three-dimensional surface model, which is provided to an integration module 643. In combination with data from the video out processor 608 of the spectral control circuit 602, the integration module 643 can determine the distance $d_A$ (FIG. 1) to a buried critical structure (e.g. via triangularization algorithms 644), and the distance $d_A$ can be provided to the image overlay controller 610 via a video out processor 646. The foregoing conversion logic can encompass the conversion logic circuit 648 intermediate video monitors 652 and the camera 624/laser pattern projector 630 positioned at the surgical site 627.

Preoperative data 650 from a CT or MRI scan can be employed to register or align certain three-dimensional deformable tissue in various instances. Such preoperative data 650 can be provided to the integration module 643 and ultimately to the image overlay controller 610 so that such information can be overlaid with the views from the camera 612 and provided to the video monitors 652. Registration of preoperative data is further described herein and in the aforementioned contemporaneously-filed U.S. Patent Applications, including U.S. patent application Ser. No. 16/128,195, titled INTEGRATION OF IMAGING DATA, now U.S. Patent Application Publication No. 2020/0015907, for example, which are incorporated by reference herein in their respective entireties.

The video monitors 652 can output the integrated/augmented views from the image overlay controller 610. A clinician can select and/or toggle between different views on one or more monitors. On a first monitor 652a, the clinician can toggle between (A) a view in which a three-dimensional rendering of the visible tissue is depicted and (B) an augmented view in which one or more hidden critical structures are depicted over the three-dimensional rendering of the visible tissue. On a second monitor 652b, the clinician can toggle on distance measurements to one or more hidden critical structures and/or the surface of visible tissue, for example.

The control system 600 and/or various control circuits thereof can be incorporated into various surgical visualization systems disclosed herein.

Figure 12:
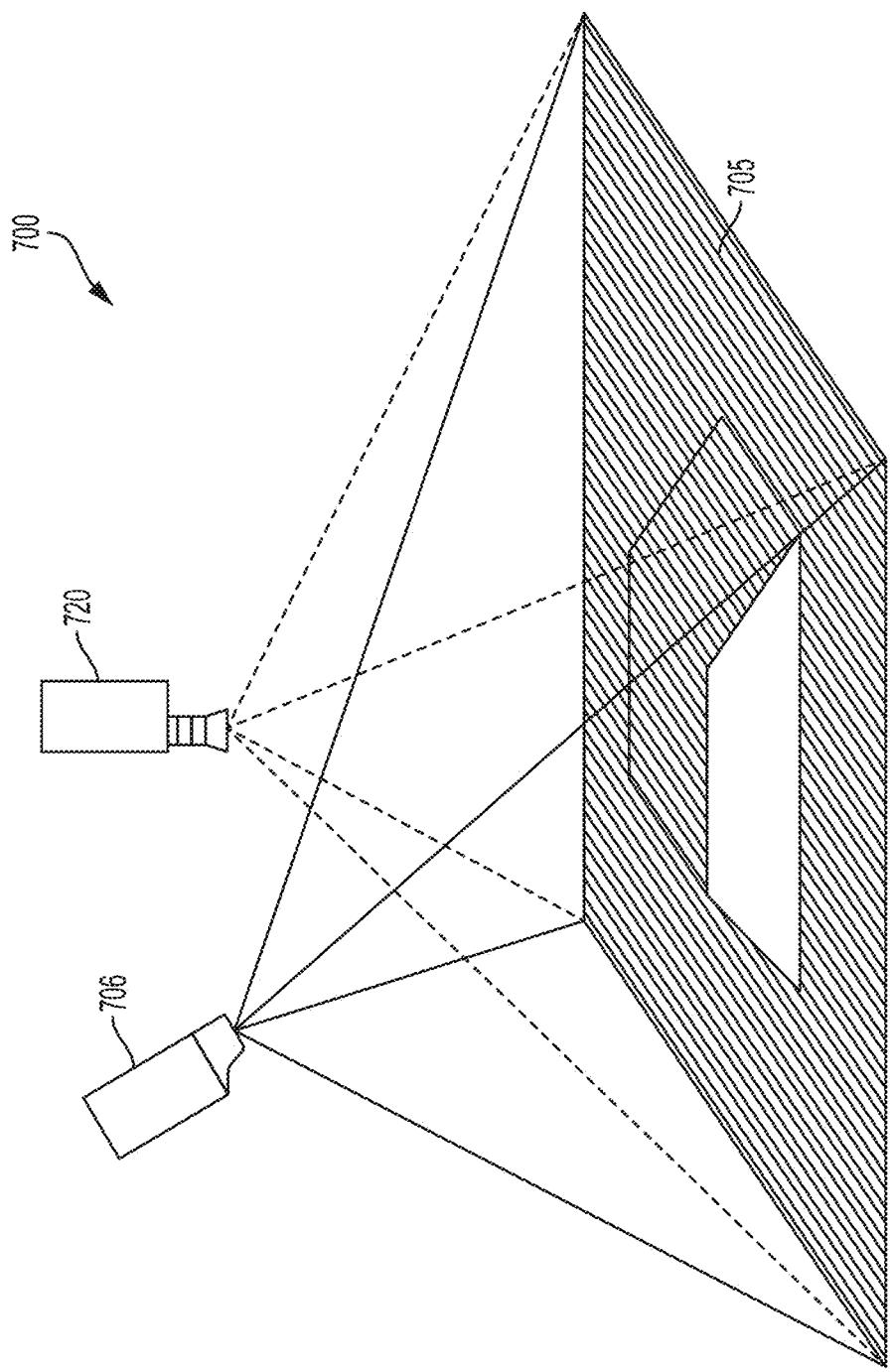
FIG. 12 is a schematic of a structured light source for a surgical visualization system, according to at least one aspect of the present disclosure.

FIG. 12 illustrates a structured (or patterned) light system 700, according to at least one aspect of the present disclosure. As described herein, structured light in the form of stripes or lines, for example, can be projected from a light source and/or projector 706 onto the surface 705 of targeted anatomy to identify the shape and contours of the surface 705. A camera 720, which can be similar in various respects to the imaging device 120 (FIG. 1), for example, can be configured to detect the projected pattern of light on the surface 705. The way that the projected pattern deforms upon striking the surface 705 allows vision systems to calculate the depth and surface information of the targeted anatomy.

In certain instances, invisible (or imperceptible) structured light can be utilized, in which the structured light is used without interfering with other computer vision tasks for which the projected pattern may be confusing. For example, infrared light or extremely fast frame rates of visible light that alternate between two exact opposite patterns can be utilized to prevent interference. Structured light is further described at en.wikipedia.org/wiki/Structured_light.

Figure 13:
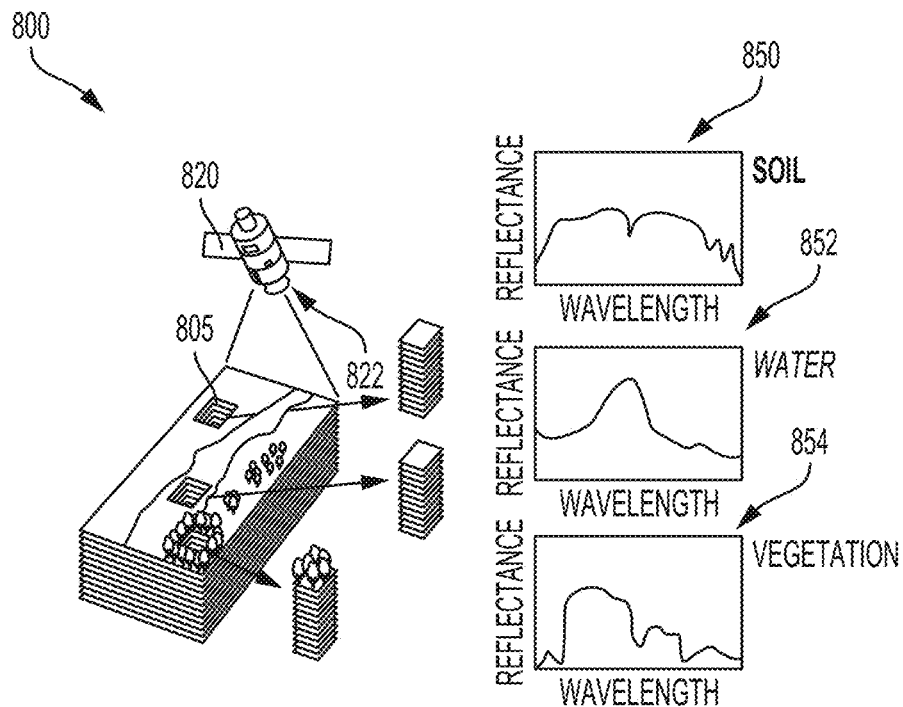
FIG. 13 is a schematic of a hyperspectral visualization system for imaging terrestrial features or objects, according to at least one aspect of the present disclosure.

Referring now to FIG. 13, by way example to illustrate the concept of hyperspectral imaging, a terrestrial hyperspectral imaging system 800 is shown. The terrestrial hyperspectral imaging system 800 is configured to image terrestrial features or objects, such as soil, water, and/or vegetation, for example. The terrestrial hyperspectral imaging system 700 includes a space-borne hyperspectral sensor 822 on a spacecraft 820 to conduct hyperspectral imaging of a portion of the Earth's surface 805. The spectral dimension includes several layers. Each pixel of the images contains a sampled spectrum that is used to identify the materials present in the pixel by their reflectance. The data can be converted to graphical representations 850, 852, 854 of reflectance as a function of wavelength for soil, water, and vegetation, respectively, for example. Terrestrial hyperspectral imaging is further described at www.markelowitz.com/Hyperspectral.html.

Figure 14:
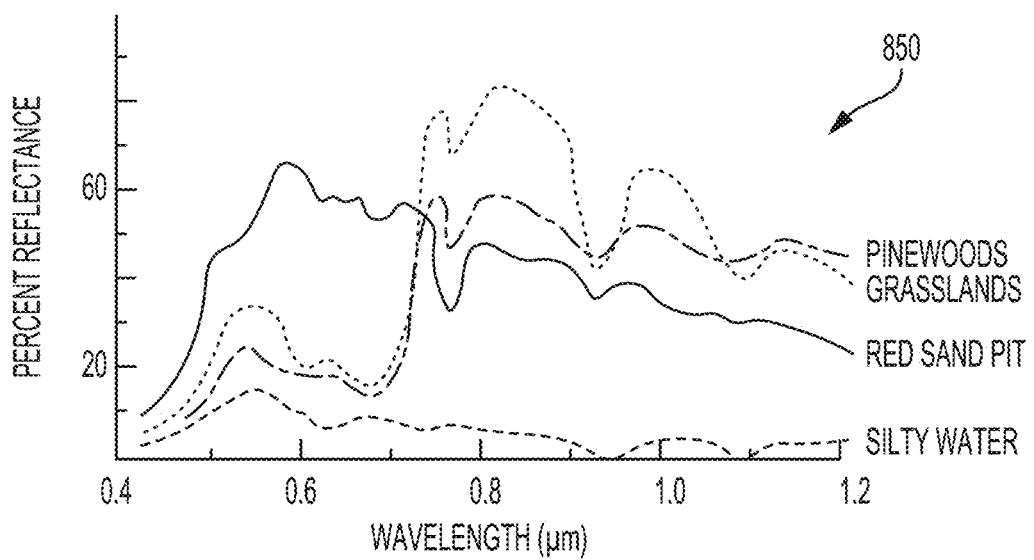
FIG. 14 is a graphical representation of hyperspectral signatures for various terrestrial features or objects, according to at least one aspect of the present disclosure.

Also by way example to illustrate the concept of hyperspectral imaging, FIG. 14 is a graphical representation 850 of hyperspectral signatures for various terrestrial features or objects, according to at least one aspect of the present disclosure. Percent reflectance is shown along the vertical axis and wavelength (nm) is shown along the horizontal axis. As shown, each object—pinewoods, grasslands, red sand pit, and silty water—has a unique hyperspectral signature that can be used to identify the object.

The hyperspectral imaging concepts described in connection with FIGS. 13 and 14 may be employed for different materials that have different wavelengths and bands of absorption, according to at least one aspect of the present disclosure. The following table illustrates the wavelengths and bands of absorption for various materials. A first range of wavelengths between 400 nm and 700 nm represents the visible light spectrum. A second range of wavelengths between 700 nm and 1400 nm represents the near infrared (NIR) spectrum. A third range of wavelengths between 1400 nm and 3000 nm represents a shortwave infrared (SWIR) spectrum. A first band centered at 1250 nm represents iron absorption and leaf moisture content. A second band between 1500 nm and 1750 nm represents plastics, fiberglass, and petroleum. A third band between 200 nm and 2400 nm represents mineral ID.

TABLE 1 specifies wavelengths and bands of absorption for various materials.

TABLE 1

| Wavelength (nm) | Region | Band(s) | Material |
| --- | --- | --- | --- |
| 400-700 | Visible | | |
| 700-1400 | NIR | | |
| 1400-3000 | SWIR | 1—centered at 1250 | Iron adsorption |
| | | | Leaf moisture content |
| | | 2—1500-1750 | Plastics |
| | | | Fiberglass |
| | | | Petroleum |
| | | 3—200-2400 nm | Mineral ID |

Referring now to FIGS. 15A-15C, as a further illustration of hyperspectral imaging concepts, tests were conducted in which spectral imaging was applied to a fried egg 952. An image of the fried egg 952 with a yellow egg yolk 954 and an egg white 956 surrounding the egg yolk 954 is shown in FIG. 15A. A graphical representation 950 of spectral signatures for the fried egg 952 are shown in FIG. 15B. Specifically, the graphical representation 950 shows absorption units versus wavelength (nm) for the egg yolk 954 and the egg white 956 of the fried egg 952. In FIG. 15C, a spectral image (in black-and-white) of the fried egg 952 is shown, in which the image is augmented to differentiate between the egg yolk portion and the egg white portion based on the hyperspectral signature data.

In various instances, hyperspectral imaging technology, as described herein for illustrative purposes with respect to terrestrial features and objects and a fried egg, can be employed to identify signatures in anatomical structures in order to differentiate a critical structure from obscurants. Hyperspectral imaging technology may provide a visualization system that can provide a way to identify critical structures such as ureters and/or blood vessels, for example, especially when those structures are obscured by fat, connective tissue, blood, or other organs, for example. The use of the difference in reflectance of different wavelengths in the infrared (IR) spectrum may be employed to determine the presence of key structures versus obscurants. Referring now to FIGS. 16-18, illustrative hyperspectral signatures for a ureter, an artery, and nerve tissue with respect to obscurants such as fat, lung tissue, and blood, for example, are depicted.

FIG. 16 is a graphical representation 1050 of an illustrative ureter signature versus obscurants. The plots represent reflectance as a function of wavelength (nm) for wavelengths for fat, lung tissue, blood, and a ureter. FIG. 17 is a graphical representation 1052 of an illustrative artery signature versus obscurants. The plots represent reflectance as a function of wavelength (nm) for fat, lung tissue, blood, and a vessel. FIG. 18 is a graphical representation 1054 of an illustrative nerve signature versus obscurants. The plots represent reflectance as a function of wavelength (nm) for fat, lung tissue, blood, and a nerve.

In various instances, select wavelengths for spectral imaging can be identified and utilized based on the anticipated critical structures and/or obscurants at a surgical site (i.e. "selective spectral" imaging). By utilizing selective spectral imaging, the amount of time required to obtain the spectral image can be minimized such that the information can be obtained in real-time, or near real-time, and utilized intraoperatively. In various instances, the wavelengths can be selected by a clinician or by a control circuit based on input by the clinician. In certain instances, the wavelengths can be selected based on machine learning and/or big data accessible to the control circuit via a cloud, for example.

The foregoing application of spectral imaging to tissue can be utilized intraoperatively to measure the distance between a waveform emitter and a critical structure that is obscured by tissue. In one aspect of the present disclosure, referring now to FIGS. 19 and 20, a time-of-flight sensor system 1104 utilizing waveforms 1124, 1125 is shown. The time-of-flight sensor system 1104 can be incorporated into the surgical visualization system 100 (FIG. 1) in certain instances. The time-of-flight sensor system 1104 includes a waveform emitter 1106 and a waveform receiver 1108 on the same surgical device 1102. The emitted wave 1124 extends to the critical structure 1101 from the emitter 1106 and the received wave 1125 is reflected back to by the receiver 1108 from the critical structure 1101. The surgical device 1102 is positioned through a trocar 1110 that extends into a cavity 1107 in a patient.

The waveforms 1124, 1125 are configured to penetrate obscuring tissue 1103. For example, the wavelengths of the waveforms 1124, 1125 can be in the NIR or SWIR spectrum of wavelengths. In one aspect, a spectral signal (e.g. hyperspectral, multispectral, or selective spectral) or a photoacoustic signal can be emitted from the emitter 1106 and can penetrate the tissue 1103 in which the critical structure 1101 is concealed. The emitted waveform 1124 can be reflected by the critical structure 1101. The received waveform 1125 can be delayed due to the distance d between the distal end of the surgical device 1102 and the critical structure 1101. In various instances, the waveforms 1124, 1125 can be selected to target the critical structure 1101 within the tissue 1103 based on the spectral signature of the critical structure 1101, as further described herein. In various instances, the emitter 1106 is configured to provide a binary signal on and off, as shown in FIG. 20, for example, which can be measured by the receiver 1108.

Based on the delay between the emitted wave 1124 and the received wave 1125, the time-of-flight sensor system 1104 is configured to determine the distance d (FIG. 19). A time-of-flight timing diagram 1130 for the emitter 1106 and the receiver 1108 of FIG. 19 is shown in FIG. 20. The delay is a function of the distance d and the distance d is given by:

$$d = \frac{ct}{2} \cdot \frac{q_2}{q_1 + q_2}$$

where:
c=the speed of light;
t=length of pulse;
$q_1$=accumulated charge while light is emitted; and
$q_2$=accumulated charge while light is not being emitted.

As provided herein, the time-of-flight of the waveforms 1124, 1125 corresponds to the distance d in FIG. 19. In various instances, additional emitters/receivers and/or pulsing signals from the emitter 1106 can be configured to emit a non-penetrating signal. The non-penetrating tissue can be configured to determine the distance from the emitter to the surface 1105 of the obscuring tissue 1103. In various instances, the depth of the critical structure 1101 can be determined by:

$$d_A = d_w - d_t$$

where:
$d_A$=the depth of the critical structure 1101;
$d_w$=the distance from the emitter 1106 to the critical structure 1101 (d in FIG. 19); and
$d_t$=the distance from the emitter 1106 (on the distal end of the surgical device 1102) to the surface 1105 of the obscuring tissue 1103.

In one aspect of the present disclosure, referring now to FIG. 21, a time-of-flight sensor system 1204 utilizing waves 1224a, 1224b, 1224c, 1225a, 1225b, 1225c is shown. The time-of-flight sensor system 1204 can be incorporated into the surgical visualization system 100 (FIG. 1) in certain instances. The time-of-flight sensor system 1204 includes a waveform emitter 1206 and a waveform receiver 1208. The waveform emitter 1206 is positioned on a first surgical device 1202a, and the waveform receiver 1208 is positioned on a second surgical device 1202b. The surgical devices 1202a, 1202b are positioned through their respective trocars 1210a, 1210b, respectively, which extend into a cavity 1207 in a patient. The emitted waves 1224a, 1224b, 1224c extend toward a surgical site from the emitter 1206 and the received waves 1225a, 1225b, 1225c are reflected back to the receiver 1208 from various structures and/or surfaces at the surgical site.

The different emitted waves 1224a, 1224b, 1224c are configured to target different types of material at the surgical site. For example, the wave 1224a targets the obscuring tissue 1203, the wave 1224b targets a first critical structure 1201a (e.g. a vessel), and the wave 1224c targets a second critical structure 1201b (e.g. a cancerous tumor). The wavelengths of the waves 1224a, 1224b, 1224c can be in the visible light, NIR, or SWIR spectrum of wavelengths. For example, visible light can be reflected off a surface 1205 of the tissue 1203 and NIR and/or SWIR waveforms can be configured to penetrate the surface 1205 of the tissue 1203. In various aspects, as described herein, a spectral signal (e.g. hyperspectral, multispectral, or selective spectral) or a photoacoustic signal can be emitted from the emitter 1206. In various instances, the waves 1224b, 1224c can be selected to target the critical structures 1201a, 1201b within the tissue 1203 based on the spectral signature of the critical structure 1201a, 1201b, as further described herein. Photoacoustic imaging is further described herein and in the aforementioned contemporaneously-filed U.S. Patent Applications, which are incorporated by reference herein in their respective entireties.

The emitted waves 1224a, 1224b, 1224c can be reflected off the targeted material (i.e. the surface 1205, the first critical structure 1201a, and the second structure 1201b, respectively). The received waveforms 1225a, 1225b, 1225c can be delayed due to the distances $d_{1a}$, $d_{2a}$, $d_{3a}$, $d_{1b}$, $d_{2b}$, $d_{2c}$ indicated in FIG. 21.

In the time-of-flight sensor system 1204, in which the emitter 1206 and the receiver 1208 are independently positionable (e.g., on separate surgical devices 1202a, 1202b and/or controlled by separate robotic arms), the various distances $d_{1a}$, $d_{2a}$, $d_{3a}$, $d_{1b}$, $d_{2b}$, $d_{2c}$ can be calculated from the known position of the emitter 1206 and the receiver 1208. For example, the positions can be known when the surgical devices 1202a, 1202b are robotically-controlled. Knowledge of the positions of the emitter 1206 and the receiver 1208, as well as the time of the photon stream to target a certain tissue and the information received by the receiver 1208 of that particular response can allow a determination of the distances $d_{1a}$, $d_{2a}$, $d_{3a}$, $d_{1b}$, $d_{2b}$, $d_{2c}$. In one aspect, the distance to the obscured critical structures 1201a, 1201b can be triangulated using penetrating wavelengths. Because the speed of light is constant for any wavelength of visible or invisible light, the time-of-flight sensor system 1204 can determine the various distances.

Referring still to FIG. 21, in various instances, in the view provided to the clinician, the receiver 1208 can be rotated such that the center of mass of the target structure in the resulting images remains constant, i.e., in a plane perpendicular to the axis of a select target structures 1203, 1201a, or 1201b. Such an orientation can quickly communicate one or more relevant distances and/or perspectives with respect to the critical structure. For example, as shown in FIG. 21, the surgical site is displayed from a viewpoint in which the critical structure 1201a is perpendicular to the viewing plane (i.e. the vessel is oriented in/out of the page). In various instances, such an orientation can be default setting; however, the view can be rotated or otherwise adjusted by a clinician. In certain instances, the clinician can toggle between different surfaces and/or target structures that define the viewpoint of the surgical site provided by the imaging system.

In various instances, the receiver 1208 can be mounted on a trocar or cannula, such as the trocar 1210b, for example, through which the surgical device 1202b is positioned. In other instances, the receiver 1208 can be mounted on a separate robotic arm for which the three-dimensional position is known. In various instances, the receiver 1208 can be mounted on a movable arm that is separate from the robot that controls the surgical device 1202a or can be mounted to an operating room (OR) table that is intraoperatively registerable to the robot coordinate plane. In such instances, the position of the emitter 1206 and the receiver 1208 can be registerable to the same coordinate plane such that the distances can be triangulated from outputs from the time-of-flight sensor system 1204.

Combining time-of-flight sensor systems and near-infrared spectroscopy (NIRS), termed TOF-NIRS, which is capable of measuring the time-resolved profiles of NIR light with nanosecond resolution can be found in the article titled TIME-OF-FLIGHT NEAR-INFRARED SPECTROSCOPY FOR NONDESTRUCTIVE MEASUREMENT OF INTERNAL QUALITY IN GRAPEFRUIT, in the Journal of the American Society for Horticultural Science, May 2013 vol. 138 no. 3 225-228, which is incorporated by reference herein in its entirety, and is accessible at journal.ashspublications.org/content/138/3/225.full.

In various instances, time-of-flight spectral waveforms are configured to determine the depth of the critical structure and/or the proximity of a surgical device to the critical structure. Moreover, the various surgical visualization systems disclosed herein include surface mapping logic that is configured to create three-dimensional rendering of the surface of the visible tissue. In such instances, even when the visible tissue obstructs a critical structure, the clinician can be aware of the proximity (or lack thereof) of a surgical device to the critical structure. In one instances, the topography of the surgical site is provided on a monitor by the surface mapping logic. If the critical structure is close to the surface of the tissue, spectral imaging can convey the position of the critical structure to the clinician. For example, spectral imaging may detect structures within 5 or 10 mm of the surface. In other instances, spectral imaging may detect structures 10 or 20 mm below the surface of the tissue. Based on the known limits of the spectral imaging system, the system is configured to convey that a critical structure is out-of-range if it is simply not detected by the spectral imaging system. Therefore, the clinician can continue to move the surgical device and/or manipulate the tissue. When the critical structure moves into range of the spectral imaging system, the system can identify the structure and, thus, communicate that the structure is within range. In such instances, an alert can be provided when a structure is initially identified and/or moved further within a predefined proximity zone. In such instances, even non-identification of a critical structure by a spectral imaging system with known bounds/ranges can provide proximity information (i.e. the lack of proximity) to the clinician.

Various surgical visualization systems disclosed herein can be configured to identify intraoperatively the presence of and/or proximity to critical structure(s) and to alert a clinician prior to damaging the critical structure(s) by inadvertent dissection and/or transection. In various aspects, the surgical visualization systems are configured to identify one or more of the following critical structures: ureters, bowel, rectum, nerves (including the phrenic nerve, recurrent laryngeal nerve [RLN], promontory facial nerve, vagus nerve, and branches thereof), vessels (including the pulmonary and lobar arteries and veins, inferior mesenteric artery [IMA] and branches thereof, superior rectal artery, sigmoidal arteries, and left colic artery), superior mesenteric artery (SMA) and branches thereof (including middle colic artery, right colic artery, ilecolic artery), hepatic artery and branches thereof, portal vein and branches thereof, splenic artery/vein and branches thereof, external and internal (hypogastric) ileac vessels, short gastric arteries, uterine arteries, middle sacral vessels, and lymph nodes, for example. Moreover, the surgical visualization systems are configured to indicate proximity of surgical device(s) to the critical structure(s) and/or warn the clinician when surgical device(s) are getting close to the critical structure(s).

Various aspects of the present disclosure provide intraoperative critical structure identification (e.g., identification of ureters, nerves, and/or vessels) and instrument proximity monitoring. For example, various surgical visualization systems disclosed herein can include spectral imaging and surgical instrument tracking, which enable the visualization of critical structures below the surface of the tissue, such as 1.0-1.5 cm below the surface of the tissue, for example. In other instances, the surgical visualization system can identify structures less than 1.0 cm or more the 1.5 cm below the surface of the tissue. For example, even a surgical visualization system that can identify structures only within 0.2 mm of the surface, for example, can be valuable if the structure cannot otherwise be seen due to the depth. In various aspects, the surgical visualization system can augment the clinician's view with a virtual depiction of the critical structure as a visible white-light image overlay on the surface of visible tissue, for example. The surgical visualization system can provide real-time, three-dimensional spatial tracking of the distal tip of surgical instruments and can provide a proximity alert when the distal tip of a surgical instrument moves within a certain range of the critical structure, such as within 1.0 cm of the critical structure, for example.

Various surgical visualization systems disclosed herein can identify when dissection is too close to a critical structure. Dissection may be "too close" to a critical structure based on the temperature (i.e. too hot within a proximity of the critical structure that may risk damaging/heating/melting the critical structure) and/or based on tension (i.e. too much tension within a proximity of the critical structure that may risk damaging/tearing/pulling the critical structure). Such a surgical visualization system can facilitate dissection around vessels when skeletonizing the vessels prior to ligation, for example. In various instances, a thermal imaging camera can be utilized to read the heat at the surgical site and provide a warning to the clinician that is based on the detected heat and the distance from a tool to the structure. For example, if the temperature of the tool is over a predefined threshold (such as 120 degrees F., for example), an alert can be provided to the clinician at a first distance (such as 10 mm, for example), and if the temperature of the tool is less than or equal to the predefined threshold, the alert can be provided to the clinician at a second distance (such as 5 mm, for example). The predefined thresholds and/or warning distances can be default settings and/or programmable by the clinician. Additionally or alternatively, a proximity alert can be linked to thermal measurements made by the tool itself, such as a thermocouple that measures the heat in a distal jaw of a monopolar or bipolar dissector or vessel sealer, for example.

Various surgical visualization systems disclosed herein can provide adequate sensitivity with respect to a critical structure and specificity to enable a clinician to proceed with confidence in a quick but safe dissection based on the standard of care and/or device safety data. The system can function intraoperatively and in real-time during a surgical procedure with minimal ionizing radiation risk to a patient or a clinician and, in various instances, no risk of ionizing radiation risk to the patient or the clinician. Conversely, in a fluoroscopy procedure, the patient and clinician(s) may be exposed to ionizing radiation via an X-ray beam, for example, that is utilized to view the anatomical structures in real-time.

Various surgical visualization system disclosed herein can be configured to detect and identify one or more desired types of critical structures in a forward path of a surgical device, such as when the path of the surgical device is robotically controlled, for example. Additionally or alternatively, the surgical visualization system can be configured to detect and identify one or more types of critical structures in a surrounding area of the surgical device and/or in multiple planes/dimensions, for example.

Various surgical visualization systems disclosed herein can be easy to operate and/or interpret. Moreover, various surgical visualization systems can incorporate an "override" feature that allows the clinician to override a default setting and/or operation. For example, a clinician can selectively turn off alerts from the surgical visualization system and/or get closer to a critical structure than suggested by the surgical visualization system such as when the risk to the critical structure is less than risk of avoiding the area (e.g. when removing cancer around a critical structure the risk of leaving the cancerous tissue can be greater than the risk of damage to the critical structure).

Various surgical visualization systems disclosed herein can be incorporated into a surgical system and/or used during a surgical procedure with limited impact to the workflow. In other words, implementation of the surgical visualization system may not change the way the surgical procedure is implemented. Moreover, the surgical visualization system can be economical in comparison to the costs of an inadvertent transection. Data indicates the reduction in inadvertent damage to a critical structure can drive incremental reimbursement.

Various surgical visualization systems disclosed herein can operate in real-time, or near real-time, and far enough in advance to enable a clinician to anticipate critical structure(s). For example, a surgical visualization system can provide enough time to "slow down, evaluate, and avoid" in order to maximize efficiency of the surgical procedure.

Various surgical visualization systems disclosed herein may not require a contrast agent, or dye, that is injected into tissue. For example, spectral imaging is configured to visualize hidden structures intraoperatively without the use of a contrast agent or dye. In other instances, the contrast agent can be easier to inject into the proper layer(s) of tissue than other visualization systems. The time between injection of the contrast agent and visualization of the critical structure can be less than two hours, for example.

Various surgical visualization systems disclosed herein can be linked with clinical data and/or device data. For example, data can provide boundaries for how close energy-enabled surgical devices (or other potentially damaging devices) should be from tissue that the surgeon does not want to damage. Any data modules that interface with the surgical visualization systems disclosed herein can be provided integrally or separately from a robot to enable use with stand-alone surgical devices in open or laparoscopic procedures, for example. The surgical visualization systems can be compatible with robotic surgical systems in various instances. For example, the visualization images/information can be displayed in a robotic console.

Example Clinical Applications

Various surgical visualization systems disclosed herein may be employed in one or more of the following clinical applications. The following clinical applications are non-exhaustive and merely illustrative applications for one or more of the various surgical visualization systems disclosed herein.

A surgical visualization system, as disclosed herein, can be employed in a number of different types of procedures for different medical specialties, such as urology, gynecology, oncology, colorectal, thoracic, bariatric/gastric, and hepato-pancreato-biliary (HPB), for example. In urological procedures, such as a prostatectomy, for example, the ureter may be detected in fat or connective tissue and/or nerves may be detected in fat, for example. In gynecological oncology procedures, such as a hysterectomy, for example, and in colorectal procedures, such as a low anterior resection (LAR) procedure, for example, the ureter may be detected in fat and/or in connective tissue, for example. In thoracic procedures, such as a lobectomy, for example, a vessel may be detected in the lung or in connective tissue and/or a nerve may be detected in connective tissue (e.g., an esophagostomy). In bariatric procedures, a vessel may be detected in fat. In HPB procedures, such as a hepatectomy or pancreatectomy, for example, a vessel may be detected in fat (extrahepatic), in connective tissue (extrahepatic), and the bile duct may be detected in parenchyma (liver or pancreas) tissue.

In one example, a clinician may want to remove an endometrial myoma. From a preoperative magnetic resonance imaging (MRI) scan, the clinician may know that the endometrial myoma is located on the surface of the bowel. Therefore, the clinician may want to know, intraoperatively, what tissue constitute a portion of the bowel and what tissue constitutes a portion of the rectum. In such instances, a surgical visualization system, as disclosed herein, can indicate the different types of tissue (bowel versus rectum) and convey that information to a clinician via an imaging system. Moreover, the imaging system can determine and communicate the proximity of a surgical device to the select tissue. In such instances, the surgical visualization system can provide increased procedural efficiency without critical complications.

In another example, a clinician (e.g. a gynecologist) may stay away from certain anatomic regions to avoid getting too close to critical structures and, thus, the clinician may not remove all of the endometriosis, for example. A surgical visualization system, as disclosed herein, can enable the gynecologist to mitigate the risk of getting too close to the critical structure such that the gynecologist can get close enough with the surgical device to remove all the endometriosis, which can improve the patient outcomes (democratizing surgery). Such a system can enable the surgeon to "keep moving" during the surgical procedure instead of repeatedly stopping and restarting in order to identify areas to avoid, especially during the application of therapeutic energy such as ultrasonic or electrosurgical energy, for example. In gynecological applications, uterine arteries and ureters are important critical structures and the system may be particularly useful for hysterectomy and endometriosis procedures given the presentation and/or thickness of tissue involved.

In another example, a clinician may risk dissection of a vessel at a location that is too proximal and, thus, which can affect blood supply to a lobe other than the target lobe. Moreover, anatomic differences from patient to patient may lead to dissection of a vessel (e.g. a branch) that affects a different lobe based on the particular patient. A surgical visualization system, as disclosed herein, can enable the identification of the correct vessel at the desired location, which enables the clinician to dissect with appropriate anatomic certainty. For example, the system can confirm that the correct vessel is in the correct place and then the clinician can safely divide the vessel.

In another example, a clinician may make multiple dissections before dissecting at the best location due to uncertainty about the anatomy of the vessel. However, it is desirable to dissect in the best location in the first instance because more dissection can increase the risk of bleeding. A surgical visualization system, as disclosed herein, can minimize the number of dissections by indicating the correct vessel and the best location for dissection. Ureters and cardinal ligaments, for example, are dense and provide unique challenges during dissection. In such instances, it can be especially desirable to minimize the number of dissections.

In another example, a clinician (e.g. a surgical oncologist) removing cancerous tissue may want to know the identification of critical structures, localization of the cancer, staging of the cancer, and/or an evaluation of tissue health. Such information is beyond what a clinician sees with the "naked eye". A surgical visualization system, as disclosed herein, can determine and/or convey such information to the clinician intraoperatively to enhance intraoperative decision making and improve surgical outcomes. In certain instances, the surgical visualization system can be compatible with minimally invasive surgery (MIS), open surgery, and/or robotic approaches using either an endoscope or exoscope, for example.

In another example, a clinician (e.g. a surgical oncologist) may want to turn off one or more alerts regarding the proximity of a surgical tool to one or more critical structure to avoid being overly conservative during a surgical procedure. In other instances, the clinician may want to receive certain types of alerts, such as haptic feedback (e.g. vibrations/buzzing) to indicate proximity and/or "no fly zones" to stay sufficiently far away from one or more critical structures. A surgical visualization system, as disclosed herein, can provide flexibility based on the experience of the clinician and/or desired aggressiveness of the procedure, for example. In such instances, the system provides a balance between "knowing too much" and "knowing enough" to anticipate and avoid critical structures. The surgical visualization system can assist in planning the next step(s) during a surgical procedure.

The systems, methods, devices, and control circuits discussed herein can also benefit and be used in a surgical suturing environment. More specifically, the surgical visualization systems can benefit surgical suturing systems. A clinician suturing tissue manually, robotically, and/or manually and robotically, can utilize such surgical visualization systems in a surgical suturing environment to help prevent contacting, puncturing, and/or scraping, for example, of an embedded structure with a suturing needle. In certain instances, the surgical visualization systems can be used to monitor the position of a needle in addition to the position of a critical structure. Discussed in greater detail below, surgical suturing systems utilizing such surgical visualization systems can monitor and/or track the relative position between a suturing needle and one or more embedded structures in real time, for example, and can alert a clinician and/or automatically adjust operation of a robot that may be assisting the suturing procedure, for example, if the needle gets too close to a embedded structure. Other surgical suturing systems are capable of predicting the path of a needle based on an initial starting point and comparing that path to detected embedded structures. Such systems can also recommend a different starting point and/or alert a clinician that the predicted suturing path to be preformed robotically may interfere with an embedded structure, for example.

In various instances, a system and method for robotically assisted suturing with indication of needle proximity to a critical structure is provided. The system and method are configured to prevent a suture needle from contacting a critical structure during robotic surgery. The system and method provide a technique for programming a suture needle driver, such as a grasper, for example, to perform repetitive portions of the suturing process.

FIG. 22 depicts a surgical suturing system 5700. The surgical suturing system 5700 comprises a grasper 5701, a surgical visualization assembly 5702 including a sensor and an emitter, and a suturing assembly comprising a needle 5703 and suturing material 5705 attached thereto configured to suture tissue T. The grasper 5701 is configured to actuate the needle 5703 through a complete suturing stroke by puncturing the surface of the tissue T with a tip 5704 of the needle 5703, crossing the gap 5706 of the tissue T, and causing the tip 5704 of the needle 5703 to puncture back out through the surface of the tissue T.

The grasper 5701 may be a part of a robotic system, for example, and can be actuated manually through the robot by an operator and/or automatically through the robot by a control program. As discussed in greater detail below, a repetitive portion of a suturing motion may be automated such as the suturing stroke. Such a robotic system can be seen in FIG. 1, for example. The grasper 5701 may be actuated by a robotic arm of the robotic system 110. Further to the above, the control circuits discussed herein in connection with the surgical suturing systems can be configured to operate the robotic system directly. In other instances, the control circuits can be configured to send instructions to a control circuit of the robotic system itself. The instruments, components, devices, systems, and methods disclosed herein can be used with the instruments, components, devices, systems, and methods disclosed in U.S. Pat. No. 9,072,535, entitled SURGICAL STAPLING INSTRUMENTS WITH ROTATABLE STAPLE DEPLOYMENT ARRANGEMENTS, which is incorporated by reference herein in its entirety.

As discussed above, the grasper 5701 may be robotically-assisted through certain control motions during a surgical suturing procedure. For example, the robotic system can be configured to rotate the grasper automatically through the suturing stroke such that a clinician does not have to perform the suturing stroke itself but, instead, may only be required to align the grasper 5701 and the needle 5703 to perform each suturing stroke. In such instances, the clinician may place the tip 5704 of the needle 5703 on the tissue to be sutured and then instruct the robot to initiate the suturing stroke sequence of the grasper 5701. In other instances, the grasper 5701 may be manually operated throughout the entire suturing procedure. At any rate, as discussed in greater detail below, the surgical visualization assembly 5702 is configured to monitor the position of the needle 5703, the grasper 5701, and/or any embedded structures, such as the embedded grasper 5701, during the suturing procedure. The surgical visualization assembly 5702 may be similar to that of any of the visualization systems discussed herein. The surgical visualization assembly 5702 may include a hyperspectral imaging device to image and visualize hidden, or embedded, critical tissue structures. The hyperspectral imaging and visualization system can calculate the position of tissue structures, e.g., a vein hidden below the surface of tissue in the illustrated example (FIG. 22), relative to a predicted suturing needle path or the suturing needle itself. The system can provide a warning, or alert, when the system determines, or calculates, that the needle 5703 and/or the suturing stroke path of the needle 5703 and the embedded grasper 5701 are too close to each other. The proximity that would warrant an alert may be selectable by a clinician before the suturing stroke is performed or may be recommended based on data provided by relevant standards. The determination process and control circuits for use with such surgical suturing tracking, or visualization, systems is explained in greater detail below.

FIG. 23 depicts a monitoring system 5710 displaying a surgical site, such as the one illustrated in FIG. 22. The monitoring system 5710 is configured to display the suturing process performed by the surgical suturing system 5700 and is augmented with a side display 5711 comprising a proximity indicator 5712. The side display 5711 comprises a warning zone and lights up when the suturing needle, and as a result the proximity indicator 5712, enters the warning zone. The monitoring system 5719 is configured to reproduce the surgical site in a display format by using the data collected by the surgical visualization assembly 5702. The monitoring system 5710 may use additional cameras and/or waveform sensors to replicate the surgical site on the display.

The monitoring system 5719 can further be configured to highlight various structures as different times. For example, if the proximity detected between the needle 5703' and the embedded structure is within a critical proximity, the embedded structure itself may be highlighted using any suitable highlighting technique, e.g., change color, brightness, and/or pattern. Moreover, additional visual indicia may be overlaid onto the displayed image to indicate to a clinician of a predicted suture path relative to an embedded structure. Such visual indicia may include an "X", for example, where a predicted suturing path of the needle may result in puncturing the embedded structure at the location marked with the "X". Anything capable of being detected by the cameras and/or waveform sensors within the surgical site can be highlighted and/or monitored such as, for example, the suturing material hidden or not hidden by tissue, the piercing tip of the needle, and/or the grasper 5701'. The monitoring system 5719 may also predict where the needle may exit the other side of the tissue gap and denote this location with some sort of visual indicia.

Still referring to FIG. 23, the side display 5711 can be configured to monitor the proximity of the needle and any critical structures or any desired combination of components that a clinician would want to monitor the relative proximity of. In various instances, the proximity of the tip of the needle and the embedded structure(s) are monitored and the closest distance between the needle tip and the embedded structure is indicated by the indicator 5712. As the distance between the needle tip and the embedded structure changes, the indicator 5712 moves to indicate this distance to a clinician. In various instances, zones can be provided and/or selected by a clinician to alert the clinician when the proximity falls within each zone individually. For example, a first zone may include a distance which is not critical to the clinician but is noteworthy of being communicated to the surgeon on the display. The clinician will be able to see that the indicator is in the first zone and may be alerted of such information. A second zone indicating a closer proximity than the first may issue a visual and audible warning alerting the clinician that the indicator is in the second zone with a heightened alert relative to the first zone. If the proximity reaches the second zone, a heightened alert may be initiated and may include, for example, a visual indication, an audible indication in the operating suite, and/or an adjust made to control motions being applied to the robot arm, for example, discussed in greater detail below. Zoning various levels of proximity is not limited to a display. Such a method can be used in a control circuit configured to control various components of the surgical suturing system such as, for example, the robot arm and/or the waveform sensor, among others.

In at least one aspect, hyperspectral imaging can visualize a metallic needle when buried by tissue. By having critical structures identified by this system as well, the robotic system can indicate when the suturing needle is within a certain proximity to the hidden critical structure. Given a point on a tissue surface that a surgeon selects, a system can provide information regarding various components of the procedure. For example, a control circuit can predict suture bite depth of a needle once placed on the surface of tissue. In such an instance, the suture bite depth of the needle can be calculated based on the position of the robotic arm to which the grasper holding the needle is attached and can be conveyed to a clinician. In at least one instance, structured light can be used to monitor and/or track movement of the tissue surface. Structured light can also be used to detect when the needle itself punctures through tissue and pokes back out of tissue by detecting when the tissue surface and, thus, the structured light pattern, is broken. A control circuit can also provide a recommended suture bite width for different tissues. In such an instance, the type of tissue can be detected and identified and then compared to a lookup table with predefined recommended suture bite widths. In at least one instance, a control circuit can break the suturing site into different zones and indicate to a clinician what zones to avoid while suturing. Any of this information can be communicated to a clinician and/or automatically fed into logic of a control circuit that controls any or all parts of a surgical suturing system. For example, a robotic system can automatically avoid a zone detected to be unsafe for suturing without indicating that this zone is restricted in any way to a clinician. Such a robotic system may prevent movement of its robotic arm components, for example, that would result in suturing a restricted zone, for example.

In at least one instance, structured light can be used to track the surface of tissue as it moves during a surgical suturing procedure. For example, a surgeon may select a starting point and/or location on the tissue surface for the suturing stroke to begin. This point would be the location for the needle to puncture the tissue and begin its suturing stroke. The grasper and, thus, the suturing needle may be automatically moved to this location by the robotic system and/or may be manually moved to this location by the clinician operating the robotic system. Before the tissue is actually punctured to begin the suturing stroke, the tissue and, thus, the surface of the tissue may move. If the surface of the tissue moves, it may be desirable to track this movement to track the movement of the location chosen for the beginning of the suturing stroke. The control system can interpret this data to automatically reposition the needle to where the chosen location has moved to and/or alert the clinician that the chosen location has moved. In at least one instance, the control circuit can provide updated information in real time to the clinician regarding the suturing stroke. For example, the control circuit can provide information such as and/or related to the capture width of the needle and/or the depth that the needle will travel during its suturing stroke.

FIGS. 24-26 illustrate a sequence of images that represent a robotically-assisted suturing motion utilizing a grasper 5721 connected to a surgical robot and a suturing needle 5724 configured to suture tissue T. The robotically-assisted suturing motion can be performed automatically by a robotic system. However, the full suturing operation may comprise manual portions wear a clinician may operate a robotic system to which the grasper 5721 is attached manually and automatic portions wear a clinician initiates an automatic sequence instruction to instruct the robotic system to perform that portion automatically. Such an arrangement allows the robot to automate tedious and/or repetitive portions of the suturing motion that, in at least one instance, are constant in all suturing procedures.

Still referring to FIGS. 24-26, the grasper 5721 comprises an articulation joint 5722 and grasping jaws 923 extending therefrom configured to be articulated and/or rotated relative to the shaft of the grasper 5721. Such graspers are commonly used in robotic systems. The needle 5724 comprises suturing material 5726 attached to a trailing end of the needle 5724 and a piercing tip 5725 configured to pierce tissue T and travel through the tissue T to install the suturing material 5726. FIG. 24 illustrates an initializing sequence of the robotically-assisted suturing motion where a clinician manually touches suture needle 5724 to the tissue T with a robotic arm, for example. Such an action may initiate the robotically-assisted suturing motion. In at least one instance, a waveform sensor and/or any suitable camera can detect this position and inform a control circuit that the portion of the suturing motion that involves piercing and turning through tissue, also referred to as the suturing stroke, is ready to be performed. Once in this position, a clinician may press a button, for example, on the robotic system to initiate the suturing stroke. When the button is pressed, the robotic system will automatically perform the suturing stroke portion of the suturing procedure by manipulating its components, such as the robotic arm, so that the grasper will move in a fashion to perform the suturing stroke. The motions applied to the grasper by the robotic system may vary between suturing strokes in the same procedure. For example, a camera may be used to map out the topography of the tissue and gather any other data from the surgical site for each suturing stroke. This information can be conveyed to a control circuit such that the robotic system can adjust its automated suturing stroke control program such that the control motions applied to the grasper are adjusted to perform a proper suturing stroke in each specific location. Such an arrangement may be advantageous where the tissue being sutured is not level, or flat, and the grasper must be angled, and/or tilted, to accommodate the topography. Of course, tissue may move during each stroke and between strokes. Such an arrangement can help accommodate constant tissue movement when data about the surgical site and, specifically, the tissue topography, for example, is conveyed in real time.

After the automated portion of the suturing motion is performed, the needle 5724 is in the location illustrated in FIG. 25. In at least one instance, the automated suturing stroke can be adjusted before and/or throughout the procedure based on clinician preference and/or any other information, for example. At any rate, the needle 5724 is ready to be pulled through the tissue T to pull the suturing material 5726 through the tissue T. FIG. 26 illustrates the grasper 5721 holding, or grabbing, the tip 5725 of the needle 5724. In at least one instance, grabbing the tip of the needle is part of the automated portion of the suturing motion. In another instance, grabbing the tip of the needle is not automated and clinician must manually grab the tip of the needle with the grasper. At any rate, the needle 5724 and, as a result, the suturing material 5726 are pulled through the tissue T with the grasper 5721 to complete a cycle of the suturing motion. Multiple cycles of the suturing motion can be performed depending on the clinician's suturing strategy. In instances where multiple cycles are performed, one or more cycles may comprise automation while one more other cycles may be entirely manual.

Various types of control programs and/or circuits can be employed with the devices and systems disclosed herein. FIG. 27 is a flowchart depicting an algorithm, or process, 5730 configured to be executed by a control circuit utilizing a surgical visualization feedback system to determine the relative position of a suturing needle and an embedded tissue structure. Such a system may be referred to as a surgical suturing tracking, or guiding, system, for example. The process 5730 comprises receiving an input 5731 to initiate the process 5730. Such an input may comprise a physical button that the clinician can press and/or a sensed condition within the surgical site, for example. It should be appreciated that physical initiation of the process 5730 is not necessary and that the algorithm can be initiated automatically by a robotic system. The process 5730 further comprises causing 5732 a spectral light emitter, such as those disclosed herein, to emit spectral light waves toward a suturing needle and a tissue structure. This function permits the system to detect the location various components within the surgical site such as, for example, the suturing needle and the tissue structure. In at least one instance, the spectral light emitter is configured to emit spectral light waves toward other components in addition to or in lieu of the needle and the tissue structure within the surgical site that are desired to be detected. At any rate, whatever components receive spectral light waves can reflect the spectral light waves. A waveform sensor can detect these light waves and the control circuit can receive 5733 an input corresponding to the waves reflected thereby.

Still referring to FIG. 27, the control circuit can then assess the proximity of the needle and the tissue structure. For example, the control circuit can determine, or calculate, 5734 a distance between the needle and the tissue structure based on the received input. In at least one instance, the data may include information to detect and determine a plurality of distances between multiple objects. For example, the control circuit may determine a distance between the needle tip and the tissue structure, the trailing end of the needle and the needle structure, and/or a plurality of sections of the needle and the tissue structure. The control circuit is then configured to interpret 5735 the data corresponding to the location of the objects detected. In at least one instance, the distance(s) determined by the control circuit may be compared to a lookup table of predetermined, or predefined, safe, or critical, distances. In at least one instance, the zoning method discussed above may be used to compare the determined distances to.

Interpreting the data may also include the control circuit taking action. For example, the control circuit can alert a clinician of the determined distance(s). The control circuit may alert a clinician only if the distance is less than or equal to a predefined critical distance. In at least one instance, the control circuit may alert the clinician of the distance via an audible indication, a tactile indication, and/or a visual indication, for example. In at least one instance, the control circuit may adjust the control motions being applied to the grasper and/or the waveform sensor by the clinician and/or the robotic system. In such an instance, for example, the control circuit may prevent further actuation and/or, pause the actuation, of the grasper until an adjustment of the suturing location is made by the clinician and/or automatically made by the robotic system at which point the algorithm can be executed again if desired. Adjusting the control motions may comprise applying reversing control motions to the grasper such that the needle is reversed through its suturing stroke to back away from a critical structure. In at least one instance, the needle is reversed until it is a predefined safe distance away from the critical structure and the control circuit awaits further instruction from a clinician. In at least one instance, the suturing stroke of the needle is completely reversed so that the suturing needle is completely out of the tissue being sutured until the control circuit receives further instruction. All such adjustments can be made aware to the clinician during the procedure. A clinician may also choose what type of adjust they would like to occur open reaching the critical distance between the needle and a critical structure.

FIG. 28 is a flowchart depicting an algorithm, or process, 5740 configured to be executed by a control circuit of a surgical suturing system. The process 5740 includes an automated suturing stroke such as the one discussed above. In this process, the automated suturing stroke is initiated 5741 by a clinician using any suitable input. As discussed above, the input may comprise an input may be delivered to the control circuit directly by a signal generated from a physical button that a clinician actuates or the input may comprise an automatically sensed condition during the surgical procedure. For example, a camera may detect a primed position of the needle and the grasper and use that detected image to begin the automated suturing stroke. Another example includes sensing contact between a tip of the needle and tissue. Yet another example may include beginning the suturing stroke manually after the system detects that the needle tip is in contact with the tissue and such initial manual movement triggers the automated suturing stroke by the robotic system.

The process 5740 further employs a spectral light emitter to emit 5742 spectral light waves into the surgical site and a waveform sensor to detect the location of the needle and/or embedded tissue structure. The waveform sensor collects data to be received 5743 as an input by the control circuit with which the control circuit then uses to assess 5744 the proximity of the needle and the tissue structure. As discussed above, various types of calculations can be made by the control circuit based on the data captured by the waveform sensor. Once the data is interpreted by the control circuit and the proximity of the needle and the tissue structure is assed, the assed proximity is then analyzed 5745 to decide if the assed proximity is outside of a predefined critical proximity range. For example, if the shortest distance detected between any part of the needle and any part of the tissue structure is 5 mm and the predefined critical proximity range less than 10 mm, then the control circuit will take appropriate action. In this example, if the shortest distance detected between the needle and the tissue structure is 15 mm, action may not be taken. In at least one instance, the clinician is made aware by the control circuit of the shortest distance between these structures at all times regardless of its relationship with a predefined critical proximity range. At any rate, if the assed proximity is within the predefined critical proximity range, the control circuit can take action 5746 such as any of those actions discussed above. For example, pausing robotic actuation of the grasper, alerting a clinician of the condition, and/or automatically applying reversing control motions to the grasper to move the needle away from the tissue structure a desired distance may all include actions that could be taken by the control circuit.

At this point, the suturing stroke may not be complete. The state of the suturing stroke is checked 5747 to determine if the suturing stroke must continue. In at least one instance, the suturing stroke may automatically adjust 5746 the control motions applied to the grasper by reversing the suturing stroke completely so that the needle is completely out of the tissue. In such an instance, the clinician may then be prompted to pick a new location for the suturing stroke and/or a robotic system may help or automatically pick a new location for the suturing stroke. In another instance, the robotic system may apply control motions to the grasper to automatically navigate around the tissue structure. In another instance, the clinician may choose to override any adjustment suggested and may continue on with the automatic suturing stroke and/or may continue the suturing stroke manually. The reader should appreciate that "manually" can refer to manually operating a robotic arm of a surgical robot to which the grasper and/or any other tool is connected with a robotic tool operating interface. The reader should also appreciate the "automatic" and/or "automated" can refer to actions, motions, and/or decisions being wholly or partially executed by a control circuit. Such a control circuit may comprise the logic described herein. In another instance, information is fed to a control circuit of the robotic system to automatically move the robotic arm.

After a control motion adjustment, for example, is made, and it is determined that the suturing stroke is not complete, the suturing stroke is then continued 5748. At this point, the control circuit can monitor these conditions in real time for example. In another instance, as discussed in greater detail below, this logic is performed prior to even beginning a suturing stroke and certain adjustments can be preempted by predicting the path of the suturing stroke prior to puncturing tissue with the needle.

FIG. 29 is a flowchart depicting an algorithm, or process, 5750 configured to be executed by a control circuit of a surgical suturing system. The process 5750 includes an automated suturing stroke such as the one discussed above. The process 5750 is similar to that of the process 5740 in some respects. However, the process 5750 includes predicting the path of the suturing stroke prior to beginning the suturing stroke and/or puncturing the tissue with the needle. This can be accomplished in different ways.

In at least one instance, the path of the suturing stroke is predicted by utilizing data known by the robotic system. For example, the position of the robotic arm and, as a result, the grasper and the needle, can be known within the robotic system itself. In at least one instance, data generated based on the position of the robotic controls with which a clinician operates the robot is communicated to the robotic system to position the robotic arms accordingly. This data can be utilized in the systems disclosed herein. In at least one instance, this data can be received by a control circuit and, along with known information about the surgical needle such as arc length and overall size, the control circuit can determine and/or calculate the predicted path of the suturing stroke given any position of the robotic arm.

In at least one instance, the path of the suturing stroke is predicted by using a waveform sensor and a spectral light emitter. In such an instance, knowing the position of the robotic arm may not be necessary. The waveform sensor and spectral light emitter can detect the needle directly and determine its position and shape. The control circuit can then determine, based on the needle's current position and a known suture swing motion provided by the grasper, where in the tissue the suturing stroke and, thus, the needle will pass. This results in determining the predicted path of the needle at any given position within the surgical site. In at least one instance, positional data corresponding to components in the robotic system, predetermined data such as size of needle, and imaging data can all be used to determine the predicted path of a suturing stroke.

Still referring to FIG. 29, the process 5750 further includes detecting 5753 any embedded tissue structures and assessing 5754 the proximity of the predicted path of the suturing stroke and the detected tissue structures. In at least one instance, the shortest distance between the detected tissue structures and the entire predicted path of the suturing stroke is conveyed to a clinician and/or within the surgical suturing system. In at least one instance, a range of distances defining a proximity field, or range, are conveyed to a clinician and/or within the surgical suturing system. At any rate, assessing the proximity of the predicted path of the suturing stroke and the needle can provide a way to help ensure that each suturing stroke is performed outside of a predefined critical proximity range without puncturing tissue and having to make an adjustment mid stroke. The predefined critical proximity range can be selectable by a clinician and/or predefined based on suturing standards.

If the predicted suturing stroke is entirely outside of the predefined critical proximity range, the robotic system may automatically perform 5758 the suturing stroke with the grasper. In at least one instance, the clinician can initiate the automated suturing stroke after being informed by the control circuit that the predicted path of the suturing stroke is entirely outside of the predefined critical proximity range. If the predicted suturing stroke is within the predefined critical proximity range, a variety of actions, adjustments, and/or alerts 5756 may occur. In at least one instance, the clinician can be alerted that the predicted path falls within the critical range and can be prompted to select a manual override option where the robotic system can automatically perform the suturing stroke and/or the clinician can manually operate the robotic system to perform the suturing stroke. In another instance, the robotic system may automatically adjust the starting position of the suturing stroke to recommend a new location such that, at the new location, the new predicted path of the suturing stroke is entirely outside of the predefined critical proximity range. In at least one instance, the clinician is provided with several safe options regarding a new starting position for the suturing stroke and the clinician can pick which option they would like to perform the suturing stroke. In such an instance, the clinician can pick another option and the robotic system can automatically move the robotic arm and, thus, the grasper and the needle, to the new suggested location. The robotic system can then automate and perform the new suturing stroke. Nonetheless, the control circuit checks 5757 to see if the suturing stroke is complete and continues to monitor the predicted path of the suturing stroke based on the current position of the needle.

Referring now to FIG. 30, a process 5760 configured to be executed by a clinician and/or a control circuit utilizing a robotically assisted suture motion is illustrated. The process 5760 comprises an automatic shut off if a needle is within a defined proximity of a non visible and/or embedded, critical structure. The process 5760 is initiated when a clinician operates a robotic arm to contact 5761 the surface of tissue to be sutured. If the clinician is satisfied with the placed position, the clinician can initiate 5762 the automatic suturing motion. In at least one instance, a physical button is pressed by the clinician to initiate the automatic suturing motion. The grasper then rotates 5763 the needle through the tissue controlled by a robotic arm. At this point, or before this point at any time, the clinician may optionally select 5764 a critical distance at which the clinician wants to be maintained between the needle and the critical structure. Such a distance may already be selected within the control program based on sensed conditions within the surgical site. In at least one instance, the distance is predefined and is based on suturing standards.

Still referring to FIG. 30, the system visualizes 5766 any embedded structures and the needle, using an imaging system during the automatic suturing stroke, and checks 5765 if the needle and the critical structure reach and/or surpass the critical distance. In at least one instance, the system looks for a critical distance that is less than the critical distance. In at least one instance, the system looks for a critical distance that is less than or equal to the critical distance. In at least one instance, the system looks for a critical distance that is approaching the critical distance and initiates an alert cycle before the critical distance is reached. Any suitable parameter other than or in addition to distance may be used. Also, the piercing tip of the needle may be specifically be visualized and checked using this process 5760. Any suitable portion of the needle can be detected and used to measure the proximity between the needle and the tissue structure(s).

If the distance reaches the critical distance, the automatic suturing motion is stopped 5767 and the clinician, or surgeon, is alerted of the proximity of the needle and the tissue structure. If the distance is not less than or equal to the critical distance, the automatic suturing motion continues 5768 until the automatic suturing motion is completed by the robotic arm and, thus, the grasper. The system can monitor the proximity of the needle and any embedded tissue structures against the set critical distance during the entire automatic suturing motion. In at least one instance, the proximity of the needle and any embedded tissue structures are monitored during only a portion of the automatic suturing stroke. In at least one instance, the proximity of the needle and any embedded tissue structures is monitored as long as the imaging system can detect one and/or both the needle and any embedded tissue structures with the surgical site. At any rate, after the automated suturing motion is complete, the clinician grabs 5769 the piercing tip of the needle and pulls the needle and suturing material through the tissue to complete the suturing cycle. The clinician and/or the robotic system can then reposition the needle to prepare for an additional stitch if desired at which point the process 5760 can be executed again.

Referring now to FIG. 31, a process 5770 configured to be executed by a clinician and/or a control circuit utilizing a robotically assisted suture motion is illustrated. The process 5770 is similar to the process 5760 in many respects. The process 5770 comprises an automatic shut off if a needle is within a defined proximity of a non visible and/or embedded, critical structure. However, the process 5770 includes the ability to predict the needle path in addition to monitoring the proximity of the needle and any embedded tissue structures in real time. In at least one instance, the either proximity monitoring method can be used exclusively. In at least one instance, a clinician can choose which method they want to use to monitor the proximity of the needle and any embedded tissue structures. In such an instance, the clinician may choose both methods (suturing path prediction and real-time analysis).

The process 5770 is initiated when a clinician operates a robotic arm to contact 5771 the surface of tissue to be sutured. If the clinician is satisfied with the placed position, the clinician can initiate 5772 the automatic suturing motion. In at least one instance, a physical button is pressed by the clinician to initiate the automatic suturing motion. At this point, the algorithm determines 5773 if the proximity of the needle and/or any part of the needle and any embedded tissue structures visualized by an imaging system is within a critical proximity range based on the current position of the needle. The system can determine this by calculating the arc of the suture swing performed by the robotic arm and comparing that predicted path to the imaged position of the embedded structure(s). In at least one instance, the algorithm performs this function automatically without a clinician needing to initiate it such that the information is already determined before the clinician initiates the automated suturing motion. At any rate, the automated suturing motion is not actuated if the proximity between the predicted path and any embedded tissue structures is within a critical proximity range. Such a range can be selectable and/or predefined.

If the predicted path is outside of the critical proximity range, the grasper then rotates 5774 the needle through the tissue controlled by a robotic arm. At this point, or before this point at any time, the clinician may optionally select 5775 a critical proximity range at which the clinician wants to be maintained between the needle and/or the predict path of the needle and the critical structure. Such a distance may already be selected within the control program based on sensed conditions within the surgical site. In at least one instance, the distance is predefined and is based on suturing standards.

Still referring to FIG. 31, the system visualizes 5777 any embedded structures and the needle, using an imaging system during the automatic suturing stroke, and checks 5776 if the needle and the critical structure reach and/or surpass the critical proximity range. If the proximity reaches the critical proximity range, the suturing motion is stopped 5778 and the clinician is alerted at which point a variety of actions 5781 may occur. Such actions may include: the automatic suturing motion is stopped, the needle is automatically retreated out of the tissue, the clinician is given manual control of the robotic system, and/or the robotic system determines a new path that would provide a suturing stroke outside of the critical proximity range and the robotic system navigates around the tissue structure. If the proximity is not within the critical proximity range, the suturing stroke is continued 5779 until the suturing stroke is complete or until the critical proximity range is reached. At any rate, once the suturing stroke is complete, a clinician and/or the robotic system can grab 5782 the needle to begin another stitch cycle if desired. In at least one instance, the robotic system can use data collected by the imaging system and/or the data corresponding to the position of the robotics arm holding the grasper and needle to determine the location of the needle tip so that the robotic system can automatically grab the tip of the needle one a suturing stroke is complete.

In at least one instance, an imaging system can be used to monitor the proximity between a suturing needle and a critical structure by detecting variations in the tissue structure itself. For example, as the needle displaces tissue during the suturing stroke or as the needle is pressed against tissue, this may result in pressure being applied to a vein, for example. This pressure can cause a fluctuation in density of the vein. This fluctuation in density can cause the vein to reflect spectral light waves differently. For example, a vein unaffected by a needle can comprise a lower density than a vein being pressed against directly or indirectly by a needle in close proximity. Such density fluctuation can provide different reflection signatures of the spectral light waves. As a result, a hyperspectral camera can detect the proximity of the needle and the tissue structure, such as a vein, for example, by only monitoring the spectral light reflection signatures of the vein. In another instance, the tissue around the vein can be monitored in a similar fashion. In yet another instance, the surface of the vein or the barrier between the vein and the tissue can be monitored for variation in porosity as the needle affects the area. This may also cause different spectral light reflection signatures. In at least one instance, a clinician can be alerted of the pressure being applied to the tissue and/or tissue structures during a surgical suturing procedure.

In at least one instance, a visualization system can be used to monitor the flow of liquid through a vessel. For example, Doppler ultrasound may be used to monitor the flow of blood, for example, through a vessel. During a suturing procedure, a needle may affect the flow of blood through a vessel. For example, in at least one instance, flow of blood may slow due to a constricting condition created by the needle around the vessel. In another instance, flow of blood may increase due to a puncture in the vessel itself. At any rate, the imaging system may include Doppler ultrasound to detect rate of flow of liquid within a vessel itself and, along with hyperspectral imaging, for example, can help prevent puncturing a blood vessel during a suturing stroke of a needle. This information can be communicated to a control circuit and thus to a clinician during a surgical suturing procedure.

In at least one embodiment, a process utilizing a robotically-assisted suturing motion is provided that comprises a shut off if a suture needle is in proximity of a non-visible critical tissue structure, according to at least one aspect of the present disclosure. The process prevents the suture needle from contacting a tissue structure during robotic surgery. The clinician initiates the suturing process by touching a point on the surface of the tissue. The clinician then selects the "penetrate" button to cause the suture needle, controlled by a robotically actuated, wristed grasper, to rotate through tissue. A warning distance between a path of the suture needle and the hidden tissue structure is set by the clinician to be a distance of X, such as 5 mm for example, and a tip of the suture needle is visualized by a hyperspectral imaging and visualization system. The system checks to determine if the path of the suture needle is within 5 mm of the tissue structure. If 'yes', the system stops rotation of the suture needle and indicates a proximity warning to the clinician and if 'no', the system continues to rotate the suture needle until the tip of the needle reaches a predetermined end of rotation. The clinician then grabs the tip of the suture needle and repositions it for the next stitch desired.

In at least one embodiment, hyperspectral imaging can visualize a metallic needle when buried by tissue. By having critical structures identified by this system in addition to the needle, a robotic system can help prevent the needle and a tissue structure from contacting each other. In various instances, the suturing methodology described herein is consistent with the "touch and turn" method of clinical instruction for how to suture, generally. The clinician controls the "touch," which sets up needle and, specifically, needle tip placement and suture spacing (i.e. manipulate tissue to be sutured such that the stitch captures a desired width of tissue). The robotic system controls the "turn" (the suturing stroke—including the needle piercing and traveling through tissue) and has the ability to turn off the "turn" sequence if a critical structure is present. Any suitable technology may be used for sensing the needle, for example, within a surgical site. For example, sensing using ultrasound, magnetic sensing, and/or capacitive sensing may be used to monitor the location of the needle.

In at least one embodiment, a process for suturing is provided utilizing a robotically—assisted suture motion and proximity suture motion prevention, according to at least one aspect of the present disclosure. The process prevents the suture needle from contacting a critical structure during robotic surgery. In this process, after the surgeon selects the "penetrate" button, based on the calculated arc of the suture swing and known position of a hidden critical structure, the system prevents the rotation of the suture needle if the suture would be within a defined distance of the hidden critical structure. This distance may be selectable by a clinician and/or predetermined. Furthermore, once the rotation is stopped, the system proceeds according to three options: (1) stop, retract, and/or back out suture; (2) give surgeon control; and/or (3) auto navigate to avoid the hidden critical structure.

EXAMPLES

Various aspects of the subject matter described herein are set out in the following numbered examples.

Example 1

A surgical suturing tracking system configured for use with a suturing needle. The surgical suturing tracking system comprises a spectral light emitter, a waveform sensor, and a control circuit coupled to the waveform sensor, wherein the control circuit is configured to cause the spectral light emitter to emit spectral light waves toward a suturing needle and a tissue structure, receive an input corresponding to the spectral light waves reflected by the needle and the tissue structure, and determine a distance between the needle and the tissue structure based on the received input.

Example 2

The surgical suturing tracking system of Example 1, wherein the control circuit is further configured to alert a clinician of the determined distance between the needle and the tissue structure.

Example 3

The surgical suturing tracking system of Examples 1 or 2, wherein the control circuit is further configured to alert a clinician of the determined distance between the needle and the tissue structure when the determined distance is less than or equal to a predefined distance.

Example 4

The surgical suturing tracking system of Examples 1, 2, or 3, wherein the control circuit is further configured to compare the determined distance between the needle and the tissue structure to a predefined distance profile comprising a first zone indicative of a distance that is approaching a critical distance and a second zone indicative of a distance that has reached the critical distance, and wherein the control circuit is further configured to alert a clinician if the determined distance reaches at least one of the first zone and the second zone.

Example 5

The surgical suturing tracking system of Examples 1, 2, 3, or 4, wherein the control circuit is further configured to calculate a recommended suture bite depth.

Example 6

The surgical suturing tracking system of Examples 1, 2, 3, 4, or 5, wherein the control circuit is further configured to calculate a recommended suture bite width.

Example 7

The surgical suturing tracking system of Examples 1, 2, 3, 4, 5, or 6, wherein the control circuit is configured to determine a distance between a tip of suturing needle and the tissue structure.

Example 8

A surgical suturing system comprising a robotically-assisted suturing device. The robotically-assisted suturing device comprises a grasper configured to be manipulated automatically by a surgical robot and manually by a clinician and a suturing needle configured to be actuated through a suturing stroke by the grasper when automatic control motions are robotically applied to the grasper. The surgical suturing system further comprises a spectral light emitter, a waveform sensor, and a control circuit coupled to the waveform sensor and the robotically-assisted suturing device. The control circuit is configured to cause the spectral light emitter to emit spectral light waves toward the suturing needle and a tissue structure, receive an input corresponding spectral light waves reflected by the needle and the tissue structure, determine a distance between the needle and the tissue structure, and adjust the control motions robotically applied to the grasper when the determined distance between the needle and the tissue structure is less than or equal to a predefined distance.

Example 9

The surgical suturing system of Example 8, wherein adjusting the control motions comprises pausing actuation of the grasper.

Example 10

The surgical suturing system of Examples 8 or 9, wherein adjusting the control motions comprises applying reversing control motions to the grasper to reverse the suturing stroke of the needle.

Example 11

The surgical suturing system of Examples 8, 9, or 10, wherein the control circuit is further configured to alert a clinician of the determined distance between the needle and the tissue structure.

Example 12

The surgical suturing system of Examples 8, 9, 10, or 11, wherein the control circuit is further configured to alert a clinician of the determined distance between the needle and the tissue structure when the determined distance reaches the predefined distance.

Example 13

The surgical suturing system of Examples 8, 9, 10, 11, or 12, wherein the control circuit is further configured to calculate a recommend suture bite depth.

Example 14

The surgical suturing system of Examples 8, 9, 10, 11, 12, or 13, wherein the control circuit is further configured to calculate a recommend suture bite width.

Example 15

The surgical suturing system of Examples 8, 9, 10, 11, 12, 13, or 14, wherein the control circuit is configured to determine a distance between a tip of suturing needle and the tissue structure.

Example 16

A surgical suturing system comprising a robotically-assisted suturing device. The robotically-assisted suturing device comprises a grasper configured to be manipulated automatically by a surgical robot and manually by a clinician and a suturing needle configured to be actuated through a suturing stroke by the grasper when automatic control motions are robotically applied to the grasper. The surgical suturing system further comprises a spectral light emitter, a waveform sensor, and a control circuit coupled to the waveform sensor and the robotically-assisted suturing device. The control circuit is configured to cause the spectral light emitter to emit spectral light waves toward a suturing needle and a tissue structure, receive an input corresponding to the spectral light waves reflected by the needle and the tissue structure, determine a position of the needle and a position of the tissue structure based on the received input, predict a path of the suturing stroke to be performed by the robotically assisted suturing device based on the received input, and determine a distance between the predicted path of the suturing stroke and the tissue structure.

Example 17

The surgical suturing system of Example 16, wherein the control circuit is further configured to alert a clinician of the determined distance between the predicted path of the suturing stroke and the tissue structure.

Example 18

The surgical suturing system of Examples 16 or 17, wherein the control circuit is further configured to alert a clinician of the determined distance between the predicted path of the suturing stroke and the tissue structure when the determined distance is less than or equal to a predefined distance.

Example 19

The surgical suturing system of Examples 16, 17, or 18, wherein the control circuit is further configured to compare the determined distance between the predicted path of the suturing stroke and the tissue structure to a predefined distance profile comprising a first zone indicative of a distance that is approaching a critical distance and a second zone indicative of a distance that is equal to or less than the critical distance, and wherein the control circuit is further configured to alert a clinician if the determined distance is within at least one of the first zone and the second zone.

Example 20

The surgical suturing system of Examples 16, 17, 18, or 19, wherein the control circuit is configured to determine a distance between a predicted suturing stroke path of a tip of the suturing needle and the tissue structure.

Example 21

A surgical suturing system comprising a grasper configured to be manipulated automatically by a surgical robot and manually by a clinician, a suturing needle configured to be actuated through a suturing stroke by the grasper, and a control circuit. The control circuit is configured to receive an input from the clinician to cause the surgical robot to actuate the needle through the suturing stroke automatically, determine a distance between the needle and a tissue structure, compare the distance to a predefined critical distance, and adjust control motions applied to the grasper by the surgical robot if the determined distance is less than or equal to the predefined critical distance.

Example 22

The surgical suturing system of Example 21, wherein the predefined critical distance is selectable by the clinician.

Example 23

The surgical suturing system of Examples 21 or 22, further comprising a spectral light emitter and a waveform sensor configured to detect spectral light reflections to detect the position of the needle and the position of the tissue structure.

Example 24

The surgical suturing system of Examples 21, 22, or 23, wherein adjusting control motions applied to the grasper comprises applying reversing control motions to reverse the suturing stroke.

Example 25

The surgical suturing system of Examples 21, 22, 23, or 24, wherein adjusting control motions applied to the grasper comprises pausing the application of control motions to the grasper to pause the suturing stroke.

Example 26

The surgical suturing system of Examples 21, 22, 23, 24, or 25, wherein adjusting control motions applied to the grasper further comprises giving manual control of the grasper the clinician.

Example 27

The surgical suturing system of Examples 21, 22, 23, 24, 25, or 26, wherein adjusting control motions applied to the grasper comprises automatically adjusting the control motions applied to the grasper to navigate away from the tissue structure and continuing the suturing stroke.

Example 28

The surgical suturing system of Examples 21, 22, 23, 24, 25, 26, or 27, wherein the control circuit is further configured to alert the clinician if the determined distance is less than or equal to the predefined critical distance.

Example 29

The surgical suturing system of Examples 21, 22, 23, 24, 25, 26, 27, or 28, wherein the determined distance comprises the distance between a tip of the needle and the tissue structure.

Example 30

The surgical suturing system of Examples 21, 22, 23, 24, 25, 26, 27, 28, or 29, wherein the input corresponding to the position of the needle is generated by at least one of an ultrasonic device, a magnetic sensor, and a capacitive sensor.

Example 31

A surgical suturing system comprising a grasper configured to be manipulated automatically by a surgical robot and manually by a clinician, a suturing needle configured to be actuated through a suturing stroke by the grasper, and a control circuit. The control circuit is configured to predict a path of the suturing stroke after receiving an input from the clinician, detect a tissue structure, and assess proximity of the predicted path and the detected tissue structure.

Example 32

The surgical suturing system of Example 31, wherein assessing the proximity of the predicted path and the detected tissue structure comprises determining a shortest distance between the predicted path and the detected tissue structure.

Example 33

The surgical suturing system of Examples 31 or 32, wherein the control circuit is further configured to alert the clinician if the assed proximity is within a predefined critical proximity range.

Example 34

The surgical suturing system of Example 33, wherein the predefined critical proximity range is selectable by the clinician.

Example 35

The surgical suturing system of Examples 31, 32, 33, or 34, further comprising a spectral light emitter and a waveform sensor configured to detect spectral light reflections to detect the tissue structure.

Example 36

The surgical suturing system of Examples 31, 32, 33, 34, or 35, wherein the control circuit is further configured to apply an automatic control motion to the grasper to perform the suturing stroke if the assessed proximity is not within a predefined critical proximity range.

Example 37

The surgical suturing system of Examples 31, 32, 33, 34, 35, or 36, wherein the control circuit is further configured to recommend a different location to begin the suturing stroke when the assessed proximity is within a predefined critical proximity range such that, at the different location the suturing stroke would define a different path outside of the predefined critical proximity range.

Example 38

The surgical suturing system of Examples 31, 32, 33, 34, 35, 36, or 37, wherein the control circuit is further configured to allocate manual control to the clinician when the assessed proximity is within a predefined critical proximity range.

Example 39

The surgical suturing system of Examples 31, 32, 33, 34, 35, 36, 37, or 38, wherein the control circuit is further configured to automatically adjust control motions applied to the grasper to navigate the predicted path away from the tissue structure outside of a predefined critical proximity range and continue the suturing stroke.

Example 40

The surgical suturing system of Examples 31, 32, 33, 34, 35, 36, 37, 38, or 39, wherein the assed proximity comprises determining a shortest distance between a predicted path of a tip of the needle and the tissue structure.

Example 41

A surgical suturing tracking system configured to detect and guide a suturing needle during a surgical suturing procedure, wherein the surgical suturing track system comprises a control circuit configured to predict a path of a needle suturing stroke after receiving an input from a clinician, detect an embedded tissue structure, and assess proximity of the predicted path and the detected embedded tissue structure.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

What is claimed is:

1. A surgical suturing tracking system configured for use with a suturing needle, wherein the surgical suturing tracking system comprises:
   a spectral light emitter;
   a waveform sensor; and
   a control circuit coupled to the waveform sensor, wherein the control circuit is configured to:
      cause the spectral light emitter to emit spectral light waves toward the suturing needle and a tissue structure;
      receive an input corresponding to the spectral light waves reflected by the suturing needle and the tissue structure; and
      determine a distance between the suturing needle and the tissue structure based on the received input,
   wherein the surgical suturing tracking system is configured to control a robotic suturing system using the determined distance between the suturing needle and the tissue structure.

2. The surgical suturing tracking system of claim 1, wherein the control circuit is further configured to alert a clinician of the determined distance between the suturing needle and the tissue structure.

3. The surgical suturing tracking system of claim 1, wherein the control circuit is further configured to alert a clinician of the determined distance between the suturing needle and the tissue structure when the determined distance is less than or equal to a predefined distance.

4. The surgical suturing tracking system of claim 1, wherein the control circuit is further configured to compare the determined distance between the suturing needle and the tissue structure to a predefined distance profile comprising a first zone indicative of a distance that is approaching a critical distance and a second zone indicative of a distance that has reached the critical distance, and wherein the control circuit is further configured to alert a clinician if the determined distance reaches at least one of the first zone and the second zone.

5. The surgical suturing tracking system of claim 1, wherein the control circuit is further configured to calculate a recommended suture bite depth.

6. The surgical suturing tracking system of claim 1, wherein the control circuit is further configured to calculate a recommended suture bite width.

7. The surgical suturing tracking system of claim 1, wherein the control circuit is configured to determine a distance between a tip of the suturing needle and the tissue structure.

8. A surgical suturing system, comprising:
 a robotically-assisted suturing device, comprising:
  a grasper configured to be manipulated automatically by a surgical robot and manually by a clinician; and
  a suturing needle configured to be actuated through a suturing stroke by the grasper when automatic control motions are robotically applied to the grasper;
 a spectral light emitter;
 a waveform sensor; and
 a control circuit coupled to the waveform sensor and the robotically-assisted suturing device, wherein the control circuit is configured to:
  cause the spectral light emitter to emit spectral light waves toward the suturing needle and a tissue structure;
  receive an input corresponding to the spectral light waves reflected by the suturing needle and the tissue structure;
  determine a distance between the suturing needle and the tissue structure; and
  adjust the control motions robotically applied to the grasper when the determined distance between the suturing needle and the tissue structure is less than or equal to a predefined distance.

9. The surgical suturing system of claim 8, wherein adjusting the control motions comprises pausing actuation of the grasper.

10. The surgical suturing system of claim 8, wherein adjusting the control motions comprises applying reversing control motions to the grasper to reverse the suturing stroke of the suturing needle.

11. The surgical suturing system of claim 8, wherein the control circuit is further configured to alert a clinician of the determined distance between the suturing needle and the tissue structure.

12. The surgical suturing system of claim 8, wherein the control circuit is further configured to alert a clinician of the determined distance between the suturing needle and the tissue structure when the determined distance reaches the predefined distance.

13. The surgical suturing system of claim 8, wherein the control circuit is further configured to calculate a recommend suture bite depth.

14. The surgical suturing system of claim 8, wherein the control circuit is further configured to calculate a recommend suture bite width.

15. The surgical suturing system of claim 8, wherein the control circuit is configured to determine a distance between a tip of the suturing needle and the tissue structure.

16. A surgical suturing system, comprising:
 a robotically-assisted suturing device, comprising:
  a grasper configured to be manipulated automatically by a surgical robot and manually by a clinician; and
  a suturing needle configured to be actuated through a suturing stroke by the grasper when automatic control motions are robotically applied to the grasper;
 a spectral light emitter;
 a waveform sensor; and
 a control circuit coupled to the waveform sensor and the robotically-assisted suturing device, wherein the control circuit is configured to:
  cause the spectral light emitter to emit spectral light waves toward the suturing needle and a tissue structure;
  receive an input corresponding to the spectral light waves reflected by the suturing needle and the tissue structure;
  determine a position of the suturing needle and a position of the tissue structure based on the received input;
  predict a path of the suturing stroke to be performed by the robotically assisted suturing device based on the received input; and
  determine a distance between the predicted path of the suturing stroke and the tissue structure.

17. The surgical suturing system of claim 16, wherein the control circuit is further configured to alert a clinician of the determined distance between the predicted path of the suturing stroke and the tissue structure.

18. The surgical suturing system of claim 16, wherein the control circuit is further configured to alert a clinician of the determined distance between the predicted path of the suturing stroke and the tissue structure when the determined distance is less than or equal to a predefined distance.

19. The surgical suturing system of claim 16, wherein the control circuit is further configured to compare the determined distance between the predicted path of the suturing stroke and the tissue structure to a predefined distance profile comprising a first zone indicative of a distance that is approaching a critical distance and a second zone indicative of a distance that is equal to or less than the critical distance, and wherein the control circuit is further configured to alert a clinician if the determined distance is within at least one of the first zone and the second zone.

20. The surgical suturing system of claim 16, wherein the control circuit is configured to determine a distance between a predicted suturing stroke path of a tip of the suturing needle and the tissue structure.

* * * * *